US012576104B2

(12) United States Patent
Pitucha et al.

(10) Patent No.: US 12,576,104 B2
(45) Date of Patent: Mar. 17, 2026

(54) DENTAL PREPARATION COMPRISING FIBERS BASED ON HYALURONIC ACID WITH REGULATED BIODEGRADABILITY

(71) Applicant: CONTIPRO A.S., Dolni Dobrouc (CZ)

(72) Inventors: Tomas Pitucha, Chrudim (CZ); Jakub Suchanek, Vrchovnice (CZ); Kristyna Chmelickova, Letohrad (CZ); Lucie Horackova, Usti nad Orlici (CZ); Jana Matonohova, Jimramov (CZ); Tomas Medek, Ceska Trebova (CZ); Jozef Rosa, Senica (SK); Romana Sulakova, Usti nad Orlici (CZ); Lida Grusova, Jablonne nad Orlici (CZ); Radovan Buffa, Humenne (SK); Martina Hermannova, Zamberk (CZ); Jarmila Husby, Litomysl (CZ); Vladimir Velebny, Zamberk (CZ)

(73) Assignee: CONTIPRO A.S., Dolni Dobrouc (CZ)

( * ) Notice: Subject to any disclaimer, the term of this patent is extended or adjusted under 35 U.S.C. 154(b) by 768 days.

(21) Appl. No.: 17/759,259

(22) PCT Filed: Jan. 5, 2021

(86) PCT No.: PCT/CZ2021/050009
§ 371 (c)(1),
(2) Date: Jul. 21, 2022

(87) PCT Pub. No.: WO2021/148066
PCT Pub. Date: Jul. 29, 2021

(65) Prior Publication Data
US 2023/0069878 A1 Mar. 9, 2023

(30) Foreign Application Priority Data
Jan. 24, 2020 (CZ) ................................. PV2020-37

(51) Int. Cl.
*A61K 31/728* (2006.01)
*A61K 9/00* (2006.01)
(Continued)

(52) U.S. Cl.
CPC .......... *A61K 31/728* (2013.01); *A61K 9/0063* (2013.01); *A61K 9/70* (2013.01);
(Continued)

(58) Field of Classification Search
CPC .......... A61P 1/02; A61P 31/04; A61K 31/728; A61K 9/0063; A61K 9/70; A61K 31/155; A61K 31/444
See application file for complete search history.

(56) References Cited

U.S. PATENT DOCUMENTS 4,175,326 A 11/1979 Goodson
4,764,377 A 8/1988 Goodson
(Continued)

FOREIGN PATENT DOCUMENTS

CZ 22394 U1 6/2011
CZ 28634 U1 9/2015
(Continued)

OTHER PUBLICATIONS

Casale et al. "Hyaluronic acid: Perspectives in dentistry, A systematic review" in International Journal of Immunopathology & Pharmacology, 2016 pp. 572-582. (Year: 2016).*
(Continued)

*Primary Examiner* — Blessing M Fubara
(74) *Attorney, Agent, or Firm* — Ingrassia Fisher & Lorenz, LLP | IF&L

(57) ABSTRACT

A biodegradable dental preparation comprising at least one water-soluble fiber from hyaluronic acid or a physiologically acceptable salt thereof and at least one fiber from a non-polar derivative of hyaluronic acid is disclosed. The dental prepa-
(Continued)

PERIODONTAL POCKET

CROWN

HEALTHY PERIODONTIUM

UPPER TEXTILE UNIT (slowly degrading)

GINGIVAL SULCUS (SULCUS GINGIVALIS)

MIDDLE TEXTILE UNIT (medium fast degrading)

PERIODONTAL LIGAMENT

RECEDING BONE

BOTTOM TEXTILE UNIT (rapidly degrading)

ALVEOLAR BONE

DISSOLVED HYALURONAN

TOOTH ROOT

GUM

BASE OF PERIODONTAL POCKET ration may comprise an antimicrobial agent. The dental preparation may be useful in the treatment of periodontal disease or in the treatment of injuries in the periodontium and oral mucosa. Methods of preparing the dental preparations, fibers thereof, and related compositions thereto, are also disclosed.

32 Claims, 6 Drawing Sheets

(51) Int. Cl.

| | |
|---|---|
| *A61K 9/70* | (2006.01) |
| *A61K 31/155* | (2006.01) |
| *A61K 31/444* | (2006.01) |
| *A61P 1/02* | (2006.01) |
| *A61P 31/04* | (2006.01) |

(52) U.S. Cl.
CPC .......... *A61K 31/155* (2013.01); *A61K 31/444* (2013.01); *A61P 1/02* (2018.01); *A61P 31/04* (2018.01)

(56) References Cited

U.S. PATENT DOCUMENTS

| | | | |
|---|---|---|---|
| 4,892,736 | A | 1/1990 | Goodson |
| 5,202,431 | A | 4/1993 | Della Valle et al. |
| 5,447,940 | A | 9/1995 | Wilson et al. |
| 5,622,707 | A | 4/1997 | Dorigatti et al. |
| 5,837,278 | A | 11/1998 | Geistlich et al. |
| 6,720,009 | B2 | 4/2004 | Gestrelius et al. |
| 10,689,464 | B2 * | 6/2020 | Dusankova ................ C08J 5/18 |
| 11,425,907 | B2 * | 8/2022 | Buffa ...................... A61L 27/20 |
| 11,427,652 | B2 * | 8/2022 | Buffa ...................... A61P 31/04 |
| 2002/0026039 | A1 | 2/2002 | Bellini et al. |
| 2009/0155326 | A1 | 6/2009 | Mack et al. |

FOREIGN PATENT DOCUMENTS

| | | | | |
|---|---|---|---|---|
| CZ | 308010 | B6 | 10/2019 | |
| CZ | 2018426 | A3 | 10/2019 | |
| CZ | 2018428 | A3 | 12/2019 | |
| EP | 0216453 | A2 | 4/1987 | |
| FR | 3035790 | A3 * | 11/2016 | ............. A61P 31/02 |
| GB | 2223027 | A | 3/1990 | |
| NO | 0059469 | A2 | 10/2000 | |
| WO | 2010068940 | A2 | 6/2010 | |
| WO | 2012089179 | A1 | 7/2012 | |
| WO | 2014082610 | A1 | 6/2014 | |
| WO | 2014082611 | A1 | 6/2014 | |
| WO | WO-2016141903 | A1 * | 9/2016 | ............. A61K 45/06 |
| WO | 2016185497 | A1 | 11/2016 | |
| WO | 2018158764 | A1 | 9/2018 | |

OTHER PUBLICATIONS

Petr Snetkov et al., "Hyaluronan-Based Nanofibers: Fabrication, Characterization and Application" in Polymers, 2019, pp. 1-25. (Year: 2019).*
FR 3035790 A3 Eng Trans from Espacenet, 2016 (Year: 2016).*
Golub, L. M., Suomalainen, K. and Sorsa, T., 1992. Host modulation with tetracyclines and their chemically modified analogues. Curr Opin Dent,2, 80-90.
Jain, N., Jain, G.K., Javed, S et al., 2008. Recent approaches for the treatment of periodontitis. Drug Discovery Today 13, 932-943.
Mller,G., Kramer,A., 2008. Biocompatibility index of antiseptic agents by parallel assessment of antimicrobial activity and cellular cytotoxicity. J. Antimicrob. Chemother, 64, 1281-87.
Da Rocha HA, Silva CF, Santiago FL, Martins LG, Dias PC, De Magalhães D. Local Drug Delivery Systems in the Treatment of Periodontitis: A Literature Review. J Int Acad Periodontol. Jul. 2015;17(3):82-90.
Gurha, S et al., 2016. Effect of Tetracycline Hydrochloride Fibers (PeriocolTc) on The Level of P. Gingivalis in Chronic Generalized Periodontitis: Clinical & Microbiological Study. IOSR Journal of Dental and Medical Sciences, 15 (8), 100107.
Khattri S, Arora A, Sumanth KN, Prashanti E, Bhat KG, Kusum CK, Johnson TM, Lodi G. Adjunctive systemic antimicrobials for the non-surgical treatment of chronic and aggressive periodontitis. Cochrane Database Syst Rev. Feb. 23, 2017;2017(2):CD012568. doi: 10.1002/14651858.CD012568. PMCID: PMC6464361.
Bobula, T., Buffa, R., Hermannov, M., Kohutov, L., Prochzkov, P., Vgnerov, H et al., 2017. A novel photopolymerizable derivative of hyaluronan for designed hydrogel formation. Carbohydrate Polymers, 161, 277-285.
Pepeliaev, S., Hrudkov, R., Jlkov, J., Pavlk, J., Smirnou, D., Cern, Z., et al., 2017. Colorimetric enzyme-coupled assay for hyaluronic acid determination in complex samples. European Polymer Journal, 94, 460-470.
Mirazee, I.S., "Biodegradable Nanofiber as Intrapocket Drug Delivery System for Treatment of Periodontitis," Abstract, Proceedings of the Hamadan Conference, Iranian Journal of Pharmaceutical Sciences, vol. 13, No. 4 (2017), pp. 62-63, Iranian Association of Pharmaceutical Scientists, Hamadan, Iran, Oct. 17-20, 2017, ISSN 1735-2444. Indexed in EMBASE (Elsevier Science Publishers).

\* cited by examiner

PERIODONTAL
POCKET

CROWN

HEALTHY PERIODONTIUM

UPPER TEXTILE UNIT
(slowly degrading)

GINGIVAL SULCUS
(SULCUS GINGIVALIS)

MIDDLE TEXTILE UNIT
(medium fast degrading)

PERIODONTAL LIGAMENT

RECEDING BONE

BOTTOM TEXTILE UNIT
(rapidly degrading)

ALVEOLAR BONE

DISSOLVED HYALURONAN

TOOTH ROOT

GUM

BASE OF
PERIODONTAL
POCKET

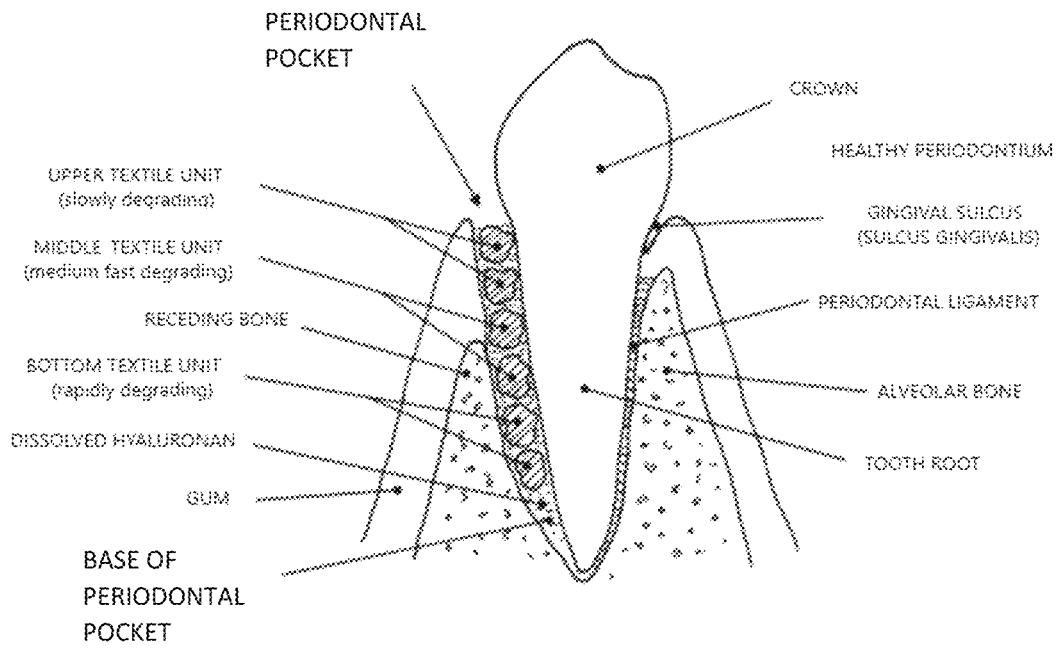

Fig. 1a

SLOWLY DEGRADING
UPPER UNIT WITH
SEALING FUNCTION

DECOMPOSING UNIT
IN THE MIDDLE PART
OF THE POCKET

NEWLY ESTABLISHED
PERIODONTAL
LIGAMENT AT THE
BOTTOM OF THE
POCKET

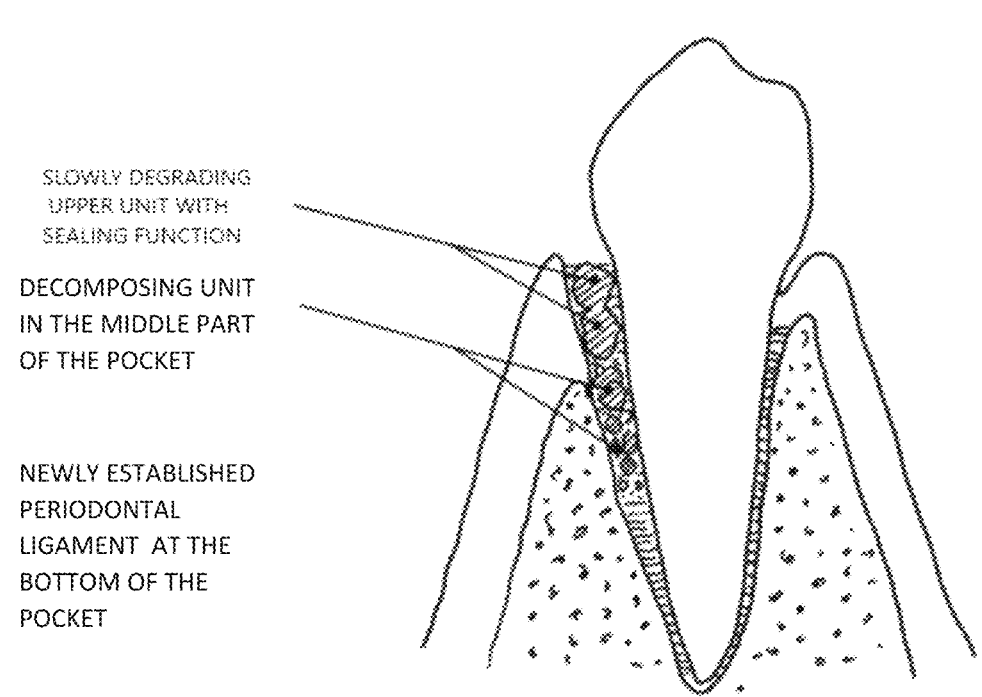

Fig. 1b

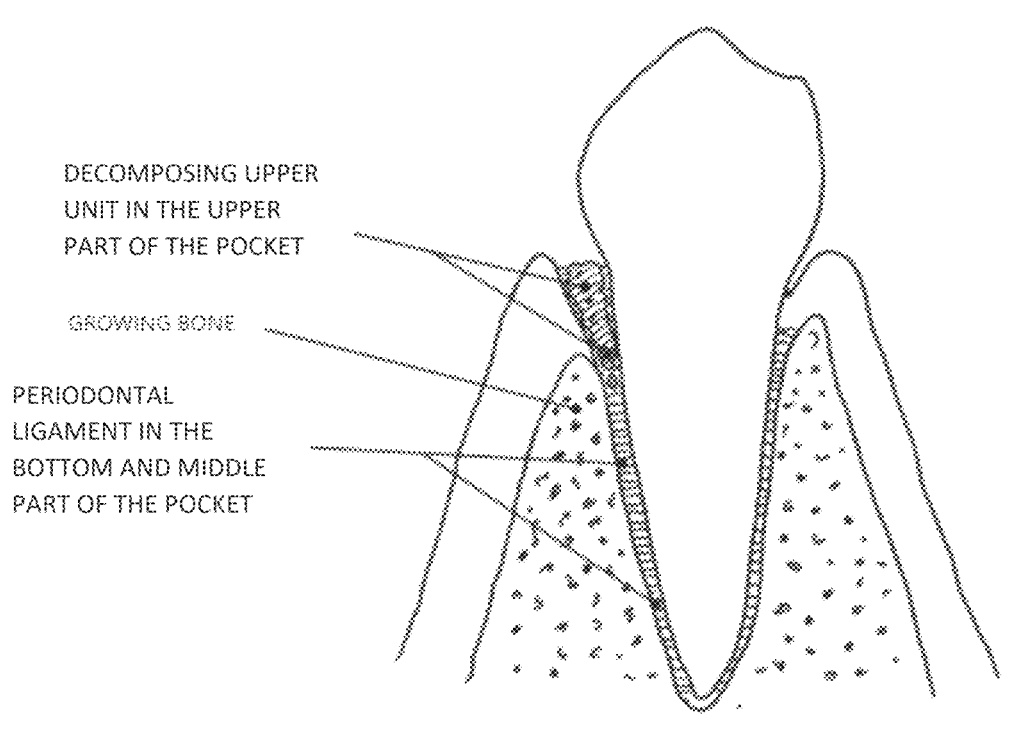
DECOMPOSING UPPER
UNIT IN THE UPPER
PART OF THE POCKET
GROWING BONE
PERIODONTAL
LIGAMENT IN THE
BOTTOM AND MIDDLE
PART OF THE POCKET
Fig. 1c
Fig. 1d
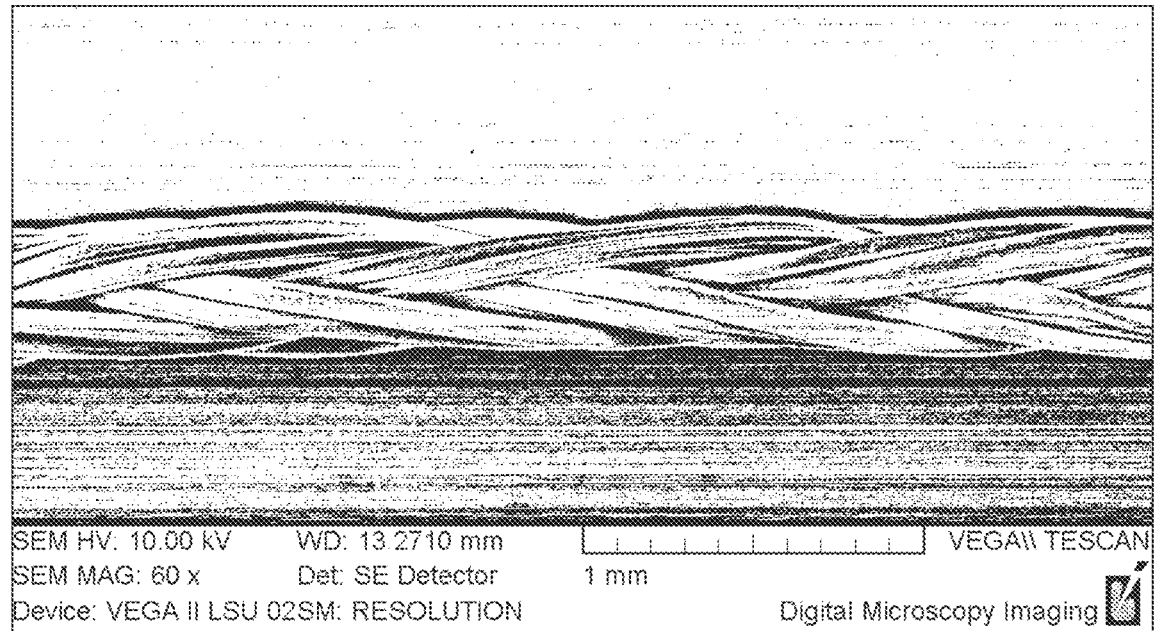
SEM HV: 10.00 kV        WD: 13.2710 mm        VEGA\\ TESCAN
SEM MAG: 60 x        Det: SE Detector        1 mm
Device: VEGA II LSU 02SM: RESOLUTION        Digital Microscopy Imaging Fig. 2a
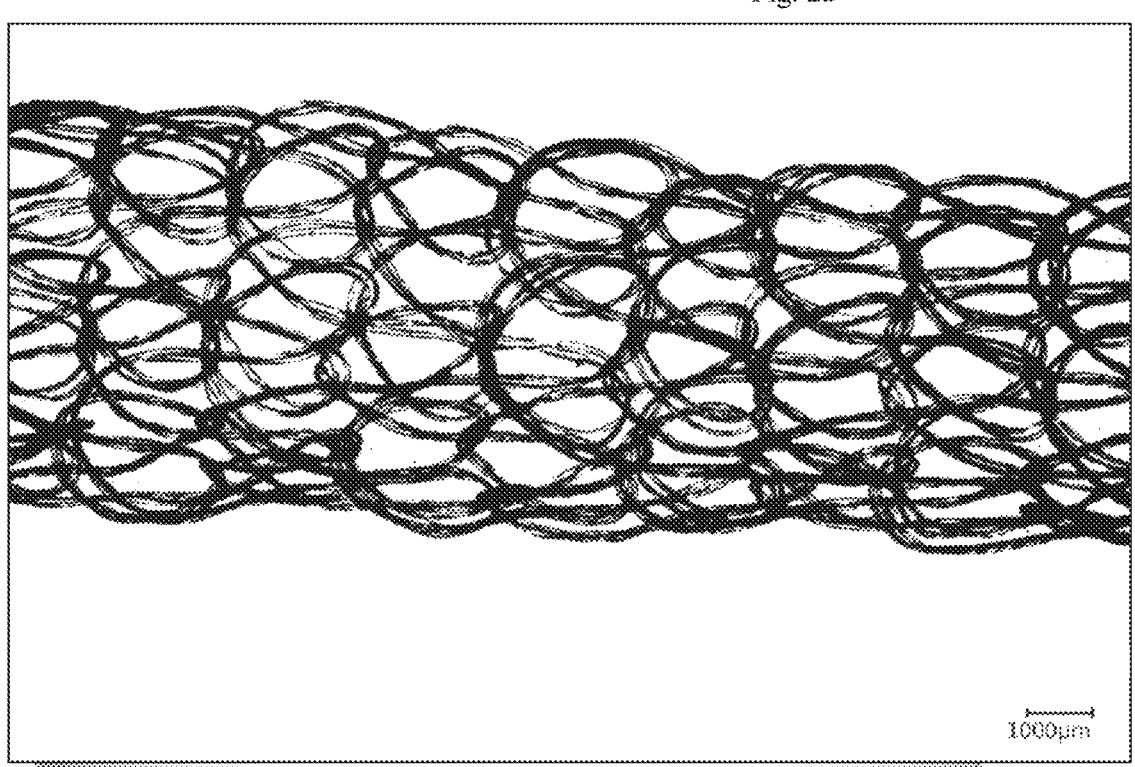
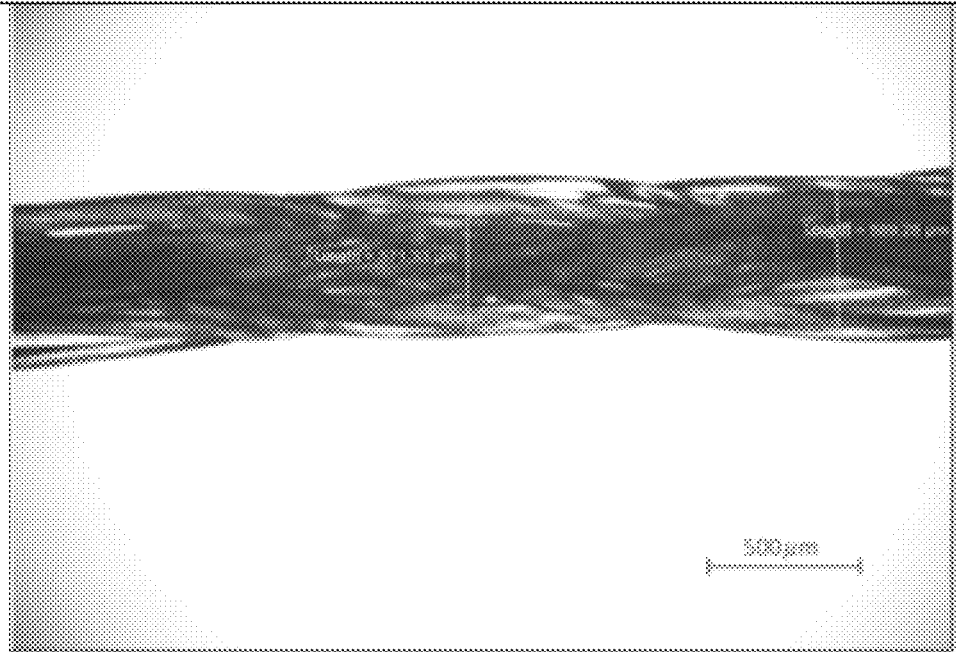
Fig. 3a

DENTAL PREPARATION COMPRISING FIBERS BASED ON HYALURONIC ACID WITH REGULATED BIODEGRADABILITY

CROSS-REFERENCE TO RELATED APPLICATIONS

This application is the National Stage of International Application No. PCT/CZ2021/05009, filed on 25 Jan. 2021, which claims priority to and all advantages of CZ Application No. PV2020-37, filed on 24 Jan. 2020, the contents of which are hereby incorporated by reference.

TECHNICAL FIELD

The present disclosure relates to dental preparation comprising at least one fiber of hyaluronic acid and at least one fiber of a non-polar derivative of hyaluronic acid, optionally further comprises antimicrobial agent. This preparation is intended to promote regeneration of tissues, especially in the field of dental medicine, as a support device in the treatment of periodontitis.

BACKGROUND

After dental caries, periodontitis is the second most common form of dental involvement. It affects the supportive tissue around the tooth. The development of periodontitis is usually preceded by gum inflammation (gingivitis). The pathology of the disease lies in the presence of calculus, upon which dental plaque accumulates, which gradually transforms into another calculus, and thus the layer of calculus gradually grows. The presence of dental plaque irritates immune system of the organism, which leads to development of inflammation reaction (redness and swelling of the gums, increased bleeding and last, but not least, the retreat of the bone, in which the teeth are anchored by periodontal fibers). The result is thus formation of so-called periodontal pocket (pocket between the dental root and gum/bone). A periodontal pocket up to cca 3.5 mm is considered physiological state, deeper pockets are manifest of disease and may reach up to 18 mm. When the disease worsens an infection by specific kinds of bacteria occurs, esp. *Porphyromonas gingivalis, Treponema denticola, Tannerella forsythensis, Prevotella intermedia, Fusobacterium nucleatum, Micromonas micros, Eikenella corrodens, Streptococcus sanguis* and *Aggregatibacter actinomycetemcomitans* (Listgarten 2004). The tooth suspension (attachment) apparatus is damaged by the action of bacteria, but also by the immune reaction of the organism, in response to infection. Said processes cause gradual release of the tooth and may lead up to irreversible loss. Currently, the treatment is based on removal of calculus from the tooth surface, and is often supported by administration of antibiotics [ATB](total administration is better than local). Although this procedure eliminates the cause of irritation, at the same time the periodontal pocket is not filled, and re-colonization of the root surface and treatment failure may occur. In addition, a repair rather than a regeneration occurs, i.e. the result of healing is not a condition as prior to the disease, but a condition that is satisfactory, however not full-fledged. Instead of re-forming the bone and fibers anchoring the tooth to the bone, the periodontal pocket is filled with epithelium from the oral cavity and so-called long sealing epithelium is formed. This is much more prone to recurrence of the disease.

In addition to the above standard treatment, there are alternative methods. One of them is the procedure of so-called controlled tissue regeneration, which allows the regeneration of the condition, but is always associated with the need of surgery and all the risks associated with it. A therapeutic preparation for controlled tissue regeneration is described, e.g. in U.S. Pat. No. 5,837,278. It is a collagen membrane, whose one side is fibrous and thus allows better cell growth, while the other side is smooth and inhibits cell adhesion. A variant is stated among the claims, in which the fibrous side of the collagen membrane is impregnated with hyaluronic acid. The disadvantage of the use of this membrane is the need of surgery.

It is important, for the treatment of periodontitis, to eliminate pathogenic microorganisms; that can be achieved by using antimicrobials (antibiotics, antiseptics) or by alternative ways, e.g. by ozone therapy or photodynamic therapy.

Materials called Local Drug Delivery Systems (LDDS) have been developed to support the treatment of periodontitis. These are carrier systems containing an antimicrobial agent, which are applied to the periodontal pocket, where the antimicrobial agent is gradually released over a longer period of time, usually in the order of days. Filling the periodontal pocket with antimicrobial-containing material prevents its recolonization by microbial pathogens, thus promoting the healing process. The advantage of these systems is in particular that, due to the local application, there is no contact with the internal environment, and thus it is possible to avoid health problems that could occur after contact with the active agent. Other advantages are that the active agent is not degraded during the first pass through the liver, a high therapeutic dose can be achieved locally, the agent is effective for a long time and the application is not invasive, is painless and easy. Disadvantages of LDDS include dose reduction due to relatively small space, risk of degradation by enzymes present in the mouth, and unsuitability for irritants. The basis of LDDS is usually a carrier polymeric material supplemented with an antimicrobial agent; the physical form can be, e.g. a gel, paste, powder, fiber, film or chip (Nair 2012).

Fibers

The concept of using fibers to treat periodontal diseases can be found in U.S. Pat. No. 4,175,326, which describes hollow fibers of a flexible semipermeable polymer, namely cellulose acetate, the cavity of which is filled with a drug (e.g. tetracycline) or an indicator for diagnosing and detecting dental diseases (e.g. acid-base indicator). The fibers are characterized by an outer diameter in the range of 100 to 300 $\mu$m and a wall thickness in the range of 5 to 100 $\mu$m. The rate of release of the active agent can be influenced by the permeability of the fiber wall. The fibers are inserted into the interdental space or are wrapped around the tooth. The disadvantage of these fibers is that they are not degradable and must be removed after the end of the therapy.

A therapeutic preparation based on ethylene vinyl acetate copolymer, intended for the treatment of the periodontal pocket, is described in the documents U.S. Pat. Nos. 4,892, 736 and 4,764,377. The fiber of a diameter of 0.1 to 1 mm contained tetracycline, which after insertion into the periodontal pocket was gradually released into the immediate vicinity, where it inhibited the growth of pathogenic bacteria. To limit the leaching of the active agent from the pocket, it was possible to use an additional system, e.g. in the form of a sealing ring threaded on the tooth. After treatment, the product had to be removed. Based on this concept, the commercial product Actisite was developed and launched in 1994 in the form of a fiber with a diameter of 0.5 mm and a length of 23 cm and containing 12.7 mg of tetracycline, which released from the fiber for 7 to 10 days. The fiber was fixed in the pocket with a cyanoacrylate adhesive (Nair 2012). Actisite has been withdrawn from the market despite its effectiveness in treating periodontitis. The reason was its non-degradability and the need to remove the fiber at the end of the therapy, which led to the disruption of the almost healed wound.

The following patent document WO 00/59469 describes modified fibers based on ethylene vinyl acetate copolymer with a diameter of 0.1 to 2 mm, containing 2.0 to 5.0 mg of clindamycin per 10 mm of fiber. The high antibacterial activity of the preparation is documented; however, the disadvantage remains that the carrier is a non-degradable polymer. An innovation is brought by patent WO 2010068940 A2, which used a combination of ethylene vinyl acetate fibers with biodegradable polymer fibers, which may be polyglycolides, polylactides, polylactone, poly(propylene fumarate), polyanhydrides, polyurethanes or polysaccharides. However, due to the persistence of ethylene vinyl acetate, the disadvantage of non-degradability of the preparation and the need to remove such a preparation from the wound was not completely eliminated.

U.S. Pat. No. 5,447,940 A discloses a composite material composed of a collagen matrix reinforced with a fibrous layer of a bioabsorbable polymer and containing a chemotherapeutic agent. The fibers can be formed by a copolymer based on lactic acid and glycolic acid or oxidized regenerated cellulose, and are processed into a woven, nonwoven or knitted mesh. The composite may contain a plasticizer, such as glycerol (up to 20 wt %) and an oil (1 to 20 wt %). The chemotherapeutic agent is selected from the group consisting of antibiotics, anesthetics, antiseptics and anti-inflammatory drugs, and is present in an amount of 0.1 to 5 wt %. This composite material is inserted in the form of strips 0.5 to 2 mm wide and 1 to 10 mm long into the periodontal pocket, where it absorbs body fluids, softens, swells and fills the pocket space within a few minutes. Subsequently, there is a gradual release of the chemotherapeutic agent. The material can stay here for up to 30 days; it is not necessary to remove it, as it is fully absorbable. However, the disadvantage of this solution is the use of several materials of different nature (collagen, polylactide or oxycellulose, plasticizer, oil). With collagen, as material of animal origin, there is a risk of transmission of infection (e.g. BSE—bovine spongiform encephalopathy). In the case of collagen, the possibility of regulating the rate of biodegradation is also very limited.

The commercial products Periodontal Plus AB and Perio-Col-TC from an Indian manufacturer Eucare Pharmaceuticals Private Ltd are also collagen-based. The biodegradable fibers of Periodontal Plus AB are made of type I collagen. 25 mg of collagen fibers contain 2 mg of tetracycline hydrochloride. It is not a continuous fiber as in the case of Actisite, but rather a bundle of fibers, which is moistened with saline before application and then inserted into the periodontal pocket, where they are gradually absorbed. Based on an in vitro study, the manufacturer claims that tetracycline is released from the fibers within 10 to 14 days. A clinical study (Kataria 2015) demonstrated the efficacy of the product against the *Aggregatibacter actinomycetemcomitans* strain. PerioCol-TC is composed of type I collagen fibers derived from fish, and also contains 2 mg of tetracycline hydrochloride per 25 mg of fibers. From the results of a clinical study (Gurha et al. 2016) it is clear, that after 45 days from the application of the fiber there was a significant reduction in the amount of *Porphyromonas gingivalis* bacteria compared to the control group. The disadvantage of these solutions is the animal origin of the collagen-based material (greater risk of contamination by impurities) and, also the need to moisten the fibers before insertion into the pocket, which prolongs the medical procedure. Another disadvantage is the very limited possibility of regulation of the rate of collagen biodegradation.

The drug-containing conjugated monofilaments are the subject of patent document US 2009/0155326 A1. The polymer for the preparation of fibers is of both biodegradable and non-biodegradable materials. Biodegradables have the function of drug carrier and non-biodegradables have only a supporting function. Copolymers of PLGA (lactic acid-glycolic acid copolymer), polycaprolactone, polydioxanone, Dexon, Vicryl and others are described as biodegradables. The fibers are prepared by the wet-spinning. The prepared fiber is then fed to a drug bath. The drug is selected from the groups: antibiotics, anti-inflammatory drugs, antimicrobial drugs, and others. The drug may be the same in each monofilament or different drugs may be used. The possible addition of plasticizers, polymers and cyclodextrins (cyclic oligosaccharides used for targeted drug distribution) is described. Resulting shape of the carrier system can be in the form of a tape, a tube, a thread, a braided thread, a knitted fabric. The described carrier systems are intended for the treatment of periodontitis. The disadvantage of this solution is the use of two functionally different types of fibrous materials—one with a reinforcing function and one with a drug carrier function. It is also the use of polymers and other chemicals that are non-degradable or of polymers and substances that are degradable but not inherent in the body.

Hyaluronic Acid

Hyaluronic acid (HA) is a natural polysaccharide that consists of repeating units of disaccharides composed of D-glucuronic acid and N-acetylglucosamine Its weight average molecular weight (Mw) can be up to $10^7$ g/mol. It usually occurs in the body in the form of sodium or other salts and is therefore also called hyaluronan or hyaluronate (HA). Most somatic cells (especially connective tissue cells) are able to produce hyaluronic acid. It is synthesized on their cell membrane and is directly secreted into the extracellular matrix, of which it is the major component in most tissues. It is found in large amounts in the vitreous, synovial fluid and skin. Hyaluronic acid was also identified in all periodontal tissues (non-mineralized and mineralized). Its primary role is to bind water to ensure the continuous transport of key substances between cells, to facilitate cell migration and to maintain tissue structure.

Hyaluronic acid also activates metalloproteinase inhibitors and thus prevents the destruction of tissues and thus contributes to their preservation. With its viscoelasticity, it helps to preserve space, protect surfaces, and slow down the penetration of viruses and bacteria. Thanks to its hygroscopicity and viscoelasticity, it also ensures lubrication and shock absorption. Hyaluronic acid also has anti-inflammatory, anti-edematous, antioxidant and bacteriostatic functions. Thanks to all these properties, biocompatibility, absence of undesirable side effects and biodegradability, it is used in a number of medical disciplines such as orthopedics, dermatology and ophthalmology.

It has been found that the need for hyaluronic acid for cell regeneration increases several times during gum damage, but it is formed in insufficient amounts. The application of hyaluronic acid in these pathologies restores the disturbed fluid balance in the periodontal tissue, thereby accelerating the healing processes and thus shortening the time required for the defect to heal and reducing the intensity of scarring.

Low concentrations of hyaluronic acid to some extent stimulate phagocytosis and metabolism, while extremely high concentrations have the opposite effect. Hyaluronic acid is also able to attract leukocytes from the blood. These cells then produce a variety of factors that stimulate fibroblasts and collagen production, which not only accelerates healing but also reduces the intensity of scarring. The basic role of hyaluronic acid in periodontal tissue is tissue regeneration, but it also has anti-inflammatory, anti-edematous and bacteriostatic effects (according to Pirnazar et al. (1999) on *Aggregatibacter actinomycetemcomitans, Prevotella oris* and *Staphylococcus aureus* strains commonly found in lesions in gums and periodontitis).

Mesa et al. (2002) studied the antiproliferative effect of hyaluronic acid, which was applied topically to 21 patients with periodontitis for 1 month. Their work shows that high molecular weight HA in patients with chronic periodontitis reduces cell proliferation of fibroblasts and lymphocytes, reduces the inflammatory process, and improves periodontal lesions.

Gontiya and Galgali (2012) observed in the treatment of gingivitis with hyaluronan that in most cases there was a decrease in the inflammatory infiltrate and at the same time hyaluronan helped to prevent the progression of periodontal lesions. Similar results can be found in the work of Piloni et al. (2011). The positive effect of hyaluronan in the treatment of plaque-induced gingivitis is also shown by the work of Jentsch et al. (2003).

Sapna and Vandana (2011) investigated the effect of a hyaluronan gel (Gengigel®) in the treatment of gingivitis. Clinical and histopathological changes were monitored in 28 patients with gingivitis, each with different treatments: mechanical, mechanical+ topically applied hyaluronan gel only, only topically applied hyaluronan gel, and as a last variant was topically and into the gingival sulcus (gingival) applied gel with hyaluronan. The results showed that the most effective method of treatment in this study was the combination of topical application of the gel with hyaluronic acid with its application to the sulcus *gingivalis*. Histopathologically, a reduction in inflammatory infiltrate was evident.

Utility Model CZ 28634U1 describes a dental preparation based on hyaluronan and octenidine dihydrochloride, intended for the treatment and prevention of dental complications, in particular alveolar ostitis, where it serves as a filling after tooth extraction. The dental preparation is in the form of a lyophilisate or gel and the weight ratio of hyaluronan to octenidine is in the range of 400:1 to 800:1 (0.125 to 0.25 wt %), which guarantees sufficient efficacy of the preparation against both gram-positive and gram-negative bacteria and yeast without impairing wound healing. Although it is a biodegradable material with an antimicrobial effect and is easy to handle, it would not be suitable for use as a periodontal pocket filler because it is a polymer that dissolves and absorbs very quickly and therefore only acts for a short time at the application site.

Patent document WO18158764 discloses a periodontal gel composition comprising a non-biodegradable temperature sensitive pharmaceutically acceptable polymer—in particular a polyalkylene oxide block copolymer, for example poloxamer—and low molecular weight hyaluronic acid (weight average molecular weight up to $5\times10^5$ g/mol). The ratio between the copolymer and HA is in the range of 20:1 to 50:1. The composition may additionally contain a therapeutic agent, e.g. an antibacterial agent, in particular octenidine, in an amount of 0.01 to 5 wt %. At normal ambient temperatures, the composition is liquid in nature and low in viscosity and can be injected into a periodontal pocket using a syringe and completely or partially fill it. After heating the composition to body temperature, solidification into a viscous gel occurs, which should adhere to the periodontal pocket, remain there, and slowly release the therapeutic agent. However, the test in the rabbit model described in Example 19 showed that the application of the gel to the periodontal pocket is very demanding due to its viscosity properties, the gel does not adhere sufficiently to the mucosa and soon after application it flows out. The disadvantage of this solution is the presence of a non-biodegradable component in the form of a thermosensitive polymer, which may pose health risks during tissue healing. In addition, organic solvents such as ethanol or phenoxyethanol must be used to dissolve the octenidine, which then becomes part of the gel composition applied to the pocket and can cause irritation of the inflamed tissue there. In the test described in Example 19, pus was present in the pockets of the mandible 48 hours after implantation of the gel.

There is a number of patents in which hyaluronic acid occurs only in the form of a surface layer or as an excipient. These include, for example, U.S. Pat. Nos. 5,837,278 or 6,720,009, where the active agent is used to treat oral injuries (tooth extraction, tooth implantation, treatment of periodontitis). However, in the therapeutic preparations according to these documents, hyaluronic acid or its derivative does not fulfill the carrier function or the function of the gradual-release active agent carrier, but only serves to promote tissue healing.

U.S. Pat. No. 5,622,707 discloses a biocompatible bioabsorbable composite membrane formed from hyaluronic acid esters and optionally alginic acid esters, which is suitable for promoting tissue regeneration. The membrane is formed by a reinforcing mesh, anchored and chemically bonded to the polymer matrix. Fibers based on hyaluronic acid esters, produced by solution spinning, are used for the mesh: The polymer dissolved in dimethyl sulfoxide is extruded by means of a multi-nozzle into a coagulation bath formed by ethanol. The result is a multifilament with a fineness of 150 to 400 denier (16.5 tex to 44 tex), consisting of 30 to 120 fibrils, which can then be twisted. From this multifilament, a knitted fabric with a thickness of 0.08 to 0.5 mm is made, on which a polymer solution is applied by the airbrush method, which again consists of esters of hyaluronic acid or alginic acid. A series of clinical experiments and experiments involving periodontal surgery have shown that the composite membrane shows very good mechanical resistance, biocompatibility and absorbability. However, the described membrane does not contain a soluble polymeric component, which is important for perfect filling of the periodontal pocket during therapy, nor an active agent with antimicrobial effect, the presence of which is crucial for preventing recolonization of affected tissues by microbial pathogens. In addition, the structure and shape of the membrane do not allow it to be layered into the periodontal pocket in the vertical direction.

The formation of filaments from hyaluronan or its derivatives is described in the following patents. It is again a solution spinning (hyaluronan does not have a real melting point and therefore cannot be spun from melt), so-called wet-spinning. In the case of WO2012089179 it is a spinning of hyaluronic acid and/or its metal compound. The aqueous polymer solution is extruded into a coagulation bath containing methanol or ethanol, formic acid or acetic acid and water. The resulting fiber with a fineness of 0.1 to 30 tex can be processed into a fabric. The disadvantage of these fibers and the fabrics made from them is that they dissolve very quickly in the aqueous medium and, when inserted into the periodontal pocket, would quickly float out. Without the presence of another type of fiber insoluble in an aqueous medium, the hyaluronic acid fibers in the pocket cannot perform the necessary sealing function. WO2014082610 A1 relates to oxidized hyaluronan fibers; in this case, the aqueous polymer solution is extruded into a coagulation bath containing lactic acid, ethanol or isopropanol and water. Although these fibers show reduced solubility in demineralized water due to surface crosslinking, they dissolve in phosphate buffered saline (PBS) for several hours, so that even these fibers cannot perform a sealing function in the pocket. Hydrophobized hyaluronan fibers are the subject of the invention described in WO2014082611 A1. These fibers are formed by a hyaluronan derivative which is modified preferably on the primary alcohol of N-acetyl-glucosamine and to a lesser extent on the secondary alcohols of glucuronic acid. Acylating agents are fatty acid anhydrides with a preferred chain length of $C_{11}$ to $C_{18}$. Derivatives may have varying degree of substitution. The polymer dissolved in a mixture of water and propan-2-ol is extruded into a coagulation bath containing an aqueous solution of an organic acid or a salt thereof. The resulting monofilament fibers have a diameter of 50 to 300 μm and their typical property is that they do not dissolve in water, but only swell. An in vitro test showed that even after derivatization and spinning, the polymer is biodegradable by enzymes. These fibers are therefore suitable for sealing the periodontal pocket, but because they do not dissolve, they cannot perfectly fill its inner space. The fibers according to the three above-mentioned patents, especially after processing into a knitted, woven or non-woven fabric, are directed to the field of medicine, but without a specific purpose. Their common disadvantage is that they do not contain an antimicrobial component that would prevent the recolonization of affected tissues by microbial pathogens.

Antimicrobial Agents

The success of periodontal therapy is closely correlated with the rate of reduction of subgingival pathogens (Quirynen et al. 2002), most often through antimicrobial agents—antibiotics or antiseptics, applied to the periodontal pocket. The duration of action of the active agent in the periodontal pocket must be sufficient to guarantee its antibiotic or antiseptic effect. However, there is a rapid exchange in the mouth, and thus an intensive leaching of these substances from the site of action. The binding of antimicrobials to serum proteins in the periodontal pocket can also be problematic.

Antimicrobials applied as adjunctive therapy after mechanical deep cleansing have a beneficial effect in terms of evaluation of the following clinical parameters: gingivitis, pocket depth, gingival adhesion or the need for surgery (Khattri et al. 2017).

An effective tool for selecting and evaluating a suitable antiseptic is the biocompatibility index (BI), a dimensionless number expressing the ratio of the cytotoxic and biocidal effect of a given antiseptic in vitro. If BI>1, the antiseptic has a higher biocidal effect than the cytotoxic effect at a given concentration, and wound healing is promoted. BI<1 have substances with relatively high cytotoxicity in a defined medium. In a comparative study of common antiseptics (Müller and Kramer 2008), octenidine had the most favorable BI value.

Octenidine, chlorhexidine and iodine-povidone are commonly used topical antiseptics in dentistry, adjuvants in the treatment of bacterial inflammatory diseases of the oral mucosa and gums. Of the topically applied antibiotics within LDDS, tetracycline or metronidazole are often represented.

Octenidine

Octenidine is a cationic surfactant, an antiseptic containing 2 pyridine nuclei linked by an aliphatic chain. Its most common form is the dihydrochloride salt. At physiological pH it is fully ionized (carries a positive charge), is stable in a wide pH range (1.6-12.2) and shows resistance to UV radiation. Due to its positive charge, octenidine interacts with the negatively charged surface structures of microorganisms (especially the lipid components of bacterial cell walls), thereby disrupting the function of their plasma membranes and causing autolysis of these cells. It is thus characterized by high antimicrobial activity without disrupting the cell epithelium of the healing wound. The cationic nature of octenidine (as well as chlorhexidine) minimizes its absorption through the skin or mucous membranes.

Octenidine soon established itself as an antiseptic component of mouthwashes. When comparing the effectiveness of mouthwashes (Welk et al. 2016), it was found that mouthwashes containing octenidine and chlorhexidine as an antiseptic reduced the amount of bacteria in the mouth significantly more than a preparation containing essential oils and compared to placebo.

Octenidine is a registered antiseptic with dermal and mucosal application, also as an antiseptic for wounds in the short term. However, application under pressure or into the tissue, as well as penetration into the bloodstream are contraindications. Drainage must therefore be provided for deep wounds. The resistance of microorganisms to octenidine is unknown (Hübner et al. 2010), although increased MIC values for *S. aureus* suggest a correlation between its use and increased tolerance (Hardy et al. 2018). Octenidine alone is non-toxic and does not cause allergic reactions (Kramer et al. 2018).

A preparation for healing superficial wounds, comprising a layer of a physiologically acceptable salt of hyaluronic acid and octenidine dihydrochloride, is the subject of utility model CZ 22394U1. The areal weight of the hyaluronan layer can be in the range of 5 to 20 $g/m^2$ and the amount of octenidine in the range of 10 to 40 $mg/m^2$, which corresponds to a concentration of 0.05 to 0.8 wt %. Antimicrobial efficacy was verified in in vitro and in vivo tests, and the positive effect of the product on wound closure in rats and minipigs was also confirmed. However due to the fact, that it was unmodified hyaluronan, which dissolves due to the exudate, an effect longer than two to three days cannot be expected.

If a prolonged antimicrobial effect is to be achieved with a therapeutic preparation, a gradual release of the active substance must be ensured. The release kinetics depend on the carrier material, its interactions with the active agent and the environment. Obermeier (2015) studied the antimicrobial effects of surgical sutures made of polyglycolic acid, on which a layer consisting of fatty acid and octenidine in various concentrations was applied. The release kinetics of octenidine from surface coating into phosphate-buffered saline (PBS) has been shown to be strongly dependent on the type of fatty acid in which the octenidine is anchored. While in the case of octenidine laurate 82 to 88% of the octenidine contained in the thread was released within 168 hours, in the case of octenidine palmitate it was only 5 to 33% (depending on the initial amount of octenidine on the thread). The antimicrobial effects of the threads were investigated against *Staphylococcus aureus*, with the measured width of the inhibition zone ranging from 1.6 to 1.9 mm and being stable for nine days (subsequently, the thread lost mechanical cohesion due to the humid environment on the agar).

9

Povidone-Iodide, PVP-I

Povidone-iodide (a complex of iodine and polyvinylpyrrolidone) has been replacing disinfectants based on iodine compounds in recent years. Iodoform or iodine tincture have been shown to be very irritating to the skin and are allergens. When povidone-iodide is used, iodine is gradually released from the complex and irritation can therefore be avoided (Lachapelle 2014).

In dental application, povidone iodide has been shown to be effective in the long-term treatment of periodontal pockets after deep brushing of teeth. The improvement was due to a more pronounced suppression of the growth of microorganisms in the periodontal pocket (Rams and Slots 1996). A positive effect (reduction in pocket depth) was achieved even after five weeks of povidone-iodide application as adjunctive therapy after mechanical cleaning (Hoang et al. 2003).

Chlorhexidine

Chlorhexidine is a synthetic basic biguanide used in concentrations of 0.5-4% alone or in lower concentrations in combination with other compounds, such as alcohols. At higher concentrations (from 2%) it is considered an irritant (Rams and Slots 1996). Chlorhexidine is used in a number of medical applications, e.g. for antiseptic coating of medical devices (Obermeier et al. 2014), as a skin antiseptic, or as an antiseptic in dentistry to prevent gingivitis and periodontitis, most commonly in the form of mouthwashes. For dental applications, there are products on the market with a chlorhexidine content in the range of 0.02%-0.3%, or higher concentration solutions for dilution. The optimal effect on the reduction of dental plaque and gingivitis appears to be a concentration of 0.12% (Varoni et al. 2012).

In the case of the use of chlorhexidine for the treatment of periodontitis, most authors agree that a single application of chlorhexidine to the periodontal pocket after mechanical cleansing does not bring significant clinical benefits. The improvement of the condition of the periodontal pockets was achieved only by repeated application of a 2% solution or gel of chlorhexidine after mechanical cleaning for 2-3 months. A further improvement was the application of an ethylcellulose film-based preparation with a sustained release of chlorhexidine, especially in combination with mechanical cleaning (Rams and Slots 1996).

Tetracycline

Tetracycline is a broad-spectrum antibiotic that prevents the destruction of collagen and bone in periodontitis by several mechanisms. On the one hand, it promotes tissue regeneration by increasing the activity of fibroblasts, at the same time reducing the activity of collagenases and having a significant bacteriostatic effect. (Golub et al. 1992) (Jain et al. 2008).

By applying a gel containing tetracycline hydrochloride to the periodontal pocket, it is possible to maintain a therapeutic dose of the antibiotic for 3-21 days. Application of a 10% solution (100 mg/ml) in a volume of 10-15 ml for 5 minutes resulted in an improvement compared to mechanical cleaning. This improvement was observable 6 months after treatment. The disadvantage of a 10% solution of tetracycline hydrochloride is its low pH, which can lead to tissue irritation or increased tooth sensitivity (Rams and Slots 1996).

The application of fibers containing tetracycline to the periodontal pocket is processed in another part of the text (Actisite fibers, Periodontal Plus AB, PerioCol-TC).

Metronidazole

Metronidazole (a derivative of nitroimidazole) is a synthetic antibiotic that interferes with the synthesis of bacterial DNA, causing cell death (da Rocha et al. 2015). As part of periodontal treatment, it is most often applied to the periodontal pocket in the form of a 25% gel.

Hyaluronan Chloramide

Patent document CZ308010 describes the invention of a chlorinated derivative of hyaluronic acid, also called hyaluronan chloramide, in which most of the hydrogen atoms of the amide group —NH—CO— are replaced by chlorine atoms NCl—CO—. Compositions containing hyaluronan chloramide are characterized by antimicrobial, antifungal and antiviral activity. The composition may, for example, be in the form of a solution or gel, but also of a solid substrate, including fiber, woven, knitted, crocheted or nonwoven. Application-wise, the patent is directed to the field of wound covers.

Current treatments for periodontitis (including therapies using LDDS in the form of a gel, paste, powder, fiber, film or chip containing an antimicrobial agent) lead to healing of the periodontal pocket from above. This creates a connecting epithelium between the tooth and the gums, but it is not sufficiently resistant to disease recurrence. Although periodontitis is a widespread disease affecting about a third of the population and new treatments and therapies are still being developed, no satisfactory solution to this problem has yet been found.

BRIEF SUMMARY

A biodegradable dental preparation, is provided. The dental preparation comprises:

(A) at least one water-soluble fiber made of hyaluronic acid or a physiologically acceptable salt thereof, and (B) at least one fiber made of a non-polar hyaluronic acid derivative according to general formula I:

wherein R is hydrogen, a physiologically acceptable metal cation, benzyl, or ethyl, and $R^1$ is H or an acyl group of formula —C(=O)C$_x$H$_y$, where x is an integer of from 5 to 17 and y is an integer of from 7 to 35 and C$_x$H$_y$ is a linear or branched, saturated or unsaturated hydrocarbon chain, wherein the non-polar hyaluronic acid derivative comprises at least one repeating unit comprising at least one substituent $R^1$ that is the acyl group or at least one substituent R that is benzyl or ethyl, provided that when the at least one substituent R is benzyl or ethyl, $R^1$ is H, and when the at least one substituent $R^1$ is the acyl group, R is hydrogen or a physiologically acceptable metal cation; and wherein the weight average molecular weight of the non-polar hyaluronic acid derivative of general formula I is from $1.0 \times 10^5$ to $1.2 \times 10^6$ g/mol.

A textile form of the biodegradable dental preparation is also provided, and comprises the preparation in the form of at least one textile unit selected from the group of fibers, a woven, knitted, non-woven or braided fabric, or a twisted bundle of fibers.

A method of ameliorating a periodontal disease is also provided. The method comprises administering the biodegradable dental preparation to a subject, and may be used to ameliorate or treat a periodontal disease selected from gingivitis, periodontitis, necrotizing ulcerative gingivitis, or treat a periodontal or oral mucosal injury with the biodegradable dental preparation.

BRIEF DESCRIPTION OF THE DRAWINGS

FIG. 1a-FIG. 1d illustrate phases of healing of a periodontal pocket by means of a dental preparation according to the present embodiments, with FIG. 1a illustrating textile units in the form of thread with different degradation rates inserted into the periodontal pocket, FIG. 1b illustrating formation of periodontal ligaments at the bottom of the pocket, FIG. 1c illustrating formation of periodontal ligaments in the middle part of the pocket, and growth of alveolar bone, and FIG. 1d illustrating a healed periodontium.

FIG. 2a-FIG. 2b illustrate dental preparations of the present embodiments prepared in the Examples, with FIG. 2a showing the dental preparation in the form of a braided thread of Example 18, and FIG. 2b showing the dental preparation in the form of a strip of fabric (warp knitted fabric) of Example 10.

FIG. 3a-FIG. 3c illustrate saliva swelling times of a dental preparation in the form of a braided thread prepared in the Example 12, with FIG. 3a showing the thread in dry state, FIG. 3b showing the thread after swelling in saliva at a time of 20 min., and FIG. 3c showing the thread after swelling in saliva at a time of 90 min.

DETAILED DESCRIPTION

Figure 3B:
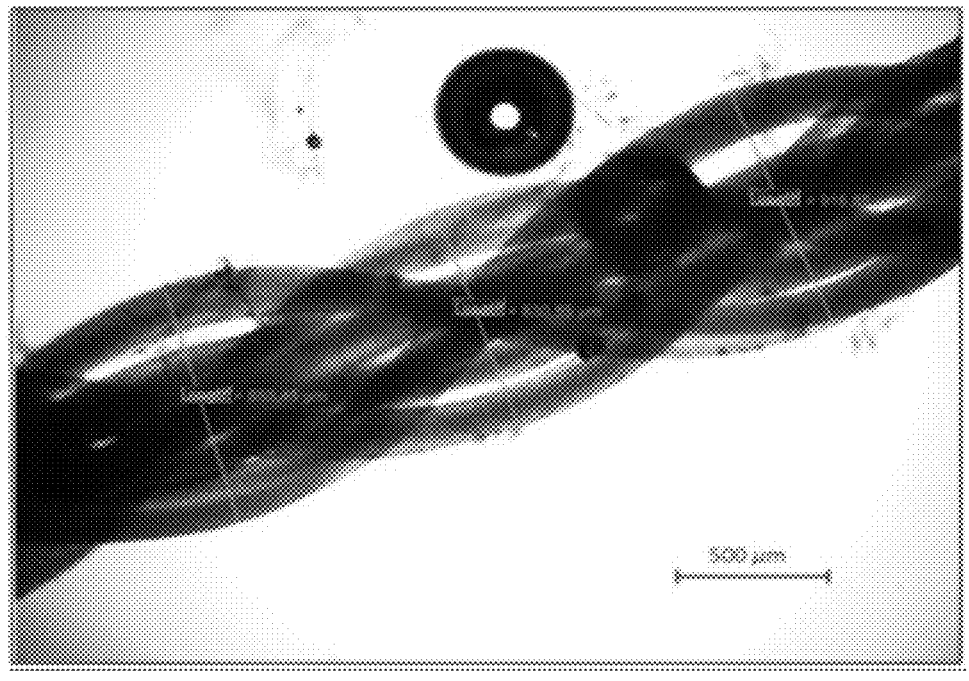

The following detailed description is merely exemplary in nature and is not intended to limit the disclosure or the application and uses of the subject matter as described herein. Furthermore, there is no intention to be bound by any theory presented in the preceding background or the following detailed description.

The disadvantages and limitations of the prior art are solved by the present embodiments of a biocompatible and biodegradable dental preparation with controllable biodegradability, comprising water-soluble hyaluronic acid (HA) fibers and fibers of a non-polar hyaluronic acid derivative, which may contain an antimicrobial agent, preferably an antiseptic. The biodegradable dental preparation according to the present embodiments is intended for use in the treatment and supportive treatment of periodontal diseases selected from the group comprising of gingivitis, periodontitis, necrotizing ulcerative gingivitis, preferably for the treatment of periodontitis, or treatment of periodontal and oral mucosal injuries caused by external physical forces, chemicals (e.g. acid burns, hydroxide burns), high or low temperatures, or injuries caused in connection with a medical procedure.

In a preferred embodiment, the dental preparation serves to fill the periodontal pocket, or mucosal wounds. In the case of the periodontal pocket, the application follows a standard treatment consisting of dental calculus removal from the surface of the tooth root. The product acts as a mechanical barrier against the entrance of impurities, prevents recolonization by bacterial pathogens, and creates a suitable environment for tissue regeneration—the connection of teeth and gums. The antimicrobial agent involved, preferably an antiseptic, in particular octenidine or a physiologically acceptable salt thereof such as octenidine dihydrochloride, contributes to the effect. The material is absorbable, it decomposes in the body within a few weeks.

The main advantage of the present embodiments is that in the treatment of periodontitis it creates the conditions for gradual healing from the bottom of the periodontal pocket, and thus for bone growth, and formation of a better connection between the tooth and the gums by means of periodontal ligaments. This is achieved by using several variants of the hyaluronan-based polymeric material, which differ in solubility in aqueous medium or in body fluids, respectively, and in the time of biodegradation (absorption).

The technical solution of the present embodiments lies in particular in a biodegradable dental preparation, the essence of which is that it contains at least one water-soluble fiber of hyaluronic acid or its physiologically acceptable salts and at least one fiber of a non-polar hyaluronic acid derivative according to general formula I (I)

where R is hydrogen, a physiologically acceptable metal cation, benzyl or ethyl, $R^1$ is H or $—C(\!=\!O)C_xH_y$, where x is an integer ranging from 5 to 17 and y is an integer ranging from 7 to 35 and $C_xH_y$ is linear or branched, a saturated or unsaturated chain, where in at least one repeating unit there is at least one substituent which is $—C(\!=\!O)C_xH_y$, or one of the substituents which is benzyl or ethyl, provided that when R is benzyl or ethyl, then $R^1$ is hydrogen, or a physiologically acceptable metal cation, and the weight average molecular weight of the non-polar hyaluronic acid derivative of general formula I is in the range of $1.0\times10^5$ to $1.2\times10^6$ g/mol.

Hyaluronic acid, or hyaluronan (HA) also means a physiologically acceptable salt thereof selected from the group comprising a physiologically acceptable metal cation, i.e. an alkali metal ion or an alkaline earth ion, preferably $Na^+$, $K^+$, $Ca^{2+}$, $Mg^{2+}$, more preferably $Na^+$.

The weight average molecular weight of hyaluronic acid or its physiologically acceptable salt contained in the fiber in the preparation according to the present embodiments is in the range of $1.0\times10^5$ to $1.2\times10^6$ g/mol, preferably in the range of $3.0\times10^5$ to $5.0\times10^5$ g/mol. The fibers made from HA according to the present embodiments are soluble in water, resp. in body fluids.

By non-polar HA derivative is meant a modified hyaluronan characterized by structural formula I as set forth above. The non-polar derivative is characterized by the presence of covalently attached hydrophobic groups—substituents on the hyaluronan chain. A non-polar derivative is also understood to mean a physiologically acceptable salt thereof selected from the group comprising of a physiologically acceptable metal cation, i.e. an alkali metal ion or an alkaline earth ion, preferably Na$^+$, K$^+$, Ca$^{2+}$, Mg$^{2+}$, more preferably Nat Preferably, its weight average molecular weight is in the range of $2.5\times10^5$ to $4.5\times10^5$ g/mol.

The non-polar HA derivative of general formula I can be divided into two groups according to the type of the substituent. The first group comprises of esters selected from the group of benzyl ester of hyaluronan and ethyl ester of hyaluronan. The preparation of these esters is described in U.S. Pat. No. 5,622,707. These variants of the non-polar derivative do not contain the acyl substituents—C(=O) C$_x$H$_y$. The second group, which represents a preferred embodiment, comprises of acylated derivatives. By acylated HA derivative is meant hyaluronan acylated with fatty acids on the hydroxyl groups of hyaluronan, the hyaluronan being modified preferably on the primary alcohol of N-acetyl-glucosamine and to a lesser extent on the secondary alcohols of glucuronic acid. The acylated —C(=O)C$_x$H$_y$ group, as defined above, is selected from the group comprising capronoyl (hexanoyl), capryloyl (octanoyl), caprinoyl (decanoyl), lauroyl (dodecanoyl), myristoyl (tetradecanoyl), palmitoyl (hexadecanoyl), stearoyl (octadecanoyl), oleoyl (octadec-9-enoyl), preferably lauroyl (dodecanoyl, —C(=O)C$_{11}$H$_{23}$) and palmitoyl (hexadecanoyl, —C(=O)C$_{15}$H$_{31}$). This variant of the non-polar derivative does not contain ethyl and benzyl substituents. Examples of the preparation of acylated derivatives are given in WO2014082611 A1.

The weight fraction of the substituent in the non-polar hyaluronic acid derivative of general formula I is in the range of 5 to 27 wt %, preferably 9 to 20 wt %. A value of 27 wt % corresponds to a degree of substitution of 100% for the benzyl ester HA. (Note: while the benzyl or ethyl groups are attached to the hyaluronan chain covalently by an ester bond, the hydrogen or metal is present in the form of a cation). The weight fraction of the substituent in the non-polar hyaluronic acid derivative of general formula I is based on the total weight of the non-polar hyaluronic acid derivative of general formula I.

The presence of hydrophobic groups (ethyl, benzyl or acyl) in the non-polar HA derivative limits the solubility in water of the fibers made from this derivative, or in body fluids, and determines the rate of fiber absorption—biodegradation at the site of implantation. The required degradation time of the dental preparation in the body is achieved by choosing a particular non-polar HA derivative, the amount of hydrophobic substituent on the HA polymer chain (by weight of bound benzyl, ethyl or acyl in the non-polar HA derivative of formula I) and a weight ratio of the hyaluronane fibers to the fibers made of non polar HA derivative according to general formula I contained in a dental preparation.

According to a preferred embodiment, the dental preparation comprises at least one antimicrobial substance selected from the group comprising an antiseptic or antibiotic or a combination thereof, preferably selected from the group comprising chlorhexidine, octenidine, its physiologically acceptable salt, povidone iodide, polyhexanide, triclosan, chloramine, tetracycline, metronidazole, chloramide derivative of hyaluronic acid according to general formula II (II)

where R is H, physiologically acceptable metal cation,
    R$^2$ is H or Cl,
wherein its weight average molecular weight (Mw) is in the range $2.0\times10^4$ to $6.0\times10^5$ g/mol and weight fraction of Cl is in the range 0.4 to 8.1 wt %.

According to another embodiment, the antimicrobial substance is contained in at least one fiber and/or on its surface. More preferably, the antimicrobial agent in the form of a coating on the fiber is present in an amount of 0.01 to 2.0 wt %, preferably 0.01 to 0.30 wt % more preferably 0.02 to 0.15 wt %. The weight fraction of the substituent in the chloramide derivative of HA of general formula II is based on the total weight of the chloramide derivative of hyaluronic acid of general formula II.

Preferably, the antiseptic is octenidine dihydrochloride. By deposition is meant an antimicrobial substance which is contained in the fiber and/or on its surface.

The chloramide derivative of HA of general formula II has a hydrogen of the amide group —NH—CO— substituted by a chlorine atom of the structural formula —NCl—CO—. The chloramide derivative according to the present embodiments is also understood to mean a physiologically acceptable salt thereof selected from the group comprising a physiologically acceptable metal cation, i.e. an alkali metal ion or an alkaline earth ion, preferably Na$^+$, K$^+$, Ca$^{2+}$, Mg$^{2+}$, more preferably Na$^+$. The chloramide derivative of general formula II above may be present in the dental preparation according to the present embodiments in the form of a fiber.

According to another embodiment, the chloramide derivative of HA according to formula II is present in the preparation in the form of at least one chloramide fiber from the chloramide derivative of HA according to formula II or in the form of a mixed chloramide fiber comprising chloramide derivative of HA according to formula II and HA or chloramide hyaluronic acid derivative of general formula II and a non-polar HA derivative of general formula I, preferably lauroyl hyaluronan or palmitoyl hyaluronan.

Preferably, the Mw of the chloramide derivative of HA of general formula II in the chloramide fiber contained in the preparation according to the present embodiments is in the range of $1.0\times10^5$ to $6.0\times10^5$ g/mol, preferably $1.5\times10^5$ to $5.5\times10^5$ g/mol, and in the mixed chloramide fiber contained in the preparation according to the present embodiments in the range $2.0\times10^4$ to $5.0\times10^5$ g/mol, preferably $3.0\times10^5$ to $4.5\times10^5$ g/mol.

According to yet another embodiment, the weight fraction Cl of the chloramide derivative of HA according to general formula II in the chloramide fiber contained in the preparation according to the present embodiments is in the range of 0.4 to 4.7 wt %, (DS 5 to 55%), preferably 3.4 to 4.7 wt %, (DS 40 to 55%) and in the mixed chloramide fiber contained in the preparation according to the invention, in the range of 4.2 to 8.1 wt %, (DS 40 to 100%), preferably 6.6 to 8.1 wt %, (DS 80 to 100%), wherein the weight ratio between the chloramide HA derivative of general formula II and the HA or the chloramide HA derivative of general formula II and the non-polar HA derivative of general formula I in the mixed chloramide fiber is in the range of 10:90 to 70:30, preferably 40:60 to 60:40.

In the case of a dental preparation according to the present embodiments comprising at least one chloramide fiber or a mixed chloramide fiber, the chloramide derivative of HA according to general formula II is considered to be an antimicrobial agent. Its weight fraction in the textile unit of the dental preparation is in the range of 5 to 55 wt %, preferably 20 to 30 wt % (definition of textile unit is given below). Weight fraction of $P_{CT}$ [wt %] of the chloramide derivative in the textile unit of the dental preparation is given by $$P_{CT}=P_{CI}\times P_{CV}/100,$$

where $P_{CI}$ [wt %] is the weight fraction of chloramide derivative HA in the fiber and $P_{CV}$ [wt %] is the weight fraction of chloramide fibers or mixed chloramide fibers in the textile unit.

According to yet another embodiment, the dental preparation is in the form of at least one textile unit comprising a combination of at least one HA fiber or a physiologically acceptable salt thereof, and at least one fiber of non-polar HA derivative according to general formula I as defined above, wherein it is in the form of at least one textile unit selected from the group comprising fibers, woven, knitted, non-woven or braided fabric, preferably a strip of fabric, further a thread in the form of a fiber bundle, a twisted fiber bundle, preferably in the form of a braided thread or a tube.

By textile unit is meant a thread, fabric or even a fiber in the case where the preparation according to the present embodiments contains more than one textile unit. The fiber can be in the form of a so-called endless fiber—monofilament or multifilament, or in the form of a staple fiber, i.e. short fiber with a length ranging from 1 to 150 mm. The fineness of the fibers is in the range of 3 to 40 tex, preferably 6 to 11 tex. By thread is meant a length formed by endless or staple fibers and is made by textile processes, which may include joining, braiding, twisting, plying, knitting, preferably braiding.

It can be a bundle of parallel-oriented fibers, a twisted bundle of fibers, a knitted chain, preferably a braided thread. According to yet another embodiment, the diameter of the thread in the dry state is in the range of 0.1 to 3 mm, preferably 0.3 to 1 mm By fabric is meant a sheet or tubular structure comprising the fibers of the present embodiments; it may be a woven, non-woven, knitted or plaited fabric. In a preferred embodiment, the fabric in dry state is in the form of a narrow strip of woven, nonwoven, plaited or knitted fabric. According to yet another embodiment, the width of the strip of fabric in dry state is in the range of 0.5 to 10 mm.

An advantage of the dental preparation according to the present embodiments in the form of a thread or fabric is the possibility of combining several types of fibers, i.e. fibers of different HA-based polymers according to the present embodiments (HA, non-polar HA derivative according to general formula I, chloramide HA derivative according to general formula II) within one textile unit, the weight fraction of the individual fiber types in the thread or fabric being different. When the textile unit within the set of textile units is in the form of a fiber, it contains hyaluronic acid or a non-polar HA derivative of general formula I, or a chloramide HA derivative of general formula II, or a combination of HA and a chloramide HA derivative of general formula II, or a combination of a non—polar HA derivative of general formula I and a chloramide HA derivative of general formula II).

The dental preparation contains one or more textile units. The textile unit is a form of a dental preparation according to the present embodiments, comprising a combination of at least one fiber of HA and at least one fiber of a non-polar derivative of HA according to general formula I.

If the dental preparation according to the present embodiments comprises a set of textile units (i.e. two or more textile units) one of the textile units may comprise a fiber, fabric or thread of HA, or a fiber, fabric or thread of a non-polar HA derivative of general formula I. Thus, a textile unit is a fiber, thread or fabric.

The dental preparation according to the present embodiments is intended to be inserted into a specific area of the affected tissue. In the case of periodontitis, textile units are inserted into the periodontal pocket, where they act as a mechanical barrier and prevent its recolonization by microbial pathogens. Size or length of the textile unit and its adjustment is chosen so that it can be easily manipulated during treatment. It can be, for example, a winding of a thread or a strip of fabric on a spool, the length being several tens of centimeters to several tens of meters, or the textile unit is cut to a length of millimeters to tens of centimeters and is stored in a suitable package. Prior to application, the length of the textile unit is adapted to the dimensions and character of the periodontal pocket; it is usually 0.1 to 20 cm long. The textile unit, preferably a thread or strip of fabric, can either be wrapped several times around the root of the tooth, or it is pre-cut into shorter sections of about 0.5 to 3 cm and inserted from the front or back or side of the tooth so as to best fill the pocket.

In the simplest embodiment, the dental preparation comprises one textile unit, which is a fabric or a thread, wherein the weight ratio of HA fibers or its physiologically acceptable salt to non-polar HA derivatives of general formula I contained in the textile unit is 5:95 to 95:5, preferably 10:90 to 55:45, more preferably 20:80 to 40:60. Preferably, the weight fraction of the substituent on the non-polar HA derivative of general formula I is in the range of 14.0 to 20.0 wt %, preferably 15.5 to 18.0 wt %. In a preferred embodiment, this textile unit is in the form of a braided thread or a strip of fabric and further comprises an antimicrobial agent, preferably octenidine dihydrochloride. The textile unit of required length is gradually inserted into the entire area of the pocket from the bottom to the upper edge. The fibers of the non-polar derivative according to the present embodiments swell, thus ensuring in particular the sealing of the pocket. However, hyaluronan fibers also play an important role, as they are soluble in an aqueous medium and, when in contact with body fluids, turn into a viscous solution that easily fills the remaining space inside the pocket. Thus, the viscous HA solution reaches the bottom of the pocket, where suitable conditions for healing are created, and thus the healing process is started from the bottom of the pocket. The antimicrobial agent contained in the dental preparation kills microorganisms in the periodontal pocket immediately after treatment and prevents recolonization of the pocket in the following days to weeks, or even reduces the deposition of dental plaque in the neck area of the tooth.

In another preferred embodiment, the dental preparation is in the form of a set of at least two textile units. Preferably, at least one textile unit comprises a fiber, fibers, fabric or thread, provided that the preparation comprises at least one water-soluble fiber of HA or a physiologically acceptable salt thereof and at least one fiber of a non-polar HA derivative of general formula I. The different material composition of the textile units in the set is also advantageous. Thanks to this, it is possible to achieve a graded rate of biodegradation, or absorption in the periodontal pocket, thus further promoting the healing process from the bottom of the pocket compared to the case where the dental preparation contains only one textile unit.

The set as a whole always contains both HA fibers and non-polar HA derivative fibers according to the invention. The set may contain two to five, preferably three textile units. The location of the individual textile units is evident from FIG. 1a). The textile unit, which is intended to be placed on the bottom of the pocket, is referred to as the bottom, and is characterized by rapid biodegradation in the organism; the unit intended for the central region of the pocket is referred to as the middle, and is characterized by medium-rapid biodegradation in the organism; the unit intended for the upper region of the pocket is referred to as the upper, and is characterized by slow biodegradation in the organism. The set may contain only the bottom and upper textile units, or may contain, in addition to the bottom and upper textile units, one to three middle textile units with different material composition and degradation rate. The textile unit that is part of the set comprises one or more types of fibers according to the invention. It may include a HA fiber or a non-polar HA derivative fiber, or a chloramide fiber, or a mixed chloramide fiber, or a combination thereof.

According to a preferred embodiment, the dental preparation is in the form of a thread or a strip of fabric and serves to fill the periodontal pocket after a standard treatment which comprises removing calculus from the tooth root surface, and removing infected hard dental tissues. In therapy, a dental preparation in the form of a set of textile units can advantageously be used, which differ from one another in particular in terms of degradation time. The bottom textile unit, which degrades the fastest, is inserted first into the periodontal pocket and is thus inserted all the way to the bottom of the pocket. Furthermore, the textile units are inserted into the periodontal pocket according to the gradually increasing time required for degradation. The middle textile unit (or units) is thus inserted into the middle area of the pocket, and the upper textile unit, i.e. the unit with the longest degradation time, is inserted into the upper area at the entrance to the periodontal pocket (see FIG. 1a). Gradual transformation of the dental preparation, or of fibers forming it, on the gel or on the viscous solution allows even filling of the entire periodontal pocket and at the same time ensures sufficient plasticity of the material, which prevents premature release of the dental agent material from the periodontal pocket during chewing and tooth movement in the bed. The preparation is clamped between the tooth and the gums, so pressure acts on it and it responds to it by continuously changing its shape and size. It is advantageous if there is a slight expansion of the material during the conversion of the fibers forming the dental preparation into a gel. Gradual conversion of the fiber into a viscous solution (in the case of hyaluronan) or into a gel (in the case of a non-polar HA derivative of general formula I) further allows continuous release of the disinfectant or antimicrobial component of the preparation. The antimicrobial is first released from the hyaluronan fibers, which are soluble in the aqueous medium. In a preferred embodiment of the dental preparation according to the invention, the antimicrobial agent is the antiseptic octenidine, which does not bind to hyaluronan and can therefore be released rapidly, while octenidine is attached to the hydrophobic groups of the nonpolar HA derivative of general formula I by non-covalent bonds. Thus, the release of octenidine occurs gradually and over a period of time in the order of days to weeks. The release kinetics depends on the type and amount of substituent—ethyl, benzyl or acyl. The fibers of the non-polar HA derivative of general formula I swell on contact with body fluids, but retain cohesiveness. The upper textile unit prevents the recolonization of the periodontal pocket by microorganisms from the oral cavity and further prevents the growth of epithelium present on the mucosa of the gingival process, which would lead to the formation of so-called long sealing epithelium, which prevents the formation of new periodontal fibers and does not enable a full regeneration of the periodontium. On the contrary, the rapidly degrading bottom textile unit at the bottom of the periodontal pocket frees up space immediately after its application, where it will be possible to regenerate periodontal ligaments with gradual apposition of the bone of the alveolar ridge of the jaw bone. This procedure creates conditions for the regeneration of the periodontium and the possibility of healing the so-called ad integrum.

The course of biodegradation of the dental preparation and the phase of the healing process from the bottom of the pocket are schematically shown in FIGS. 1a)-1d). FIG. 1a) shows the periodontal pocket on the left shortly after the dental preparation according to the present embodiments has been inserted in the form of a set containing three textile units in the form of a thread. The fibers formed by the non-polar HA derivative of general formula I are swollen and have the character of a compact gel. The hyaluronan fibers are already dissolved in the body fluids and the resulting viscous solution fills the remaining areas of the pocket, including the space at its bottom. Within a few hours to days, the bottom textile unit disintegrates and is absorbed, and at the bottom of the pocket, a connection is formed between the tooth and the gums by means of periodontal ligaments (see FIG. 1b). The middle textile unit, which degrades more slowly than the bottom unit, acts as a barrier in the first days after implantation, preventing the formation of a lower-quality connection between the tooth and the gums. In this phase, bone growth occurs, which is a prerequisite for the regeneration of periodontal ligaments. These are formed only after a certain time interval when the bottom area of the pocket is healed (see FIG. 1c). The upper textile unit, degrading the slowest, seals the entrance to the pocket and thus prevents the penetration of impurities into the periodontal pocket and at the same time ensures that the tooth-gum connection in the upper part of the pocket is formed only after regeneration of periodontal ligaments in the bottom and middle part of the pocket. The result of the healing process with the aid of a dental preparation is shown in FIG. 1d). The bone is grown, and in the whole area of the original pocket a full-fledged connection of the bone and the tooth is created by means of regenerated periodontal ligaments. The described concept, based on healing from the bottom of the pocket, is completely new compared to the prior art.

According to a preferred embodiment, the dental preparation takes the form of a set of at least two textile units. To achieve the required effect of the dental preparation in the form of a set, it is necessary to create textile units (bottom, middle and upper), which differ in the rate of degradation in the body. Different rates of degradation can be achieved in several ways, which comprise:
  a) Choice of polymer: The textile unit containing HA dissolves very quickly in body fluids and degrades, while the degradation of the textile unit containing the non-polar HA derivative according to general formula I is slower.
  b) Choice of the type of non-polar HA derivative: The chemical structure of the substituent (hydrophobic group) affects the degree of swelling and the rate of degradation of the fiber and thus of the textile unit. The substituent of the non-polar hyaluronic acid derivative of general formula I is selected from the group comprising capronoyl, capryloyl, caprinoyl, lauroyl, myristoyl, palmitoyl, stearoyl, oleoyl, ethyl, benzyl, preferably lauroyl and palmitoyl.

c) Weight fraction of substituent: The amount of acyl, benzyl or ethyl bound to hyaluronan has a fundamental effect on the physical properties of the fibers. As the amount of hydrophobic groups attached to the HA chain increases, the swelling and rate of fiber degradation decreases. A textile unit containing fibers of a non-polar HA derivative of general formula I with a higher weight fraction of a substituent degrades more slowly, a unit containing fibers with a lower weight fraction of a substituent degrades faster.

d) Weight ratio of fibers in the textile unit: The more soluble HA fibers contained in the textile unit, the faster it will degrade; conversely, the more fibers of the non-polar HA derivative of general formula I contained in the textile unit, the slower the degradation will be.

The rate of fiber degradation, or degradation of threads or textiles, is related to the swelling of the fibers—strongly swelling fibers show a higher rate of degradation. The swelling of the various thread variants formed by 16 fibers is documented in Example 14, in FIG. 3a-FIG. 3c and in FIG. 6. The dry thread diameter is similar for all variants. However, it can be seen that threads containing palmitoyl HA fibers swell less in saliva than threads containing lauroyl HA fibers. In threads containing lauroyl HA fibers can be further observed that at the same fiber weight ratio, threads that contain fibers with lower fraction of substituent swell more, and threads that contain fibers with higher fraction of substituent swell less, because they are more hydrophobic. As the proportion of hyaluronan fibers increases, the diameter of the wetted thread decreases; the reason is that the HA dissolves. The thread then consists only of swollen lauroyl fibers, the amount of fibers being different for individual variants with different weight ratios, which is reflected in the different diameter of the swollen thread.

Overview of the Design of Sets of Textile Units in a Dental Preparation According to the Invention:

According to yet another embodiment, the set of textile units of the preparation comprises as upper textile unit a fiber, fibers, fabric or thread comprising at least one fiber of a non-polar HA derivative of general formula I, wherein the weight fraction of the substituent on the non-polar HA derivative of general formula I is in the range of 14 to 20 wt %, preferably 15.5 to 18 wt % and as a bottom textile unit a fiber, fibers, fabric or thread containing at least one fiber of hyaluronic acid or a physiologically acceptable salt thereof (see Table 1).

Preferably, the textile units contain an antimicrobial agent, more preferably octenidine or octenidine dihydrochloride.

TABLE 1

| Textile unit | Material composition | Mass fraction of substituent in non-polar derivative of HA [wt %] | |
| | | Range | Preferable range |
| --- | --- | --- | --- |
| Upper | Nonpolar derivative of HA | 14.0 to 20.0 | 15.5 to 18.0 |
| Bottom | HA | — | — |

According to yet another embodiment, the set of textile units of the composition comprises as upper textile unit a fiber, fibers, fabric or thread comprising at least one fiber of a non-polar HA derivative of general formula I, wherein the weight fraction of the substituent on the non-polar HA derivative of general formula I is in the range 14 to 20 wt %, preferably 15.5 to 18 wt %, as a middle textile unit a fiber, fabric or thread comprising at least one fiber of hyaluronic acid or a physiologically acceptable salt thereof and at least one fiber of non-polar HA derivative of general formula I, the weight fraction of the substituent on the non-polar HA derivative of general formula I is in the range of 14 to 20 wt %, preferably 15.5 to 18 wt %, and as a bottom textile unit a fiber, fibers, fabric or thread comprising at least one fiber of HA or a physiologically acceptable salt thereof. Preferably, the weight ratio of fibers of HA or a physiologically acceptable salt thereof to the fibers of non-polar HA derivative of general formula I contained in the middle textile unit is 20:80 to 80:20, preferably 40:60 to 60:40 (see Table 2). The middle and upper textile units preferably contain the same type of non-polar HA derivative according to general formula I, preferably lauroyl HA or palmitoyl HA, the weight fraction of the substituent in the non-polar HA derivative being the same in both units. Preferably, the textile units contain an antimicrobial agent, more preferably octenidine or octenidine dihydrochloride.

TABLE 2

| Textile unit | Material composition | Weight fraction of substituent in non-polar derivative of HA [wt %] | | Weight ratio HA:non-polar derivative of HA | |
| | | Range | Preferable range | Range | Preferable range |
| --- | --- | --- | --- | --- | --- |
| Upper | Nonpolar derivative of HA | 14.0 to 20.0 | 15.5 to 18.0 | — | — |
| Middle | HA + non-polar derivative of HA | 14.0 to 20.0 | 15.5 to 18.0 | 20:80 to 80:20 | 40:60 to 60:40 |
| Bottom | HA | — | — | — | — |

According to yet another embodiment, the set of textile units of the composition comprises as upper textile unit a fiber, fabric or thread comprising at least one fiber of hyaluronic acid or a physiologically acceptable salt thereof and at least one fiber of non-polar HA derivative according to general formula I. The mass fraction of the non-polar HA derivative of general formula I is in the range of 14 to 20 wt %, preferably 15.5 to 18 wt %, and as a bottom textile unit a fabric or thread comprising at least one fiber of HA or a physiologically acceptable salt thereof and at least one fiber of non-polar hyaluronic acid derivative of general formula I, the weight fraction of the substituent on the non-polar HA derivative of general formula I being in the range 14 to 20 wt %, preferably 15.5 to 18.0 wt %. Preferably, the weight ratio of the fibers of HA or a physiologically acceptable salt thereof to the fibers of non-polar HA derivative of general formula I contained in the upper textile unit is 5:95 to 60:40, preferably 20:80 to 55:45, and the weight ratio of fibers of HA or a physiologically acceptable salt thereof relative to the fibers of non-polar HA derivative of general formula I contained in the bottom textile unit is 50:50 to 95:5, preferably 60:40 to 80:20 (see Table 3).

The textile units preferably contain the same type of non-polar derivative, preferably lauroyl HA or palmitoyl HA, the weight fraction of the substituent in the non-polar HA derivative being the same in both units. The textile units differ from each other in the weight ratio of the fibers contained. Preferably, the textile units contain an antimicrobial agent, more preferably octenidine or octenidine dihydrochloride.

TABLE 3

| Textile unit | Material composition | Weight fraction of substituent in non-polar derivative of HA [wt %] | | Weight ratio HA:non-polar derivative of HA | |
|---|---|---|---|---|---|
| | | Range | Preferable range | Range | Preferable range |
| Upper | HA + Non-polar derivative of HA | 14.0 to 20.0 | 15.5 to 18.0 | 5:95 to 60:40 | 20:80 to 55:45 |
| Bottom | HA + non-polar derivative of HA | 14.0 to 20.0 | 15.5 to 18.0 | 50:50 to 95:5 | 60:40 to 80:20 |

According to yet another embodiment, the set of textile units of the composition comprises as upper textile unit a fiber, fabric or thread comprising at least one fiber of HA or a physiologically acceptable salt thereof and at least one fiber of non-polar hyaluronic acid derivative of general formula I, wherein the weight fraction of the substituent on non-polar hyaluronic acid derivative of general formula I is in the range of 14.0 to 20 wt %, preferably 15.5 to 18 wt %, as a middle textile unit a fiber, fabric or thread comprising at least one fiber of HA or a physiologically acceptable salt thereof and at least one fiber of non-polar HA derivative of general formula I, wherein the weight fraction of the substituent on the non-polar HA derivative of general formula I is in the range of 14.0 to 20.0 wt %, preferably 15.5 to 18.0 wt % and as a bottom textile unit a fiber, fabric or thread comprising at least one fiber of hyaluronic acid or a physiologically acceptable salt thereof and at least one fiber of non-polar hyaluronic acid derivative of general formula I, the mass fraction of the substituent on the non-polar hyaluronic acid derivative of formula I is in the range of 14.0 to 20.0 wt %, preferably 15.5 to 18.0 wt %. Preferably, the weight ratio of the fibers of HA or a physiologically acceptable salt thereof to the non-polar HA derivative fibers of general formula I contained in the upper textile unit is 5:95 to 50:50, preferably 20:80 to 40:60, furthermore, the weight ratio of fibers of HA or a physiologically acceptable salt thereof to the fibers of non-polar HA derivative of general formula I contained in the middle textile unit is 30:70 to 70:30, preferably 40:60 to 60:40, and the weight ratio of the fibers of HA or a physiologically acceptable salt thereof to the fibers of the non-polar HA derivative of general formula I contained in the bottom textile unit is 50:50 to 95:5, preferably 60:40 to 80:20 (see Table 4).

The textile units preferably contain the same type of non-polar derivative, preferably lauroyl HA or palmitoyl HA, the weight fraction of the substituent in the non-polar HA derivative being the same in all units. The textile units differ from each other in the weight ratio of the fibers contained. Preferably, the textile units contain an antimicrobial agent, more preferably octenidine or octenidine dihydrochloride.

TABLE 4

| Textile unit | Material composition | Weight fraction of substituent in non-polar derivative of HA [wt %] | | Weight ratio HA:non-polar derivative of HA | |
|---|---|---|---|---|---|
| | | Range | Preferable range | Range | Preferable range |
| Upper | HA + non-polar derivative of HA | 14.0 to 20.0 | 15.5 to 18.0 | 5:95 to 50:50 | 20:80 to 40:60 |
| Middle | HA + non-polar derivative of HA | 14.0 to 20.0 | 15.5 to 18.0 | 30:70 to 70:30 | 40:60 to 60:40 |
| Bottom | HA + non-polar derivative of HA | 14.0 to 20.0 | 15.5 to 18.0 | 50:50 to 95:5 | 60:40 to 80:20 |

According to yet another embodiment, the set of textile units of the composition comprises as upper textile unit a fiber, fabric or thread comprising at least one fiber of HA or a physiologically acceptable salt thereof and at least one fiber of non-polar HA derivative according to general formula I, wherein the weight fraction of the substituent on the non-polar hyaluronic acid derivative of general formula–I is in the range of 14 to 20 wt %, preferably 15.5 to 18 wt %, and as a bottom textile unit a fiber, fabric or thread comprising at least one fiber of HA or a physiologically acceptable salt thereof and at least one fiber of non-polar HA derivative of general formula I, wherein the weight fraction of the substituent on the non-polar HA derivative of general formula I is in the range of 5 to 14 wt %, preferably 9 to 12.5 wt %. Preferably, the weight ratio of the fibers of HA or a physiologically acceptable salt thereof to the fibers of non-polar hyaluronic acid derivative of general formula I contained in the upper textile unit is 5:95 to 60:40, preferably 20:80 to 55:45, and the weight ratio of fibers of hyaluronic acid or a physiologically acceptable salt thereof to the fibers of non-polar HA derivative of general formula I contained in the bottom textile unit is 20:80 to 80:20, preferably 40:60 to 60:40 (see Table 5).

The textile units preferably contain the same type of non-polar derivative, preferably lauroyl HA or palmitoyl HA, the weight fraction of the substituent in the non-polar HA derivative being different in each unit. Preferably, the textile units contain an antimicrobial agent, more preferably octenidine or octenidine dihydrochloride.

TABLE 5

| Textile unit | Material composition | Weight fraction of substituent in non-polar derivative of HA [wt %] | | Weight ratio of HA:non-polar derivative of HA | |
|---|---|---|---|---|---|
| | | Range | Preferable range | Range | Preferable range |
| Upper | HA + non-polar derivative of HA | 14.0 to 20.0 | 15.5 to 18.0 | 5:95 to 60:40 | 20:80 to 55:45 |
| Bottom | HA + non-polar derivative of HA | 5.0 to 14.0 | 9.0 to 12.5 | 20:80 to 80:20 | 40:60 to 60:40 |

According to yet another embodiment, the set of textile units of the composition comprises as upper textile unit a fiber, fabric or thread comprising at least one fiber of HA or a physiologically acceptable salt thereof and at least one fiber of non-polar HA derivative of general formula I, wherein the weight fraction of the substituent on non-polar HA derivative of general formula I is in the range of 15.5 to 20 wt %, preferably 15.5 to 18 wt %, and as a middle textile unit a fiber, fabric or thread comprising at least one fiber of HA or a physiologically acceptable salt thereof and at least one fiber of non-polar HA derivative of general formula I, wherein the weight fraction of the substituent on the non-polar HA derivative of general formula I is in the range of 12.5 to 15.5 wt %, preferably 13.0 to 15 wt % and as a bottom textile unit a fiber, fabric or thread comprising at least one fiber of HA or a physiologically acceptable salt thereof and at least one fiber of non-polar hyaluronic acid derivative of general formula I, wherein the weight fraction of the substituent on the non-polar HA derivative of general formula I is in the range of 5 to 12.5 wt %, preferably 9.0 to 12.5 wt %. Preferably, the weight ratio of fibers of HA or a physiologically acceptable salt thereof to the fibers of non-polar HA derivative of general formula I contained in the upper textile unit is 5:95 to 60:40, preferably 20:80 to 55:45, furthermore the weight ratio of fibers of hyaluronic acid or a physiologically acceptable salt thereof to the fibers of non-polar HA derivative of general formula I contained in the middle textile unit is 20:80 to 80:20, preferably 40:60 to 60:40, and the weight ratio of the fibers of HA or a physiologically acceptable salt thereof to the fibers of the non-polar HA derivative of general formula I contained in the bottom textile unit is 20:80 to 80:20, preferably 40:60 to 60:40 (see Table 6).

The textile units preferably contain the same type of non-polar derivative, preferably lauroyl HA or palmitoyl HA, the weight fraction of the substituent in the non-polar HA derivative being different in each unit. Preferably, the textile units contain an antimicrobial agent, more preferably octenidine or octenidine dihydrochloride in the range of 0.07 to 0.15 wt %.

TABLE 6

| Textile unit | Material composition | Weight fraction of substituent in non-polar derivative of HA [wt %] | | Weight ratio HA:non-polar derivative of HA | |
|---|---|---|---|---|---|
| | | Range | Preferable range | Range | Preferable range |
| Upper | HA + non-polar derivative of HA | 15.5 to 20.0 | 15.5 to 18.0 | 5:95 to 60:40 | 20:80 to 55:45 |
| Middle | HA + non-polar derivative of HA | 12.5 to 15.5 | 13.0 to 15.0 | 20:80 to 80:20 | 40:60 to 60:40 |
| Bottom | HA + non-polar derivative of HA | 5.0 to 12.5 | 9.0 to 12.5 | 20:80 to 80:20 | 40:60 to 60:40 |

According to yet another embodiment, the set of textile units of the composition comprises as upper textile unit a fiber, fabric or thread comprising at least one fiber of HA or a physiologically acceptable salt thereof and at least one fiber of non-polar HA derivative of general formula I, wherein the weight fraction of the substituent on the non-polar hyaluronic acid derivative of general formula I is in the range of 14.0 to 20 wt %, preferably 15.5 to 18 wt %, furthermore as middle textile unit a fiber, fabric or thread comprising at least one fiber of HA or a physiologically acceptable salt thereof and at least one fiber of non-polar HA derivative of general formula I, wherein the mass fraction of the substituent on the non-polar HA derivative of general formula I is in the range of 14.0 to 20 wt %, preferably 15.5 to 18 wt % and as a bottom textile unit a fiber, fabric or thread comprising at least one fiber of HA or a physiologically acceptable salt thereof and at least one fiber of non-polar HA derivative of general formula I, wherein the mass fraction of the substituent on the non-polar HA derivative of general formula I is in the range of 5.0 to 14.0 wt %, preferably 9.0 to 12.5 wt %. Preferably, the weight ratio of fibers of HA or a physiologically acceptable salt thereof to the fibers of non-polar hyaluronic acid derivative of general formula I contained in the upper textile unit is 5:95 to 50:50, preferably 20:80 to 40:60, furthermore the weight ratio of the fibers of HA or a physiologically acceptable salt thereof to the fibers of non-polar HA derivative of general formula I contained in the middle textile unit is 30:70 to 70:30, preferably 40:60 to 60:40, and the weight ratio of the fibers of hyaluronic or a physiologically acceptable salt thereof to the fibers of the non-polar HA derivative of general formula I contained in the bottom textile unit is 20:80 to 80:20, preferably 40:60 to 60:40 (see Table 7).

The textile units preferably contain the same type of non-polar derivative, preferably lauroyl HA or palmitoyl HA, wherein in the upper and middle unit the weight fraction of the substituent in the nonpolar HA derivative is the same, in the bottom unit the weight fraction of the substituent in the nonpolar HA derivative is lower. The upper and middle units differ from each other in the weight ratio of the hyaluronan and non-polar hyaluronan fibers. Preferably, the textile units contain an antimicrobial agent, more preferably octenidine or octenidine dihydrochloride.

TABLE 7

| Textile unit | Material composition | Weight fraction of substituent in non-polar derivative of HA [wt %] | | Weight ratio of HA:non-polar derivative of HA | |
|---|---|---|---|---|---|
| | | Range | Preferable range | Range | Preferable range |
| Upper | HA + non-polar derivative of HA | 14.0 to 20.0 | 15.5 to 18.0 | 5:95 to 50:50 | 20:80 to 40:60 |
| Middle | HA + non-polar derivative of HA | 14.0 to 20.0 | 15.5 to 18.0 | 30:70 to 70:30 | 40:60 to 60:40 |
| Bottom | HA + non-polar derivative of HA | 5.0 to 14.0 | 9.0 to 12.5 | 20:80 to 80:20 | 40:60 to 60:40 |

According to yet another embodiment, the set of textile units of the composition comprises as upper textile unit a fiber, fabric or thread comprising at least one chloramide fiber of a chloramide HA derivative of general formula II and at least one fiber of a non-polar HA derivative of general formula I, wherein the Cl mass fraction on the chloramide derivative of HA of general formula II is in the range of 0.4 to 4.7 wt %, preferably 3.4 to 4.7 wt % and the mass fraction of the substituent on the non-polar hyaluronic acid derivative of general formula I is in the range of 15.5 to 20 wt %, preferably 15.5 to 18 wt %, furthermore as middle textile unit a fiber, fabric or thread comprising at least one chloramide fiber of a chloramide derivative of hyaluronic acid of general formula II and at least one fiber of a nonpolar derivative of HA of general formula I, wherein the mass fraction of Cl in the chloramide derivative of HA of general formula II is in the range of 0.4 to 4.7 wt %, preferably 3.4 to 4.7 wt % and the weight fraction of the substituent on the non-polar HA derivative of general formula I is in the range of 12.5 to 15.5 wt %, preferably 13.0 to 15.5 wt % and as bottom textile unit a fiber, fabric or thread comprising at least one chloramide fiber of a chloramide derivative of HA according to general formula II and at least one fiber of HA or a physiologically acceptable salt thereof, wherein Cl weight fraction in chloramide derivative of HA of general formula II is in the range of 0.4 to 4.7 wt %, preferably 3.4 to 4.7 wt % (see Table 8).

The upper and middle textile unit preferably comprises fibers of the same type of non-polar hyaluronan derivative according to the invention, preferably lauroyl HA or palmitoyl HA, the weight fraction of substituent in the non-polar HA derivative being different in each unit, and chloramide fibers according to the invention. The bottom textile unit comprises hyaluronan fibers and chloramide fibers according to the invention.

TABLE 8

| Textile unit | Material composition | Weight fraction of substituent in non-polar derivative of HA [wt %] | | Weight fraction of chloramide fibers in textile unit [wt %] | |
|---|---|---|---|---|---|
| | | Range | Preferable range | Range | Preferable range |
| Upper | Non-polar derivative of HA + chloramide HA | 15.5 to 20.0 | 15.5 to 18.0 | 5 to 60 | 20 to 55 |
| Middle | Non-polar derivative of HA + chloramide HA | 12.5 to 15.5 | 13.0 to 15.0 | 20 to 80 | 40 to 60 |
| Bottom | HA + chloramide HA | — | — | 20 to 80 | 40 to 60 |

According to a further preferred embodiment, the preparation set comprises as upper textile unit a fiber, fabric or thread comprising at least one mixed chloramide fiber of a chloramide HA derivative of general formula II and a fiber of non-polar HA derivative of general formula I and at least one fiber of non-polar HA according to general formula I, wherein the weight fraction of Cl in the chloramide derivative of the hyaluronic acid according to general formula II is in the range from 4.2 to 8.1 wt %, preferably 6.6 to 8.1 wt % and the weight fraction of the substituent on the non-polar HA derivative of general formula I is in the range of 12.5 to 20 wt %, preferably 15.5 to 18 wt %, as a middle textile unit a fiber, fabric or thread comprising at least one mixed chloramide fiber formed by a chloramide HA derivative of general formula II and a non-polar HA derivative of formula I and at least one fiber of non-polar HA derivative of general formula I, wherein the weight fraction of Cl in the chloramide derivative of HA according to general formula II is in the range of 4.2 to 8.1 wt %, preferably 6.6 to 8.1 wt % and the weight fraction of the substituent on the non-polar HA derivative of general formula I is in the range of 12.5 to 20 wt %, preferably 13.0 to 15.0 wt % and as a bottom textile unit a fiber, fabric or thread comprising at least one mixed chloramide fiber of a chloramide HA derivative of formula II and a non-polar HA derivative of formula I and at least one fiber of hyaluronic acid or a physiologically acceptable salt thereof, wherein the weight fraction of Cl in the chloramide derivative of HA according to general formula II is in the range from 4.2 to 8.1 wt %, preferably 6.6 to 8.1 wt % and the weight fraction of the substituent on the non-polar HA derivative of general formula I is in the range of 12.5 to 20 wt %, preferably 13.0 to 15.0 wt % (see Table 9).

The upper and middle textile unit preferably comprises fibers of the same type of non-polar hyaluronan derivative according to the invention, preferably lauroyl HA or palmitoyl HA, and mixed chloramide fibers of chloramide derivative HA and non-polar HA derivative, preferably lauroyl HA or palmitoyl HA. The bottom textile unit comprises hyaluronan fibers and mixed chloramide fibers of a chloramide derivative of HA and a non-polar derivative of HA, preferably lauroyl HA or palmitoyl HA.

TABLE 9

| Textile unit | Material composition | Weight fraction of substituent in non-polar derivative of HA [wt %] | | Weight fraction of chloramide fibers in textile unit [wt %] | |
|---|---|---|---|---|---|
| | | Range | Preferable range | Range | Preferable range |
| Upper | Non-polar derivative of HA + chloramide HA | 12.5 to 20.0 | 15.5 to 18.0 | 5 to 60 | 20 to 55 |
| Middle | Non-polar derivative of HA + chloramide HA | 12.5 to 20.0 | 13.0 to 15.0 | 20 to 80 | 40 to 60 |
| Bottom | HA + chloramide HA + non-polar derivative of HA | 12.5 to 20.0 | 13.0 to 15.0 | 20 to 80 | 40 to 60 |

According to a further preferred embodiment, the preparation set comprises as upper textile unit a fiber, fabric or thread comprising at least one mixed chloramide fiber of a chloramide HA derivative of general formula II and HA or a physiologically acceptable salt thereof and at least one fiber of non-polar HA derivative according to general formula I, wherein the weight fraction of Cl in the chloramide derivative of the HA according to general formula II is in the range from 4.2 to 8.1 wt %, preferably 6.6 to 8.1 wt % and the weight fraction of the substituent on the non-polar HA derivative of general formula I is in the range of 15.5 to 20 wt %, preferably 15.5 to 18 wt %, furthermore, as a middle textile unit a fiber, fabric or thread comprising at least one mixed chloramide fiber of a chloramide derivative of HA of general formula II and HA or a physiologically acceptable salt thereof and at least one fiber of a non-polar HA derivative of general formula I, wherein the weight fraction of Cl in the chloramide derivative of hyaluronic acid of general formula II is in the range from 4.2 to 8.1 wt %, preferably 6.6 to 8.1 wt % and the weight fraction of the substituent on the non-polar HA derivative of general formula I is in the range of 12.5 to 15.5 wt %, preferably 13.0 to 15.0 wt %, and as a bottom textile unit a fiber, fabric or thread comprising at least one mixed chloramide fiber formed by a chloramide derivative of HA of general formula II and HA or a physiologically acceptable salt thereof and at least one fiber of HA or a physiologically acceptable salt thereof. The weight fraction of Cl on the chloramide derivative of hyaluronic acid of general formula II is in the range of 4.2 to 8.1 wt %, preferably 6.6 to 8.1 wt % (see Table 10).

The upper and middle textile unit preferably comprises fibers of the same type of non-polar derivative according to the invention, preferably lauroyl HA or palmitoyl HA, the weight fraction of substituent in non-polar HA derivative being different in each unit, and mixed chloramide fibers formed by chloramide derivative HA and hyaluronic acid. The bottom textile unit contains HA fibers and mixed chloramide fibers formed by a chloramide derivative of HA and hyaluronic acid.

TABLE 10

| Textile unit | Material composition | Weight fraction of substituent in non-polar derivative of HA [wt %] | | Weight fraction of chloramide fibers in textile unit [wt %] | |
|---|---|---|---|---|---|
| | | Range | Preferable range | Range | Preferable range |
| Upper | Non-polar derivative of HA + chloramide HA + HA | 15.5 to 20.0 | 15.5 to 18.0 | 5 to 60 | 20 to 55 |
| Middle | Non-polar derivative of HA + chloramide HA + HA | 12.5 to 15.5 | 13.0 to 15.0 | 20 to 80 | 40 to 60 |
| Bottom | HA + chloramide HA | — | — | 20 to 80 | 40 to 60 |

According to another preferred embodiment, the weight fraction of chloramide fibers or mixed chloramide fibers contained in the upper textile unit is 5 to 60 wt % with respect to the weight of the upper textile unit, preferably 20 to 55 wt %, furthermore the weight fraction of chloramide fibers or mixed chloramide fibers contained in the middle textile unit is 20 to 80 wt % with respect to the weight of the middle textile unit, preferably 40 to 60 wt %, furthermore the weight fraction of chloramide fibers or mixed chloramide fibers contained in the bottom textile unit is 20 to 80 wt % with respect to the weight of the bottom textile unit, preferably 40 to 60 wt %, as shown in Tables 8, 9 and 10.

The following technological steps are required to form a dental preparation: The first is the formation of a fiber, which is performed by spinning a polymer solution by a method known in the prior art (WO2012089179, WO2014082610 A1, WO2014082611 A1). The process of formation of a fiber from hyaluronan or a non-polar HA derivative of general formula I begins by weighing the required amount of polymer, and mixing and dissolving it in a suitable solvent (water, water-alcohol mixture). The formed polymer solution is degassed, and then extruded by means of a spinning nozzle into a coagulation bath containing a mixture of an organic acid and an alcohol, where the viscous solution is converted into a gel-like fiber which is continuously drawn and wound on a spool. Residual solvent and coagulation bath are then removed from the fiber during washing (e.g. in alcohol). In the case of a non-polar HA derivative, washing in acetone follows. Finally, the fiber is dried. The required physicochemical and biological properties are achieved by the choice of derivative, the concentration of the spinning solution, the shape of the nozzle, the composition of the coagulation bath, the dosing rate, the winding rate, the draw ratio and the washing and drying conditions. Chloramide fibers are prepared in a similar manner Mixed chloramide fibers are formed by spinning a solution containing two polymeric components—a chloramide HA derivative of general formula II and hyaluronic acid or a chloramide HA derivative and a non-polar HA derivative of general formula I. The resulting fiber can be used either directly as a textile unit as part of a dental set preparation according to the invention, or serves as an intermediate for the formation of a thread or fabric. In this case, the mechanical textile treatment of the fibers is followed by conventional techniques, including fiber bundling, twisting, weaving, knitting, nonwoven fabric production, preferably braiding. During this processing, a textile unit is formed, preferably a braided thread or strip of fabric, which may comprise one type of fibers or of a mixture of several types of hyaluronan-based fibers according to the invention. The required thread diameter can be easily achieved by choosing the fineness of the fibers, and their number. The required width of the fabric strip can also be easily achieved—for example, for fabrics and warp knits by the number of warp threads, the nonwoven fabric can be cut into strips of the required width. The antimicrobial agent, preferably an antiseptic, is applied to the fiber, thread or fabric in the final stage of processing (with the exception of the chloramide derivative of HA of general formula II, which is a chloramide fiber or which is contained in a mixed chloramide fiber). For the application of antimicrobial agent, one of the conventional methods and technological equipment used in textile finishing can be used, such as spraying, impregnation with a wading roller, preferably padding on a foulard or nozzle application, etc. These procedures can be implemented in continuous roll-to-roll, when during rewinding a solution of antimicrobial agent is applied to the fiber, thread or fabric, the solvent is evaporated in the drying zone and the finished fabric is wound on a product roll or spool. Padding on the foulard is carried out by wetting the fiber, thread or fabric in a solution of antimicrobial agent, and squeezing the excess solution between the spinning rollers of the foulard, followed by drying and winding. The amount of antimicrobial substance applied to the fiber, thread or fabric can, in this case, be controlled in particular by the choice of the concentration of the solution, the pressure of the squeezing rollers, and by the rewinding speed. A needle nozzle can be advantageously used to apply the antimicrobial agent to the fiber or thread. In this case, the antimicrobial solution is dispensed by means of a plunger syringe and a linear dispenser into a vertically oriented needle nozzle, the mouth of which points downwards. The fiber or thread is guided so that it touches the side of the needle nozzle about 1 to 3 mm above its mouth. The solution rises on the surface of the nozzle and is continuously wiped and absorbed by the fiber or thread during rewinding. This is followed by drying and winding. The amount of antimicrobial substance applied to the fiber or thread can be controlled especially by the choice of solution concentration, dosage and by rewinding speed. During the coating process, due to the porosity of the fibers, the solution penetrates into the fiber, so that after evaporation of the solvent, the antimicrobial agent remains not only on the surface but also inside the fiber. Preferably, a solution of octenidine dihydrochloride in alcohol, preferably in ethanol, at a concentration of 1 to 8 mg/mL is used for coating. The final operation of the dental preparation is usually terminal sterilization, e.g. by gamma irradiation or ethylene oxide.

The dental preparation according to the present embodiments is unique in the sense that its carrier component is only based on one type of chemical agent (hyaluronic acid), while its properties are expediently adapted to fill the periodontal pocket, and create a suitable environment for healing. This differs significantly from the periodontal gel composition according to WO 2018158764, which contains the thermosensitive copolymer (poloxamer) necessary for the conversion of the HA solution into a gel. The presence of poloxamer as a non-degradable component of the gel composition is a disadvantage compared to the fully degradable composition of the present invention. Another difference is that the authors of the said application progress from a liquid state of low viscosity to a gel-like preparation, the viscosity of the preparation increasing. According to the present invention, based on the use of a fibrous material, the process is progressed from a solid state to a gel-like preparation. This makes the preparation easy to handle during implantation and, when inserted into the periodontal pocket, the preparation adheres well to the moist tissue and remains there without being extruded (see Example 21). As already mentioned, the key feature that distinguishes the two solutions is biodegradability. In the case of WO 2018158764, the gel composition is not fully absorbable, while the preparation of the present invention formed by fibers gradually transitioning to a gel is absorbed and this absorption is controlled depending on the type of nonpolar HA derivative of general formula I and the weight fraction of substituent (see Example 19). In vivo testing of the dental preparation according to the present embodiments showed histologically that the material remained in the gums of the rabbit for 2 weeks, while during the control at 4 weeks it was already fully resorbed and only reparative tissue was at the application site. After 6 weeks, the application site was fully healed ad integrum and the area around the implantation site showed no signs of an inflammatory reaction (see Example 20). Furthermore, in contrast to the preparation according to WO18158764, it is not necessary to have any organic solvent present in the preparation when applied to the periodontal pocket to dissolve the antimicrobial agent. The solvent is only used in the manufacturing phase when applying an antimicrobial agent, such as octenidine, and is removed during drying and sterilization to a safe value of less than 0.5 wt %. Suitable volatile solvents for applying the antimicrobial are, for example, alcohols, preferably isopropyl alcohol or ethanol, which can be easily evaporated after impregnation of the fiber, thread or fabric. Using the inhibition zone method, the antimicrobial activity of the dental preparation containing octenidine dihydrochloride according to the present embodiments against the *Aggregatibacter actinomycetemcomitans* strain was demonstrated (see Example 17). On the other hand, in the in vivo test in the rabbit model, no negative reaction to the presence of the tested preparation was detected, or of the antiseptic used, even at the highest octenidine content by weight of 0.38 wt % in textile unit—thread (see example 18). The dental preparation according to the invention, in an embodiment in which it contains an antimicrobial substance, can be included among the LDDSs which have been described in the prior art. Due to the local application of the preparation, it does not come into contact with the internal environment, the active agent does not degrade during the first pass through the liver, locally high therapeutic doses can be achieved, at the application site the agent is effective for a long time and application is non-invasive, painless and easy.

From the state of the art it is apparent, that for a long time the experts have tried to create a fibrous preparation containing an antimicrobial agent intended to fill a periodontal pocket. The use of a non-degradable ethylene vinyl acetate copolymer according to U.S. Pat. Nos. 4,892,736 and 4,764,377 proved to be unsuitable and it can be assumed that even the combination of ethylene vinyl acetate with a biodegradable material according to WO 2010068940 A2 will not solve the problem with residues of non-degradable polymer. The composite material based on collagen, a copolymer of polylactic acid and polyglycolic or oxycellulose according to U.S. Pat. No. 5,447,940 A is absorbable, but it consists of materials which are not inherent in the body, and do not allow to create conditions for healing from the bottom of the pocket.

Although hyaluronan ester fibers have been known for many years according to U.S. Pat. No. 5,622,707, which have been tested in the form of a composite membrane in a series of experiments involving surgery of periodontium, experts have not exploited their application to the treatment of periodontitis. In the prior art, there is a tendency towards different application of carrier fiber systems, which were originally intended to fill the periodontal pocket, to disinfect the root system or the root canal of the tooth (WO 00/59469, WO 2010068940 A2), which suggests that the development of fibrous materials for periodontitis has reached a dead end. However, the dental preparation according to the present embodiments shows that fibers based on HA and its derivatives are a suitable material for the treatment of periodontitis. Compared to materials for controlled tissue regeneration, the dental preparation according to the present embodiments does not require surgical intervention—it is only inserted into the periodontal pocket. Compared to other materials intended to fill the periodontal pocket, its advantage is that the textile unit in the form of a fiber, thread or hyaluronan-based fabric performs a mechanical function (reinforcing and sealing), and acts as a carrier of the active agent, while all fibers contained in the dental preparation according to the present embodiments are not only biocompatible but also intrinsic to the body, are fully biodegradable and, in addition, the presence of hyaluronic acid creates suitable conditions for healing.

The inventive step in this case involved the creation of a dental preparation according to the invention, which comprises a combination of at least one hyaluronic acid fiber and at least one fiber of non-polar HA derivative according to general formula I according to the invention, and facilitates the concept of gradual pocket healing (from the bottom of the pocket); and further the systematic selection of suitable derivatives based on their biodegradability, their spinning, creation of a textile unit with a structure and geometry suitable for insertion into a pocket, development of antimicrobial incorporation technology and the verification in both in vitro, and in vivo animal model.

A person skilled in the art could be concerned that in the textile unit described in the invention, the fibers from the derivative may be washed away from the site of action, (the periodontal pocket), due to the dissolution of the HA fibers. Concerning the retention period of the product at the aimed site of action, the gel form is not entirely suitable for application into the periodontal pocket. In general, the gel is further diluted in the periodontal pocket and washed away by the blood present in the wound. Therefore, one skilled in the art would prefer to choose the variant without the presence of immediately soluble fibers of native hyaluronic acid in order to achieve the retention of the thread in the periodontal pocket. But surprisingly, in the dental preparation, the fibers of the non-polar derivative help to retain in the mass of the hyaluronic acid gel which is formed when the HA fibers are dissolved. Unlike a situation where the HA gel is applied directly into the pocket, and nothing else keeps it in. When fibers/threads only from the HA derivative are used, there is no benefit of the presence of simple HA, the healing effects of which are known.

If an antimicrobial agent, in particular octenidine, is coated on threads or fabrics formed by only one type of fiber, i.e. either HA fibers or non-polar hyaluronan fibers of general formula I, then the octenidine content is comparable in both cases while using the same process parameters (see example 15). A surprising finding, therefore, was that the distribution of octenidine deposited on the thread formed by the mixture of hyaluronan fibers and non-polar hyaluronan fibers is markedly asymmetric—the octenidine content on non-polar HA derivatives is significantly higher than on HA fibers (see Example 16). Surprisingly, the asymmetric distribution of octenidine between the two types of fibers occurs over a very short period of time during continuous application, with the time between soaking the thread or fabric with octenidine solution and evaporating the solvent being only a few seconds. If the weight ratio of the hyaluronic acid fibers to the fibers of the non-polar HA derivative in the textile unit (thread or fabric) is about 50:50, then the total amount of octenidine contained is about 25 wt % octenidine present in the hyaluronic acid fibers, while 75 wt % is in non-polar HA derivative fibers. This effect is advantageous for achieving a longer antimicrobial effect of the formulation, as octenidine released from dissolved hyaluronan fibers kills pathogenic microorganisms initially after implantation into the periodontal pocket, while most octenidine anchored in swollen fibers from nonpolar hyluronan derivative is gradually released. during polymer biodegradation. The controlled release of the antimicrobial can be further influenced by the weight ratio of the fibers in the textile unit: If the weight ratio of hyaluronic acid fibers to non-polar HA derivatives is about 25:75, then only about 7 wt % of the total amount of octenidine in the textile unit is present in the fibers of hyaluronan, while in fibers of the non-polar derivative about 93 wt %. At the opposite weight ratio of fibers, i.e. 75:15, about 50 wt % is present in both the hyaluronic acid fibers and the non-polar HA derivative fibers. A higher proportion of hyaluronic acid fibers promotes the antimicrobial action of the dental preparation in the initial phase after implantation, while reducing their proportion in favor of non-polar HA-derived fibers promotes antimicrobial action over a longer period of time.

Definitions and Abbreviations

Hyaluronic acid, hyaluronan, HA: polymer consisting of repeating disaccharide units formed by D-glucuronic acid and N-acetylglucosamine Hyaluronic acid, resp. hyaluronan (HA) also means a physiologically acceptable salt thereof selected from the group comprising a physiologically acceptable metal cation, i.e. an alkali metal ion or an alkaline earth ion, preferably $Na^+$, $K^+$, $Ca^{2+}$, $Mg^{2+}$, more preferably $Na^+$.

Non-polar HA derivative: modified hyaluronan of general formula I containing a substituent in the form of acyl, ethyl or benzyl. A non-polar derivative is also understood to mean a physiologically acceptable salt thereof selected from the group comprising of a physiologically acceptable metal cation, i.e. an alkali metal ion or an alkaline earth ion, preferably $Na^+$, $K^+$, $Ca^{2+}$, $Mg^{2+}$, more preferably $Na^+$.

Chloramide derivative HA, hyaluronan chloramide: a hyaluronan derivative of general formula II having a hydrogen of the amide group —NH—CO— substituted by a chlorine atom of the structural formula —NCl—CO—. The chloramide derivative according to the present embodiments is also understood to mean a physiologically acceptable salt thereof selected from the group comprising a physiologically acceptable metal cation, i.e. an alkali metal ion or an alkaline earth ion, preferably $Na^+$, $K^+$, $Ca^{2+}$, $Mg^{2+}$, more preferably $Na^+$.

Physiologically acceptable metal cation: alkali metal ion or alkaline earth ion, preferably $Na^+$, $K^+$, $Ca^{2+}$, $Mg^{2+}$, more preferably $Na^+$.

Monofil: a single filament, extruded separately using a single-hole spinning nozzle Multifil: an endless filament formed by a bundle of fibrils of the same composition, simultaneously extruded by a spinning nozzle with two or more holes Staple fiber: a short fiber with a length ranging from 1 to 150 mm.

Fiber: monofilament, multifilament, or staple fiber as defined above. The fineness of the fibers of HA, non-polar HA derivative or HA chloramide is in the range of 3 to 40 tex, preferably 6 to 11 tex.

Fineness, abbreviated T: length weight of fiber or thread; it is expressed in units of [tex](1 tex=1 g/km=1 mg/m). The fineness values reported in this document were determined gravimetrically.

Fiber thickness: The width of the fiber projection. In different directions, the fiber thickness is different because the fibers of hyaluronan and its derivatives have an irregular (non-circular) cross section due to the coagulation process. For this reason, the diameter of these fibers cannot be determined.

Fabric: a planar or tubular structure comprising the fibers of the present embodiments; it may be a woven, non-woven, knitted or plaited fabric.

Thread: a length structure comprising the fibers of the present embodiments and made by textile processes, which may include joining, braiding, twisting, plying, knitting, preferably braiding. It may be a bundle of parallel oriented fibers formed by combining two or more fibers of the same or different composition, a twisted bundle of fibers, a knitted chain or a braided thread.

Chloramide fiber: a fiber from the chloramide derivative HA according to the present embodiments.

Mixed chloramide fiber: a fiber comprising a chloramide HA derivative of the present embodiments and hyaluronic acid, or a chloramide HA derivative of the present embodiments and a non-polar hyaluronic acid derivative of general formula I.

Textile unit: a form of a dental preparation according to the present embodiments, comprising a combination of at least one hyaluronan fiber and at least one fiber of non-polar hyaluronan derivative according to general formula I. If the dental preparation according to the present embodiments comprises a set of textile units (i.e. two or more textile units) some of the textile units may comprise a fiber, fibers, fabric or thread of hyaluronan, or a fiber, fibers, fabric or thread of a non-polar hyaluronan derivative of general formula I, or a chloramide fiber or a mixed chloramide fiber. Thus, a textile unit is a fiber, thread or fabric.

Bottom textile unit: a fibrous structure of a specific composition according to the present embodiments, intended for insertion on the bottom of a periodontal pocket Middle textile unit: a fibrous structure of a specific composition according to the present embodiments, intended for insertion into the central region of a periodontal pocket Upper textile unit: a fibrous structure of a specific composition according to the present embodiments, intended for insertion into the upper region of a periodontal pocket Set: A group of at least two textile units of different material composition intended for different areas of the periodontal pocket Substituent: in the non-polar hyaluronic acid derivative of general formula I, either R is selected from the group comprising benzyl or ethyl or $R^1$ is acyl, i.e. —C(=O)$C_xH_y$.

In the chloramide derivative of hyaluronic acid of general formula II, the substituent $R^2$ is chlorine.

Support treatment: This is a process that helps to successfully regenerate and heal the tissue, i.e. to treat. HA as an important component of the extracellular matrix in the whole organism represents an essential component of the connective tissue of the periodontium (periodontal ligaments, gums). Thus, the presence of HA and the HA derivatives of the present embodiments within the periodontal pocket serves as an ideal environment for the formation of new periodontal ligaments and the replacement of lost tissue. Due to the presence of the antimicrobial agent according to the invention, the root surface is disinfected, and the inner surface of the periodontal pocket is prevented from being recolonized by microorganisms from the environment of the oral cavity. One skilled in the art will appreciate that the antimicrobial agent promotes treatment and that HA in combination with HA derivatives is involved in both treatment and support.

Analytical Methods

HPLC: high-performance liquid chromatography. The content of antiseptics (octenidine and chlorhexidine) in the dental preparation according to the present embodiments was determined by this analytical method. The antiseptic content is expressed as the ratio of the weight of the antiseptic in the sample to the total weight of the sample of the dental preparation. The resulting value is expressed in weight percent [wt %].

GC: gas chromatography. The content of the substituent (lauroyl, palmitoyl, capronoyl) in the nonpolar HA derivative was determined by this analytical method. The content of the substituent is expressed as the ratio of the weight of the substituent in the sample of the non-polar HA derivative and the total weight of the sample of the non-polar HA derivative. The resulting value, referred to as the weight fraction of the substituent, is expressed in weight percent [wt %].

NMR: Nuclear magnetic resonance spectroscopy. The content of the substituent (chlorine) in the chloramide derivative of HA was determined by this analytical method. The content of the substituent is expressed as the ratio of the weight of the substituent in the sample of the chloramide derivative HA and the total weight of the sample of the chloramide derivative HA. The resulting value, referred to as the weight fraction of the substituent, is expressed in weight percent [wt %]. In some cases, the degree of substitution (abbreviation DS) is also given for comparability with CZ308010. For the chloramide derivative HA, the following relationship applies between the weight fraction of the substituent (w/w) and the degree of substitution (abbreviation DS=molar amount of modified disaccharides/molar amount of all disaccharides): w/w=DS×35.45/(400+DS× 35.45)

Laser sensor: It was used to measure the thread diameter in dry state, if a sample with a length of min. 50 m was available. The measuring principle consists in periodically sensing the thread thickness using a laser during rewinding, in four directions of 45° (perpendicular to the thread axis). The resulting thread diameter was then calculated by averaging the measured values. An Accuscan 6012 instrument was used for the measurement.

Optical microscopy: It was used to measure fiber thickness and thread diameter in both dry and wet conditions. A Nikon Ci-L instrument and NIS-elements image analysis were used for the measurements. The diameter of the dry threads was measured by optical microscopy if the available thread length was less than 50 m.

EXAMPLES

Example 1: Synthesis of Capronoyl Hyaluronan 1000 g of hyaluronan with a weight average molecular weight (Mw) of $2.4×10^5$ g/mol were dissolved in 20 liters of distilled water. Then 3.2 equivalents of triethylamine and 3 g of 4-dimethylaminopyridine were added as catalysts and 20 liters of isopropanol were added. The mixture was homogenized for 3 hours. Then 2.1 equivalents of hexanoic anhydride were added. The reaction was carried out at 20° C. for 2.5 hours. The product was isolated by precipitation with 20 liters of absolute isopropanol and then repeatedly purified with isopropanol at a concentration in the following order: 100%, 85% (5×), 100% (2×)-20 liters each. Finally, the product was dehydrated with absolute isopropanol and dried for 72 hours at 40° C. in a hot air oven. The resulting weight fraction of substituent in the resulting capronoyl of hyaluronan was 8.32 wt % (determined by GC). The Mw of the derivative did not change compared to the starting hyaluronan.

Example 2: Synthesis of Lauroyl Hyaluronan with Low Fraction of Substituent 25 g of hyaluronan with Mw of $3.4×10^5$ g/mol were dissolved in 350 ml of distilled water. Then 1.6 equivalents of triethylamine and 0.38 g of 4-dimethylaminopyridine as catalysts and 350 ml of tetrahydrofuran were added. The mixture was homogenized for 2 hours. Then 0.8 equivalent of lauric anhydride was added. The reaction was run at 20° C. for 3 hours. The product was isolated by precipitation with 3 liters of absolute isopropanol and then repeatedly purified with isopropanol at a concentration in the following order: 100%, 80%, 85%, 90%, 95%, 100% (2×)-2 liters each. Finally, the product was dehydrated with absolute isopropanol and dried for 72 hours at 40° C. in a hot air oven. The resulting weight fraction of substituent in the resulting lauroyl hyaluronan was 10.96 wt % (determined by GC). The Mw of the derivative did not change compared to the starting hyaluronan.

Example 3: Synthesis of Lauroyl Hyaluronan with High Fraction of Substituent 25 g of hyaluronan with Mw of $3.4×10^5$ g/mol were dissolved in 350 ml of distilled water. Then 2.1 equivalents of triethylamine and 0.38 g of 4-dimethylaminopyridine as catalysts and 350 ml of tetrahydrofuran were added. The mixture was homogenized for 2 hours. Then 1.3 equivalents of lauric anhydride were added. The reaction was run at 20° C. for 3 hours. The product was isolated by precipitation with 3 liters of absolute isopropanol and then repeatedly purified with isopropanol at a concentration in the following order: 100%, 80%, 85%, 90%, 95%, 100% (2×)-2 liters each. Finally, the product was dehydrated with absolute isopropanol and dried for 72 hours at 40° C. in a hot air oven. The resulting weight fraction of substituent in the resulting lauroyl hyaluronan was 15.90 wt % (determined by GC). The Mw of the derivative did not change compared to the starting hyaluronan.

Example 4: Capronoyl Hyaluronan Fiber

Capronoyl hyaluronan with Mw of $2.4×10^5$ g/mol and a weight fraction of substituent 8.32 wt % prepared according to the procedure of Example 1 was used as the starting material for the fiber formation. By dissolving 2.5 g of this polymer in a mixture consisting of 26 ml of isopropanol and 26 ml of demineralized water, a solution with a concentration of 48 mg/ml was prepared. After reconstitution, the solution was transferred to a syringe and degassed by centrifugation. The solution was metered at a rate of 200 μl/min into a 1:4 lactic acid-isopropanol precipitation bath. The fiber was wound at a speed of 1.32 m/min. Subsequently, the fiber was washed in ethanol, then in acetone and finally dried. The fiber fineness was 9.1 tex, thickness 100 μm, strength 1.15 N and ductility 13.9%.

Example 5: Fiber of Lauroyl Hyaluronan with Low Fraction of Substituent

Lauroyl hyaluronan with Mw of $3.4 \times 10^5$ g/mol and a weight fraction of substituent of 10.96 wt %, prepared according to the procedure of Example 2 was used as the starting material for the fiber formation. A solution with a concentration of 49 mg/ml was prepared by dissolving 15.42 g of this polymer in a mixture consisting of 156 ml of isopropanol and 156 ml of demineralized water. After reconstitution, the solution was transferred to a syringe and degassed with centrifuge. The solution was metered at a rate of 200 μl/min into a 1:4 lactic acid-isopropanol precipitation bath. The fiber was wound at a speed of 1.32 m/min. Subsequently, the fiber was washed in isopropanol, then in acetone and finally dried. The fineness of the fiber was 8.2 tex, thickness 100 μm, strength 0.86 N and ductility 20.6%. Subsequently, the fiber thickness after 20 minutes of wetting was determined using an optical microscope: a) in demineralized water, b) in phosphate buffer. Subsequently, the radial swelling of the fiber was calculated as the ratio of the increase in the thickness of the swollen fiber to the thickness of the starting dry fiber. The radial swelling was 165% in demineralized water and 576% in phosphate buffer. To determine the rate of enzymatic degradation of the fiber in vitro, the methodology known from the prior art was adapted, which was originally developed to study the degradation of hyaluronan-based hydrogels (Bobula et al. 2017) and hyaluronan-based thin films (Chmelař et al. 2019). Briefly, a sample of the fiber (10.0 mg±0.5 mg) was placed in a glass vial and embedded in 1 mL of degradation solution (50 mM phosphate buffer pH 7.0) containing the SpHyl enzyme (0.11 IU mL$^{-1}$). The glass vial was sealed and placed in a tempered shaking thermostat at 37° C. At predetermined intervals (20, 40, 60 min, 2, 3, 4, 6, 8, 10, 12, 24, 36, 48, 60 and 72 hours), the degradation solution was removed and replaced with fresh solution. In each time interval, the amount of HA/lauroyl HA released into the solution was determined spectrophotometrically (Pepeliaev et al. 2017). The rate of degradation [wt %/hour] was determined from the linear dependence of the cumulative release of HA/lauroyl HA [wt %] on the degradation time [hours]. All experiments were performed in duplicate. The rate of enzymatic degradation of lauroyl HA fibers in vitro was 94.9 wt %/hour. At this enzyme content, the rate of enzymatic degradation was very fast, and the evaluation was performed only from the first three time points of the whole experiment (as the sample was degraded afterwards).

Example 6: Fiber of Lauroyl Hyaluronan with High Fraction of Substituent

Lauroyl hyaluronan with Mw a of $3.4 \times 10^5$ g/mol and a weight fraction of the substituent of 15.90 wt % prepared according to the procedure of Example 3 was used as the starting material for the fiber formation. A solution with a concentration of 49 mg/ml was prepared by dissolving 15.42 g of this polymer in a mixture consisting of 156 ml of isopropanol and 156 ml of demineralized water. After reconstitution, the solution was transferred to a syringe and degassed by centrifugation. The solution was metered at a rate of 200 μl/min into a 1:4 lactic acid-isopropanol precipitation bath. The fiber was wound at a speed of 1.32 m/min. Subsequently, the fiber was washed in isopropanol, then in acetone and finally dried. The fineness of the fiber was 8.3 tex, thickness 102 μm, strength 0.84 N and ductility 22.3%. Subsequently, the fiber thickness after 20 minutes of wetting was determined using an optical microscope: a) in demineralized water, b) in phosphate buffer. Subsequently, the radial swelling of the fiber was calculated as the ratio of the increase in the thickness of the swollen fiber to the thickness of the starting dry fiber. The radial swelling was 90% in demineralized water and 296% in phosphate buffer. The rate of enzymatic degradation of lauroyl HA fibers in vitro, determined by the procedure described in Example 5, was 7.2%/hour (evaluation was performed in the range of 0-12 hours of degradation).

Example 7: Fiber of Hyaluronan Palmitoyl Ester

Hyaluronan palmitoyl ester with Mw of $3.3 \times 10^5$ g/mol and a weight fraction of substituent of 13.97 wt % prepared by a method known in the art (WO2014082611 A1) was used as the starting material for the fiber formation. A solution with a concentration of 54 mg/ml was prepared by dissolving 2.8 g of this polymer in a mixture of 26 ml of isopropanol and 26 ml of demineralized water. After reconstitution, the solution was transferred to a syringe and degassed by centrifugation. The solution was metered at a rate of 200 μl/min into a 1:4 lactic acid-isopropanol precipitation bath. The fiber was wound at a speed of 1.45 m/min. Subsequently, the fiber was washed in isopropanol, then in acetone and finally dried. The fineness of the fiber was 8.9 tex, thickness 98 μm, strength 0.62 N and ductility 19.2%. Subsequently, the fiber thickness after 20 minutes of wetting was determined using an optical microscope: a) in demineralized water, b) in physiological saline (0.9% aqueous NaCl solution). Subsequently, the radial swelling of the fiber was calculated as the ratio of the increase in the thickness of the swollen fiber to the thickness of the starting dry fiber. The radial swelling was 230% in demineralized water and 212% in saline.

Example 8: Dental Preparation Containing Hyaluronan and Hyaluronan Ethyl Ester A multifilament fiber of hyaluronan having Mw of $4.4 \times 10^5$ g/mol, prepared by a method known in the art (WO2012089179) was used for the dental preparation, wherein the fineness of a multifilament consisting of 7 fibrils was 35 tex, and a multifilament fiber of hyaluronan ethyl ester of Mw of $2.3 \times 10^5$ g/mol and weight fraction of substituent 6.0 wt % (DS 52%), prepared according to a method known in the art (U.S. Pat. No. 5,622,707), the fineness of the multifilament consisting of 7 fibrils being 37 tex. On the VUB ring twisting machine, these multifilament fibers were combined and twisted together at a fiber feed speed of 10 m/min and a spindle speed of 2200 min$^{-1}$. The resulting dental preparation in the form of a twisted thread had a diameter of 285 μm and a twist of 220 m$^{-1}$.

Example 9: Dental Preparation Containing Hyaluronan and Hyaluronan Benzyl Ester A multifilament fiber of HA having Mw of $4.4 \times 10^5$ g/mol, prepared according to a prior art method (WO2012089179) was used for the dental preparation, the fineness of the multifilament consisting of 7 fibrils being 35 tex, and a multifilament fiber of hyaluronan benzyl ester of Mw of $2.3 \times 10^5$ g/mol and weight fraction of substituent 25.7 wt % (DS 95%), prepared according to a method known in the art (U.S. Pat. No. 5,622,707), the fineness of the 7-fibril multifilament being 34 tex. On the VUB ring twisting machine, these multifilament fibers were combined and twisted together at a fiber feed speed of 10 m/min and a spindle speed of 2200 min$^{-1}$. The resulting dental preparation in the form of a twisted thread had a diameter of 273 μm and a twist of 220 m$^{-1}$.

Example 10: A Set of Textile Units in the Form of a Fabric Strip

Monofilament fibers of lauroyl HA with Mw of $3.5 \times 10^5$ g/mol and a weight fraction of substituent of 14.41 wt % and a fineness of 8.2 tex prepared in a manner similar to Example 6 were used for the upper textile unit. On a VUB ring twisting machine, two of these fibers were combined and twisted together at a fiber feed speed of 10 m/min and a spindle speed of 3000 min$^{-1}$. The resulting thread had a twist of 300 m$^{-1}$. Subsequently, two warps were prepared, each consisting of four threads. A double warp knitting machine Comez with a division of G12 (12 needles per 2.54 mm) was used to create the fabric—raschel. Three reed needles were mounted on the front and rear bed of the machine. Subsequently, with the help of two laying devices, a strip of double-faced fabric was knitted in a knitted weave with closed stitches (laying device formulas—front: 2-2/2-1/2-2/ 2-3//; back: 2-1/2-2/2-3/2-2//). The resulting width of the fabric strip was 7 mm. The textile unit in the form of a textile strip is shown in FIG. 2b.

Monofilament hyaluronan fibers with Mw of $4.4 \times 10^5$ g/mol and a fineness of 8.3 tex prepared according to a method known from the prior art (WO2012089179) were used for the lower textile unit. On the VUB ring twisting machine, two of these fibers were combined and twisted together at a fiber feed speed of 10 m/min and a spindle speed of 3000 min$^{-1}$. The resulting thread had a twist of 300 m$^{-1}$. Subsequently, two warps were prepared, each consisting of four threads. On a Comez double warp knitting machine with a G12 division, a strip of fabric was knitted in the same way as for the upper textile unit. The resulting width of the fabric strip was 7 mm

Example 11: A Set of Textile Units in the Form of a Braided Thread I

Hyaluronan monofilament fibers with Mw of $3.99 \times 10^5$ g/mol and a fineness of 8.5 tex, prepared by a method known in the art (WO2012089179), and lauroyl HA fibers with Mw of $3.5 \times 10^5$ g/mol, fineness 8.9 tex and substituent content 16.45 wt %, prepared in a similar manner to Example 6 were used. A series of braided threads (textile units) was formed from these fibers on a Steeger horizontal braiding machine, which contained a combination of hyaluronan fibers and hyaluronan lauroyl fibers, the individual fiber types being represented in the threads in different number; in total, each thread contained 16 fibers. The structural characteristics of the individual textile units in the form of thread are given in Table 11. The values of the weight ratio of fibers in the thread $P_{HA}$:$P_D$ (here the ratio hyaluronan:lauroyl HA) were calculated according to the relations $$P_{HA}=N_{HA} \times T_{HA}(N_{HA} \times T_{HA}+N_D \times T_D) \times 100,$$

and $$P_D=N_D \times T_D(N_{HA} \times T_{HA}+N_D \times T_D) \times 100,$$

where $P_{HA}$ is the weight fraction of HA fibers [wt %], $P_D$=is the weight fraction of fibers from the non-polar derivative HA [wt %], NITA is the number of HA fibers in the thread, $T_{HA}$ is the fineness of the HA fibers, $N_D$ is the number of fibers of the non-polar HA derivative in the thread, and $T_D$ is the fineness of the non-polar HA derivative fibers. To determine the rate of enzymatic degradation of threads in vitro, a methodology known from the prior art was adapted, which was originally developed to study the degradation of hyaluronan-based hydrogels (Bobula et al. 2017) and hyaluronan-based thin films (Chmelař et al. 2019). Simply put, a thread sample (10 mg±0.5 mg) was placed in a glass vial and poured over with 1 mL of degradation solution (50 mM phosphate buffer pH 7.0) containing SpHyl enzyme (0.0033 IU mL$^{-1}$). The glass vial was sealed and placed in a tempered shaking thermostat at 37° C. At predetermined time points (20, 40, 60 min, 2, 3, 4, 6, 8, 10, 12, 24, 36, 48, 60 and 72 hours), the degradation solution was removed and replaced with fresh solution. In each time point the amount of HA/lauroyl HA released into the solution was determined spectrophotometrically (Pepeliaev et al. 2017). Degradation rate [wt %/hour] was determined from the linear dependence of the cumulative release of HA/lauroyl HA [wt %] at degradation time [hours]. All experiments were performed in duplicate. Table 11 lists the two degradation rates for each sample. The first number indicates the degradation of native HA (evaluated from degradation samples taken in time points between 0-2 hours) and the second value is evaluated from areas where lauroyl HA is degraded (middle and bottom textile unit—times 2-4 hours, upper textile unit— times 2-8 hours). From the results shown in Table 11, it is clear that with increasing weight fraction of lauroyl HA fibers in the textile unit, the rate of its enzymatic degradation decreases.

TABLE 11

| Textile unit | Material composition | Number of fibers in a thread | Weight ratio of fibers $P_{HA}$:$P_D$ | Thread diameter* [μm] | Rate of enzymatic degradation [%/hrs] |
|---|---|---|---|---|---|
| Upper | Hyaluronan | 4 | 24:76 | 551 | 22.24/10.29 |
| | Lauroyl HA | 12 | | | |
| Middle | Hyaluronan | 8 | 49:51 | 551 | 31.86/14.64 |
| | Lauroyl HA | 8 | | | |
| Bottom | Hyaluronan | 12 | 74:26 | 512 | 82.88/16.96 |
| | Lauroyl HA | 4 | | | |

*Determined using an optical microscope

Example 12: Set of Textile Units in the Form of Braided Thread II

Hyaluronan monofilament fibers with Mw of $4.30 \times 10^5$ g/mol and a fineness in the range of 7.89 to 7.92 tex, prepared by a method known in the art (WO2012089179), and lauroyl HA fibers with a weight average molecular weight of $3.40 \times 10^5$ g/mol, fineness in the range of 7.63 to 8.49 tex and weight fraction of the substituent 13.69 wt %, prepared in a similar manner to Example 6, were used. From these fibers, a series of braided threads (textile units) were formed on a Steeger horizontal braiding machine, which contained a combination of hyaluronan fibers and lauroyl hyaluronan fibers, each containing a total of 24 fibers.

Example 13: Set of Textile Units in the Form of Braided Thread III

HA monofilaments with Mw of 4.30×10⁵ g/mol and a fineness in the range of 7.89 to 7.89 tex, prepared by a method known from the prior art (WO2012089179), and lauroyl HA fibers with Mw of 3.40×10⁵ g/mol, fineness in the range of 7.63 to 8.29 tex and weight fraction of substituent 13.69 wt %, prepared in a similar manner to Example 6 were used. A series of braided threads (textile units) containing a combination of hyaluronan fibers and lauroyl hyaluronan fibers was formed from these fibers on a Steeger horizontal braiding machine, each of which contained a total of 32 fibers.

Example 14: Swelling of a Dental Preparation in Saliva

Hyaluronan monofilaments prepared by a method known in the art (WO2012089179), lauroyl HA monofilaments prepared in a similar manner to Example 6 and palmitoyl HA monofilaments prepared by a similar procedure as in Example 7 were used. Mw of the fibers, fineness and, in the case of non-polar derivatives, the mass fractions of the substituent are given in Table 12. From these fibers, a series of braided threads were formed on a Steeger horizontal splicing machine containing a combination of HA fibers and non-polar HA fibers (lauroyl HA or palmitoyl HA) the individual fiber types being present in the threads in the same or different numbers; in total, each thread contained 16 fibers. The structural characteristics of the individual variants of the dental preparation in the form of a thread are given in Table 12. The values of the fiber weight ratio in the $P_{HA}:P_D$ thread were calculated according to the relations given in Example 11.

For each variant, the diameter of the thread in the dry state and the diameters of the thread after soaking in saliva for 20 minutes and 90 minutes were determined using an optical microscope. An example of the time course of swelling is recorded in the images in FIG. 3. The results are shown graphically in FIG. 6.

Example 15: Textile Units Containing Octenidine

Hyaluronan fibers prepared by a method known in the art (WO2012089179), lauroyl HA monofilament fibers prepared in a similar manner to Examples 5 and 6, and palmitoyl HA monofilament fibers prepared by a similar procedure as in Example 7 were used. Weight average molecular weights and in the case of non-polar derivatives, the weight fractions of the substituent are given in Table 13. From these fibers, a series of braided threads were formed on a Steeger horizontal splicing machine containing either one type of fiber or a combination of HA fibers and fibers of non-polar derivative of HA (lauroyl HA or palmitoyl HA). The threads each contained a total of 16 fibers. In the case of a combination of fibers, then the thread contained 8 fibers of HA and 8 fibers of a non-polar derivative of HA. The characteristics of the individual variants of textile units in the form of thread are given in Table 13.

TABLE 13

Characteristics of textile unit variants in the form of a thread containing hyaluronan fibers and non-polar hyaluronan derivative fibers.

| Thread variant | Material composition | Weight average molecular weight [g/mol] | Weight fraction of the substituent [wt %] | Fiber fineness [tex] | Thread diameter [μm] |
|---|---|---|---|---|---|
| A | Palmitoyl HA | $3.3 \times 10^5$ | 13.97 | 8.9 | 545 |
| B | Palmitoyl HA | $9.9 \times 10^5$ | 23.09 | 8.8 | 635 |
| C | Hyaluronan | $6.0 \times 10^5$ | — | 10.4 | 565 |
|   | Palmitoyl HA | $3.3 \times 10^5$ | 13.97 | 8.9 |  |
| D | Lauroyl HA | $9.9 \times 10^5$ | 10.26 | 4.4 | 468 |
| E | Lauroyl HA | $3.3 \times 10^5$ | 18.24 | 10.1 | 627 |
| F | Hyaluronan | $6.0 \times 10^5$ | — | 10.4 | 461 |
|   | Lauroyl HA | $9.9 \times 10^5$ | 10.26 | 4.4 |  |
| G | Hyaluronan | $6.0 \times 10^5$ | — | 10.4 | 573 |

Subsequently, each thread was divided into three sections, which were impregnated with an octenidine dihydrochloride solution at three different concentrations (2 mg/ml, 4 mg/ml, 6 mg/ml) using a Werner-Mathis laboratory horizontal foulard. Ethanol was used as the solvent. For all variants, the roller speed was set to 1 m/min and the identical roller pressure was 30%. This was followed by evaporation of the solvent at room temperature. The weight fraction of octenidine in the individual thread variants is given in Table 14.

TABLE 12

Characteristics of variants of a dental preparation in the form of a thread containing hyaluronan fibers and fibers of a non-polar hyaluronan derivative in different weight ratios.

| Variant | Material composition | Weight average molecular weight [g/mol] | Weight fraction of substituent [wt %] | Fiber fineness [tex] | Number of fibers in thread | Mass ratio of fibers $P_{HA}:P_D$ |
|---|---|---|---|---|---|---|
| A | Hyaluronan | $3.99 \times 10^5$ | N/A | 8.7 | 8 | 52:48 |
|   | Lauroyl HA | $3.4 \times 10^5$ | 13.11 | 7.9 | 8 |  |
| B | Hyaluronan | $3.99 \times 10^5$ | N/A | 8.3 | 4 | 24:76 |
|   | Lauroyl HA | $3.5 \times 10^5$ | 16.45 | 8.7 | 12 |  |
| C | Hyaluronan | $3.99 \times 10^5$ | N/A | 8.1 | 8 | 49:51 |
|   | Lauroyl HA | $3.5 \times 10^5$ | 16.36 | 8.4 | 8 |  |
| D | Hyaluronan | $3.99 \times 10^5$ | N/A | 8.3 | 12 | 74:26 |
|   | Lauroyl HA | $3.5 \times 10^5$ | 16.45 | 8.7 | 4 |  |
| E | Hyaluronan | $6.0 \times 10^5$ | N/A | 10.3 | 8 | 52:48 |
|   | Palmitoyl HA | $3.1 \times 10^5$ | 14.03 | 9.4 | 8 |  |

TABLE 14

Octenidine content in individual variants of the textile unit in the form of a thread at different concentrations of octenidine solution.

| Thread variant | Material composition (weight fraction of the substituent) | Weight fraction of octenidine [wt %] | | |
|---|---|---|---|---|
| | | 2 mg/ml | 4 mg/ml | 6 mg/ml |
| A | Palmitoyl HA (13.97 wt %) | 0.23 | 0.42 | 0.73 |
| B | Palmitoyl HA (23.09 wt %) | 0.22 | 0.41 | 0.64 |
| C | Palmitoyl HA (13.97 wt %) Hyaluronan | 0.21 | 0.35 | 0.87 |
| D | Lauroyl HA (10.26 wt %) | — | 0.56 | 0.98 |
| E | Lauroyl HA (18.24 wt %) | 0.19 | 0.35 | 0.59 |
| F | Hyaluronan Lauroyl HA (10.26 wt % | 0.22 | 0.35 | 0.69 |
| G | Hyaluronan | 0.20 | 0.36 | 0.67 |

Example 16: Distribution of Octenidine in Dental Preparation Containing Hyaluronan Fibers and Lauroyl Hyaluronan Fibers Hyaluronan monofilaments prepared by a method known in the art (WO2012089179) and lauroyl HA monofilaments prepared by a procedure similar to Examples 5 and 6 were used. Weight average molecular weight of the fibers, fineness and in the case of lauroyl HA weight fractions of the substituent are shown in Table 15. From these fibers, a series of braided threads were formed on a Steeger horizontal braiding machine, which contained a combination of hyaluronan fibers and hyaluronan lauroyl fibers, the different fiber types being represented in the threads in different numbers; in total, each thread contained 16 fibers. The characteristics of the individual fiber and thread variants are given in Table 15 and Table 16. The weight ratio of hyaluronan fibers to lauroyl HA fibers ($P_{HA}$:$P_D$) was calculated as in Example 14. The individual thread variants were then impregnated with octenidine dihydrochloride solution using a needle nozzle. The same concentration of octenidine 2.72 mg/ml in the solution was used for all variants. Ethanol was used as the solvent. A dosing rate of 0.1 ml/min was used for application. The thread was rewound at a speed of 2 m/min. The solvent was evaporated from the threads using plate infrared heaters. Subsequently, samples of impregnated threads were taken; these samples were unraveled, and the HA fibers and the lauroyl HA fibers were separated (the fibers are visually different). The weight fraction of octenidine was then determined for both types of fibers. The resulting values of the weight fraction of octenidine in the thread and in the individual fiber components are given in Table 16. The table also contains data on the distribution of octenidine among the fiber components of the individual thread variants. The relative amount of octenidine $RO_{HA}$ [wt %] in HA fibers and the relative amount of octenidine $RO_D$ Nit % in fibers of a non-polar derivative (lauroyl) based on the total weight fraction of octenidine $OKT_T$ [wt %] in the textile unit (threads) were calculated according to the relations $$RO_{HA}=OKT_{HA}\times P_{HA}/OKT_T,$$

and $$RO_D=OKT_D\times P_D/OKT_T,$$

where $OKT_{HA}$ [wt %] is the weight fraction of octenidine in the fibers from HA, $P_{HA}$ [wt %] is the weight fraction of hyaluronan fibers in the thread, $OKT_D$ [wt %] is the weight fraction of octenidine in the fibers from the non-polar derivative HA (here lauroyl HA) and $P_D$ [wt %] is the weight fraction of fibers of a non-polar HA derivative in the thread [wt %]. It is clear from the results that octenidine is preferentially deposited on fibers/into fibers of lauroyl HA, and to a lesser extent on fibers/into fibers of HA. Further commentary on these results is set forth herein.

TABLE 15

Characteristics of variants of a dental preparation in the form of a thread containing hyaluronan fibers and lauroyl hyaluronan fibers.

| Variant of dental preparation | Material composition | Weight average molecular weight [g/mol] | Weight fraction of the substituent [wt %] | Fiber fineness [tex] | Number of fibers in a thread | Thread diameter [μm] |
|---|---|---|---|---|---|---|
| A | Hyaluronan | $3.99 \times 10^5$ | — | 8.5 | 8 | 495* |
| | Lauroyl HA | $3.5 \times 10^5$ | 9.87 | 8.8 | 8 | |
| B | Hyaluronan | $3.99 \times 10^5$ | — | 8.6 | 8 | 483* |
| | Lauroyl HA | $3.2 \times 10^5$ | 12.98 | 8.9 | 8 | |
| C | Hyaluronan | $3.99 \times 10^5$ | — | 8.7 | 8 | 486* |
| | Lauroyl HA | $3.5 \times 10^5$ | 16.45 | 8.8 | 8 | |
| D | Hyaluronan | $3.99 \times 10^5$ | — | 8.2 | 4 | 498* |
| | Lauroyl HA | $3.5 \times 10^5$ | 16.45 | 8.7 | 12 | |
| E | Hyaluronan | $3.99 \times 10^5$ | — | 8.5 | 4 | 510** |
| | Lauroyl HA | $3.5 \times 10^5$ | 16.45 | 9.0 | 12 | |

*Thread diameter determined by laser scanner;
**Thread diameter determined using an optical microscope;

TABLE 16

Octenidine content in the thread and distribution of octenidine in its fiber components at different weight ratios of fibers in the thread and different weight fraction of substituent in lauroyl HA.

| Variant | Fiber component | Weight fraction of octenidine in a fiber [wt %] | Relative amount of octenidine in a fiber [wt %] | Weight fraction of octenidine in a thread [wt %] | Weight ratio of fibers $P_{HA}$:$P_D$ |
|---|---|---|---|---|---|
| A | Hyaluronan | 0.06 | 24 | 0.11 | 49:51 |
| | Lauroyl HA | 0.17 | 76 | | |
| B | Hyaluronan | 0.05 | 23 | 0.10 | 49:51 |
| | Lauroyl HA | 0.16 | 77 | | |
| C | Hyaluronan | 0.04 | 19 | 0.10 | 50:50 |
| | Lauroyl HA | 0.16 | 81 | | |

TABLE 16-continued

Octenidine content in the thread and distribution of octenidine
in its fiber components at different weight ratios of fibers in the
thread and different weight fraction of substituent in lauroyl HA.

| Variant | Fiber component | Weight fraction of octenidine in a fiber [wt %] | Relative amount of octenidine in a fiber [wt %] | Weight fraction of octenidine in a thread [wt %] | Weight ratio of fibers $P_{HA}:P_D$ |
|---------|-----------------|------------|------------|------------|------------|
| D | Hyaluronan | 0.03 | 7 | 0.10 | 24:76 |
| | Lauroyl HA | 0.13 | 93 | | |
| E | Hyaluronan | 0.06 | 51 | 0.08 | 74:26 |
| | Lauroyl HA | 0.16 | 49 | | |

Example 17: Antimicrobial Activity of an
Octenidine-Containing Dental Preparation Hyaluronan monofilament fibers with Mw of $3.99 \times 10^5$ g/mol and a fineness of 8.1 tex, prepared according to the prior art method (WO2012089179) and lauroyl HA fibers with Mw of $3.5 \times 10^5$ g/mol, with weight fraction of the substituent 13.7 wt % and a fineness of 9.2 tex, prepared in a similar manner to Examples 5 and 6 were used. From these fibers, a braided thread containing 8 HAfibers and 8 lauroyl HA fibers was formed on a Steeger horizontal braiding machine. The thread diameter determined by a laser scanner was 517 µm. Subsequently, the thread was divided into five sections, of which one was left as an octenidine-free control and four were impregnated with a solution of octenidine dihydrochloride in ethanol using a needle nozzle, followed by evaporation of the solvent using plate infrared heaters. Four different concentrations of octenidine and different dosing rates were used for loading. The thread was rewound at a speed of 1.9 m/min. In this way, five thread variants with different weight fractions of octenidine in the thread were obtained (see Table 17). The thread samples were then sterilized with ethylene oxide.

TABLE 17

Process parameters and octenidine content for
individual variants of the dental preparation.

| Preparation variant | Solution concentration [mg/ml] | Dosage [ml/min] | Weight fraction of octenidine [wt %] | Presence of inhibition zone |
|---------|-----------|-----------|-----------|-----------|
| A | — | — | 0.00 | NO |
| B | 1.75 | 0.1 | 0.07 | YES |
| C | 3.06 | 0.1 | 0.11 | YES |
| D | 2.72 | 0.15 | 0.15 | YES |
| E | 4.20 | 0.1 | 0.19 | YES |

The antimicrobial efficacy of dental preparations in the form of thread was tested by the method of inhibition zones on the *Aggregatibacter actinomycetemcomitans* strain. The prepared cell suspension was plated over the entire area on an agar Petri dish. Subsequently, three thread samples were placed on the agar. The plates were placed in an anaerostat with an anaerogen and subsequently incubated in a thermostat at 37° C. until they were overgrown with a continuous layer of culture.

Figure 5:
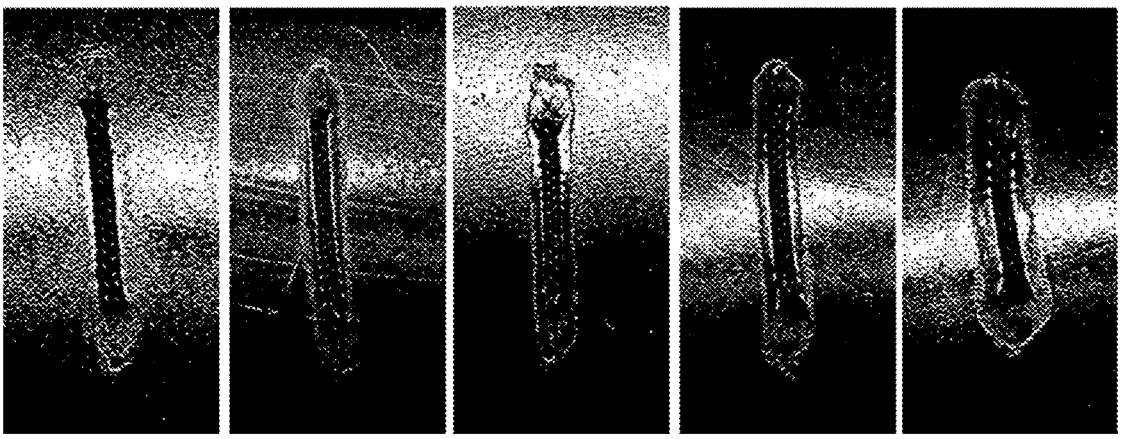
FIG. 5. Shows the results of an assay of textile units in the form of braided threads with different octenidine contents, prepared according to Example 15, tested against *Aggregatibacter actinomycetemcomitans*.

The antimicrobial efficacy of the dental preparation was evaluated according to the presence of the inhibition zone—if the inhibition zone was evident on all three thread samples placed on the agar plate, the variant was evaluated as effective (see FIG. 5 and Table 17).

Example 18: Octenidine-Containing Hyaluronan
Textile Units and their Safety In Vivo Hyaluronan monofilaments with Mw of $3.7 \times 10^5$ g/mol, a fineness of 8.3 tex, a strength of 0.9 N and a ductility of 10.8%, prepared by a method known from the prior art (WO2012089179), were used. From 8 of these fibers, a braided thread with a diameter of 380 µm (determined by means of an optical microscope) was formed on a Steeger horizontal braiding machine. Subsequently, the thread was divided into four sections, three of which were impregnated with a solution of octenidine dihydrochloride in ethanol at three different concentrations (1 mg/ml, 4 mg/ml, 10 mg/ml) using a Roaches horizontal laboratory foulard. Ethanol was used as the solvent. The roller speed of 2 m/min and the identical roller pressure of 3.5 bar were set for all variants. This was followed by evaporation of the solvent at room temperature. One section of thread was left as an octenidine-free control. In this way, four variants of the textile unit with different weight fractions of octenidine in the thread were created, which were subsequently sterilized with ethylene oxide. The content of octenidine in individual variants of the textile unit after sterilization is given in Table 18.

TABLE 18

Octenidine content in individual variants
of the hyaluronan textile unit at different
concentrations of octenidine solution.

| Variant of textile unit (thread) | Solution concentration [mg/ml] | Weight fraction of octenidine [wt %] |
|---------|-----------|-----------|
| A | 0 | 0.00 |
| B | 1 | 0.03 |
| C | 4 | 0.13 |
| D | 10 | 0.38 |

Variants of dental preparation A, B, C and D were implanted into the rabbit gum as follows. The rabbits were placed under total anesthesia. Subsequently, a 1.5-2.0 cm long incision was made on both sides of the mucosa of the alveolar ridge of the mandible in the area from the $2^{nd}$ incisor towards the distal. On both halves of the lower jaw, the tested textile unit was inserted into the gums at the site of the mucosal incision according to the animal's belonging to the experimental group, i.e. 1 cm long thread. Subsequently, mucosal sections were sutured using non-absorbable sutures (Premilene). The rabbits were divided into 4 groups, with only one variant of the textile unit in the form of a thread with octenidine being implanted in each group. Rabbits were sacrificed 14 days after insertion. Histological examination of the gums in control group A confirmed the presence of a reparative process at the incision site (newly formed connective tissue). The same finding was repeated in rabbits implanted with a dental preparation containing octenidine (variants B, C and D). No residue of the test preparation was detected in any of these samples. Furthermore, no negative reaction to the presence of the tested preparation was found, or the antiseptic used, even at the highest weight fraction in the thread.

Example 19: Set of Two Textile Units Containing Lauroyl HA Fibers with Different Substituent Content, their Safety and Biodegradation In Vivo A) Upper Textile Unit Hyaluronan monofilament fibers with Mw of $3.7 \times 10^5$ g/mol and a fineness of 8.3 tex, prepared according to the prior art method (WO2012089179), and HA lauroyl fibers described in Example 6 were used. A braided thread was created on a horizontal braiding machine Steeger which contained 8 fibers of HA and 8 fibers of lauroyl HA. The thread diameter was 537 μm (determined using an optical microscope). Subsequently, the thread was impregnated with a Roaches laboratory horizontal foulard with a 2 mg/ml solution of octenidine dihydrochloride in ethanol, followed by evaporation of the solvent at room temperature. The roller speed was set at 2 m/min and the roller pressure was 3.5 bar. The resulting weight fraction of octenidine in the thread after evaporation of the solvent was 0.13 wt %. The thread was then sterilized with ethylene oxide.

B) Bottom Textile Unit

Hyaluronan monofilament fibers with Mw of $3.7 \times 10^5$ g/mol and a fineness of 8.5 tex, prepared according to the prior art method (WO2012089179), and HA lauroyl fibers described in Example 5 were used. The Steeger braiding machine produced a braided thread which contained 8 HA fibers and 8 lauroyl HA fibers. The thread diameter was 501 μm (determined using an optical microscope). Subsequently, the thread was impregnated with a Roaches laboratory horizontal foulard with a 2 mg/ml solution of octenidine dihydrochloride in ethanol, followed by evaporation of the solvent at room temperature. The roller speed was set at 2 m/min and the roller pressure was 3.5 bar. The resulting weight fraction of octenidine in the thread after evaporation of the solvent was 0.11 wt %. The thread was then sterilized with ethylene oxide.

Samples A and B were implanted into the gums of the rabbit as described in Example 18. Two weeks after insertion of the test dental preparation into the gums, the animals were placed under total anesthesia and blood was collected. Subsequently, the animals were sacrificed by overdose of total anesthetics and macroscopic examination of the mandible was performed at the sites where the test preparation was inserted into the gums. Gum samples and any remaining implant material were then taken from the mandible for histological examination and chemical analysis (degradation evaluation). Gum samples were processed using a cryometer. The slides were treated with mounting medium Tissue-Tek o.c.t. and then frozen at −19° C. All slides were stained with hematoxylin and eosin.

In rabbits implanted with the upper textile unit (variant A), a gel-like mass was found at the site of application of the test preparation, which still maintained a certain cohesion and could be stretched to the original shape of the fiber. Subsequent chemical analysis confirmed that they were residues of a textile unit (thread) containing partially degraded lauroyl HA. Histological examination of the gums of the rabbits confirmed the persistence of the test preparation at the site of application.

In rabbits implanted with the bottom textile unit (variant B), no residues of the implanted textile unit (thread) were found at the site of application of the test preparation. Histological examination of the rabbit gum confirmed the presence of eosinophilic cells. The preparation itself was not found.

An in vivo test confirmed that the upper and bottom textile units degraded differently. A unit containing lauroyl HA fibers with a higher weight fraction of substituent (bound lauroyl) was found at the implantation site even after 2 weeks, while a unit with a lower weight fraction of substituent in lauroyl HA was already absorbed. These results correspond to the determination of the rate of enzymatic degradation of lauroyl HA fibers in vitro (see values in Examples 5 and 6). The test results indicate that the tested preparation has no negative effect on the animal's internal organs or on the soft tissues in its vicinity.

Example 20: Set of Three Textile Units Containing Lauroyl HA Fibers with Different Substituent Content, their Safety and Biodegradation In Vivo A) Upper Textile Unit Hyaluronan monofilament fibers with Mw of $3.99 \times 10^5$ g/mol and a fineness of 8.2 tex, prepared by a method known in the art (WO2012089179), and lauroyl HA fibers with Mw of $3.5 \times 10^5$ g/mol, weight fraction of the substituent 16.36 wt % and a fineness of 8.6 tex, prepared in a similar manner to Example 6 were used. The rate of enzymatic degradation of lauroyl HA fibers under in vitro conditions, determined by procedure described in Example 5, was 8.9 wt %/hour (evaluation from samples taken at times of 3-12 hours, until $3^{rd}$ hour the degradation was very slow and there was mostly just swelling of the fibers). A braided thread containing 8 HA fibers and 8 lauroyl HA fibers was formed from the fibers on a Steeger horizontal braiding machine. The thread diameter determined by the laser scanner was 515 μm. Subsequently, the thread was impregnated with a 2.72 mg/ml octenidine dihydrochloride solution using a needle nozzle. Ethanol was used as the solvent. A dosing rate of 0.1 ml/min was used for application. The thread was rewound at a speed of 1.9 m/min. The solvent was evaporated from the threads using plate infrared heaters. The thread was sterilized with ethylene oxide. The weight fraction of octenidine in the thread after sterilization was 0.11 wt %.

B) Middle Textile Unit

Hyaluronan monofilament fibers with Mw of $3.99 \times 10^5$ g/mol and a fineness of 8.2 tex, prepared by a method known in the art (WO2012089179), and lauroyl HA fibers with a Mw of $3.2 \times 10^5$ g/mol, with weight fraction of the substituent 12.98 wt % and a fineness of 9.3 tex, prepared in a manner similar to Examples 5 and 6, were used. The rate of enzymatic degradation of lauroyl HA fibers under in vitro conditions, determined by the procedure described in Example 11, was 10.4 wt %/hour (evaluation performed on samples taken at time points within 3-10 hours, until the $3^{rd}$ hour the degradation was very slow and there was mostly just swelling of the fibers). A braided thread containing 8 HA fibers and 8 lauroyl HA fibers was formed from the fibers on a Steeger horizontal braiding machine. The thread diameter determined by the laser scanner was 501 μm. Subsequently, the thread was impregnated with a 3.06 mg/ml octenidine dihydrochloride solution using a needle nozzle. Ethanol was used as the solvent. A dosing rate of 0.1 ml/min was used for application. The thread was rewound at a speed of 1.9 m/min. The solvent was evaporated from the threads using plate infrared heaters. The thread was sterilized with ethylene oxide. The weight fraction of octenidine in the thread after sterilization was 0.11 wt %.

C) Bottom Textile Unit

Hyaluronan monofilament fibers with Mw of $3.99 \times 10^5$ g/mol and a fineness of 8.2 tex, prepared by a method known in the art (WO2012089179), and lauroyl HA fibers with Mw of $3.5 \times 10^5$ g/mol, by weight of the substituent 9.87 wt % and a fineness of 8.9 tex, prepared in a similar manner to Example 5, were used. The rate of enzymatic degradation of lauroyl HA fibers under in vitro conditions, determined by the procedure described in Example 11, was 32.3 wt %/hour (evaluation performed on samples taken at time points within 0-3 hours, swelling did not occur for these rapidly degrading fibers). A braided thread containing 8 HA fibers and 8 lauroyl HA fibers was formed from the fibers on a Steeger horizontal braiding machine. The thread diameter determined by the laser scanner was 503 μm. Subsequently, the thread was impregnated with a 2.92 mg/ml octenidine dihydrochloride solution using a needle nozzle. Ethanol was used as the solvent. A dosing rate of 0.1 ml/min was used for application. The thread was rewound at a speed of 1.9 m/min. The solvent was evaporated from the threads using plate infrared heaters. The thread was sterilized with ethylene oxide. The weight fraction of octenidine in the thread after sterilization was 0.12 wt %.

The textile units A, B and C were implanted into the gums of the rabbit as described in Example 18. However, in this case all 3 tested textile units (i.e. a set of three threads) were inserted into the mucosa, from each variant a section of thread 1 cm long, thus a total of 3 cm of dental preparation on each side of the lower jaw.

In each group of rabbits, the dental preparation was left in the gums for different periods of time from implantation, namely 2 days, 2 weeks, 4 weeks and 6 weeks. Subsequently, examinations were performed and samples were collected as described in Example 19.

Histological examination of rabbits with collection after 2 days showed the presence of the tested dental preparation, both in the form of intact fibers (probably variant A and B) and in the form of material residues in the intercellular mass (probably variant C). Similar results were obtained in rabbits taken after 2 weeks, when a thread containing almost intact fibers and at the same time fiber residues in their immediate vicinity was again detected on the histological specimen (see FIG. 4*a*). In the groups where the collection was performed after 4 weeks and after 6 weeks, the tested dental preparation was no longer found in any of the preparations, but only the multiplication of the reparative tissue at the site of application of the material (see FIG. 4*b*). The insertion site of the dental preparation was healed ad integrum. The surroundings of the implanted dental device did not show any signs of an inflammatory reaction, or any other damage. Histologically, it was shown that the test material certainly lasted for 2 weeks, on the other hand, when checked at 4 weeks, it was already fully resorbed and only reparative tissue was at the application site. After 6 weeks, the application site was fully healed.

Example 21: Comparison of a Dental Preparation in the Form of a Thread with a Dental Preparation in the Form of a Gel in In Vivo Testing For a comparative in vivo test in a rabbit model, the dental preparation according to the present embodiments in the form of a set described in Example 20 and the commercial dental preparation Pocket-X® Gel (Prudentix Ltd, Israel) based on WO18158764 were used, which according to the package leaflet contained purified water, poloxamer 407, phenoxyethanol, hyaluronic acid (0.8%) and octenidine hydrochloride (0.625%).

One week before the actual implantation of the dental preparations, the pockets were created in the animals in the upper and lower jaws as follows: The rabbits were placed under general anesthesia. Subsequently, a mucosal incision was made on their upper and lower jaws, starting at the tip of the alveolar ridge in the area distal to the left incisor, at the level of the left incisor the incision was wound vestibularly, and was guided in the gingival sulcus of the left and right incisors and then wound distally of right incisor again on the tip of the alveolar ridge. The lobe thus formed was unfolded and the alveolar bone of the jaw was exposed. Using a micromotor with a circle-shaped carbide drill, approx. 2 mm vestibular lamellae of the alveolar bone of the jaw covering the cervical part of the tooth roots were lowered and a retraction fiber (commonly used material in dentistry) was inserted into the wound (to the ground bone). The task of the retraction fiber was to prevent the gingiva from reattaching to the tooth, thus helping to create an environment in which the internal soft tissue inside the formed pocket is infected with its own bacteria commonly present in the rabbit cavity, covered with granulation tissue, simulating the internal environment of the periodontal pocket. After inserting the retraction fiber, the formed lobe was placed back in its original position and fixed on the sides, and in the interdental space of the incisors by non-absorbable suturing. After 1 week, the animals were placed under total anesthesia, in which the retraction fiber was removed, and dental preparation was inserted into the resulting pocket on both jaws according to the individual tested groups (5 animals in a group for each preparation). In the case of the dental preparation according to the invention, these were three different textile units (bottom, middle and upper) in the form of a thread with a length of 1 cm, i.e. a total of 6 cm, or. 7.5 mg per animal. Pocket X-Gel was dispensed using a syringe in accordance with the instructions given in its package leaflet, so that the pocket was gradually filled to the brim with gel. Approximately 35 μl of gel was applied to each pocket, for a total of approximately 70 μl of gel per animal After inserting the dental preparation into the pocket, the lobe was fixed with a suture in the interdental space of the incisors by non-absorbable suturing. In the case of the dental preparation according to the invention, the application was easy and accurate. The threads were simply inserted with tweezers into the pocket, where they adhered to the moist surface of the mucosa and remained there; were not pushed out by the movement of the jaw or the abrasion of the gums against the inside of the lips. In contrast, the application of Pocket-X® Gel was quite demanding. Due to the high viscosity, the gel was difficult to push into the pocket with a syringe. In the pocket, however, the gel did not adhere sufficiently to the mucosa nor did it solidify enough to remain in place after the gums adhered to the tooth Immediately after implantation of the gel, it was noted that the gel is expelled from the pocket and flows out. When checking the applied site 3 hours after application, the gel was no longer found in some animals.

At 48 hours postoperatively, the animals were placed under total anesthesia. Subsequently, a macroscopic examination and photo documentation of the areas in the upper and lower jaw where the test specimen was inserted was performed. Thereafter, the animals were sacrificed by overdosing on the total anesthetic and tissue samples were taken at the site of implantation, including any remaining implanted dental device from one jaw to assess material degradation.

The pockets in the upper and lower jaws of rabbits showed inflammation before implantation of the dental preparations and a fibrin coating was present. When the animals were examined after 48 hours, the gums of the upper jaw at the site of the pocket were already grown, both in rabbits from the group with the dental preparation according to the present embodiments and in rabbits with Pocket-X® Gel. However, significant differences between the groups were evident in the condition of the pockets in the mandible. In the case of the dental preparation in the form of a thread according to the invention, the pockets were completely free of inflammation, the tissue was pink and perfused, the healing process was not disturbed in any way. In animals treated with Pocket-X® Gel, pus, a milky gel mass was present in the pockets of the mandible, and a fibrin coating persisted in one rabbit.

Example 22: Hyaluronan Textile Unit Containing Chlorhexidine

Hyaluronan monofilaments with Mwof $4.3\times10^5$ g/mol and a fineness of 7.3 tex, prepared according to a method known from the prior art (WO2012089179) were used. From these 16 fibers, a braided thread with a diameter of 433 μm (determined using an optical microscope) was formed on a Steeger horizontal braiding machine. Subsequently, each thread was divided into two sections, which were impregnated with a needle nozzle solution of a chlorhexidine solution of two different concentrations, namely 2.72 mg/ml and 3.40 mg/ml. Acetonitrile was used as the solvent. A dosing rate of 0.1 ml/min was used for application. The thread was rewound at a speed of 1.95 m/min. The solvent was evaporated from the threads using plate infrared heaters. The resulting weight fraction of chlorhexidine in the thread was 0.11 wt % for a concentration of 2.72 mg/ml and 0.18 wt % for a concentration of 3.40 mg/ml.

Example 23: Hyaluronan and Lauroyl Hyaluronan Textile Unit Containing Chlorhexidine Hyaluronan monofilaments with Mw of $3.99\times10^5$ g/mol and a fineness of 7.7 tex prepared by a prior art method (WO2012089179) and lauroyl HA monofilaments with a weight average molecular weight of $3.4\times10^5$ g/mol, with weight fraction of the substituent 10.86 wt % and fineness 8.6 tex, prepared in a similar manner to Example 5, were used. A braided thread containing 8 hyaluronan fibers and 8 lauroyl HA fibers was formed on a Steeger horizontal braiding machine. The thread had a diameter of 488 μm. Subsequently, the thread was impregnated with a chlorhexidine solution having a concentration of 2.72 mg/ml using a needle nozzle. Acetonitrile was used as the solvent. A dosing rate of 0.1 ml/min was used for application. The thread was rewound at a speed of 1.9 m/min. The solvent was evaporated from the threads using plate infrared heaters. The resulting weight fraction of chlorhexidine in the thread was 0.10 wt %.

Example 24: Effect of Rewinding Speed on Chlorhexidine Coating on Thread

Hyaluronan monofilaments with Mw of $3.99\times10^5$ g/mol and a fineness of 7.7 tex prepared by a prior art method (WO2012089179) and lauroyl HA monofilaments with a Mw of $3.4\times10^5$ g/mol, with mass fraction of the substituent 13.11 wt % and a fineness of 7.9 tex, prepared in a similar manner to Example 5, were used. A braided thread containing 8 hyaluronan fibers and 8 lauroyl HA fibers was formed on a Steeger horizontal braiding machine. The thread had a diameter of 471 μm. Subsequently, the thread was divided into three sections, which were then impregnated with a chlorhexidine solution having a concentration of 2.72 mg/ml using a needle nozzle. Acetonitrile was used as the solvent. A dosing rate of 0.1 ml/min was used for coating. During application, the individual sections were rewound at different speeds, namely 1.6 m/min, 1.7 m/min and 2.2 m/min. The solvent was evaporated from the threads using plate infrared heaters. The resulting weight fraction of chlorhexidine in the thread was 0.18 wt % for a speed of 1.6 m/min, 0.14 wt % for a speed of 1.7 m/min and 0.10 wt % for a speed of 2.2 m/min.

Example 25: Synthesis of Hyaluronan Chloramide 10 g of hyaluronan with Mw of $9\times10^5$ g/mol were dissolved in 1000 ml of distilled water. Then 6 ml of acetic acid were added and after stirring for 15 minutes at 20° C., 0.3 equivalents of sodium dichloroisocyanuric acid was added. The mixture was then stirred at ° C. for 20 hours, then precipitated with 5 liters of isopropanol and filtered. The solid was washed with 2 liters of isopropanol and dried under vacuum for 20 hours. The resulting weight fraction of the substituent was 4.1 wt % (DS according to NMR 48%), weight average molecular weight $5\times10^5$ g/mol.

Example 26: Synthesis of Hyaluronan Chloramide with Low Fraction of Substituent 10 g of hyaluronan with Mw of $5\times10^5$ g/mol were dissolved in 1000 ml of distilled water. Then 6 ml of acetic acid were added and after stirring for 15 minutes at 20° C., 0.05 equivalents of sodium dichloroisocyanuric acid was added. The mixture was then stirred at ° C. for 20 hours, then precipitated with 5 liters of isopropanol and filtered. The solid was washed with 2 liters of isopropanol and dried under vacuum for 20 hours. The resulting weight fraction of the substituent was 0.6 wt % (DS according to NMR 7%), weight average molecular weight $1.9 \times 10^5$ g/mol.

Example 27: Chloramide Fiber

Hyaluronan chloramide prepared according to Example 25 was used as a starting material for fiber formation. By dissolving 2.5 g of this polymer in 50 ml of demineralized water, a solution with a concentration of 50 mg/ml was prepared. After reconstitution, the solution was transferred to a syringe and degassed with centrifuge. The solution was metered at a rate of 200 μl/min into a 1:4 lactic acid-isopropanol precipitation bath. The fiber was wound at a speed of 1.47 m/min. Subsequently, the fiber was washed in ethanol and dried. The fineness of the fiber was 7.9 tex, the strength 1.2 N and the ductility 21%.

weight fraction of substituent 7.0 wt. % (DS according to NMR 85%), prepared according to CZ308010 (Example 18), and lauroyl hyaluronan with a weight average molecular weight of $3.3 \times 10^5$ g/mol and a weight fraction of substituent of 17.13%, prepared in a similar manner to Example 3, were used for fiber formation as starting material. Solutions of a concentration of 50 mg/ml with different weight ratios of polymer components contained were prepared by dissolving both polymers in a demineralized water—isopropanol mixture (component weights, their weight fractions and solvent volumes see Table 19). After reconstitution, each solution was transferred to a syringe and degassed by centrifugation. The solution was then metered using a nozzle at a rate of 200 μl/min into a 1:4 lactic acid/isopropanol precipitating bath. The fiber was wound at a speed of 1.32 m/min Subsequently, the fiber was washed first in ethanol, then in acetone and finally dried. The physical properties of the individual fiber variants are given in Table 19.

TABLE 19

| | | | Weight | Solvent | | | |
|---|---|---|---|---|---|---|---|
| | | Weight | fraction in the | volume | Fineness | Strength | Ductility |
| Fiber | Polymer component | [g] | fiber [wt %] | [ml] | [tex] | [N] | [%] |
| A | Chloramid HA | 1.17 | 33 | 70 | 9.0 | 0.4 | 12 |
| | Lauroyl HA | 2.34 | 67 | | | | |
| B | Chloramid HA | 1 | 40 | 50 | 9.7 | 0.5 | 8 |
| | Lauroyl HA | 1.5 | 60 | | | | |
| C | Chloramid HA | 1.25 | 50 | 50 | 8.7 | 0.4 | 3 |
| | Lauroyl HA | 1.25 | 50 | | | | |

Process parameters and physical characteristics of mixed chloramide fibers

Example 28: Chloramide Fiber with Low Substituent Content

Hyaluronan chloramide prepared according to Example 26 was used as a starting material for fiber formation. By dissolving 3.5 g of this polymer in 70 ml of demineralized water, a solution having a concentration of 50 mg/ml was prepared. After reconstitution, the solution was transferred to a syringe and degassed by centrifuge. The solution was metered by means of a nozzle at a rate of 200 μl/min into a precipitating bath consisting of a mixture of lactic acid—isopropanol in a ratio of 1:4. The fiber was wound at a speed of 1.47 m/min Subsequently, the fiber was washed in ethanol and dried. The fineness of the fiber was 7.2 tex, the strength 1.1 N and the ductility 8%.

Example 29: Mixed Chloramide Fibers of Hyaluronan Chloramide and Hyaluronan Lauroyl In the following way, three variants of mixed chloramide fiber with different weight fraction of hyaluronan chloramide in the fiber were created. Hyaluronan chloramide with a weight average molecular weight of $3.8 \times 10^5$ g/mol and a

Example 30: Mixed Chloramide Fibers of Hyaluronan Chloramide and Hyaluronic Acid In the following way, four variants of a mixed chloramide fiber with different weight fractions of HA chloramide in the fiber were created. Hyaluronan chloramide with Mw of $7.8 \times 10^4$ g/mol and a weight fraction of the substituent of 7.9 wt. % (DS according to NMR 96%), prepared according to CZ308010 (Example 10), and HA with Mw of $3.99 \times 10^5$ g/mol, were used as starting material for fiber formation. Solutions of 50 mg/ml with different weight ratios of polymer components contained were prepared by dissolving both polymers in demineralized water (see Table 20 for component weights, solvent weight and solvent volumes). After dissolution, each solution was transferred to a syringe and degassed by centrifugation. The solution was then metered through a nozzle at a rate of 200 μl/min into a 1:4 lactic acid-isopropanol precipitating bath, the fiber was wound at a speed of 1.47 m/min, then the fiber was washed in ethanol and finally dried. Physical properties of individual variants of the fibers are listed in Table 20.

TABLE 20

Process parameters and physical characteristics of mixed chloramide fibers

| Fiber | Polymer | Weight [g] | Weight fraction in the fiber [wt %] | Solvent volume [ml] | Fineness [tex] | Strength [N] | Ductility [%] |
|---|---|---|---|---|---|---|---|
| A | Chloramid HA | 1.17 | 33 | 70 | 7.6 | 0.5 | 12 |
|  | HA | 2.34 | 67 |  |  |  |  |
| B | Chloramid HA | 1 | 40 | 50 | 8.4 | 0.7 | 15 |
|  | HA | 1.5 | 60 |  |  |  |  |
| C | Chloramid HA | 1.25 | 50 | 50 | 8.4 | 0.6 | 13 |
|  | HA | 1.25 | 50 |  |  |  |  |
| D | Chloramid HA | 1.5 | 60 | 50 | 8.3 | 0.8 | 10 |
|  | HA | 1 | 40 |  |  |  |  |

Example 31: Textile Units Containing Hyaluronan Chloramide

Hyaluronan monofilament fibers with Mw of $4.3 \times 10^5$ g/mol, prepared by a method known in the art (WO2012089179), lauroyl HA monofilament fibers with a weight average molecular weight of $3.3 \times 10^5$ g/mol, prepared by a similar manner to Examples 5 and 6, the chloramide fibers prepared according to Example 27, mixed chloramide fibers with a weight fraction of chloramide HA in the fiber of 33 wt % and mixed chloramide fibers with a weight fraction of chloramide HA in the fiber of 40 wt %, prepared according to Example 27 and mixed chloramide fibers with a weight fraction of HA chloramide in the fiber of 60 wt %, prepared according to Example 28 were used. From these fibers, a series of braided threads (textile units) were formed on a Steeger horizontal braiding machine, which contained a combination of chloramide fibers or mixed chloramide fibers and hyaluronan fibers or lauroyl hyaluronan fibers; in total, each thread contained 16 fibers. $P_{CV}$ mass fraction values [wt %] of chloramide fibers and mixed chloramide fibers in the textile unit (threads) were calculated according to the relations:

$$P_{CV} = N_{CV} \times T_{CV}/(N_{CV} \times T_{CV} + N_{HA} \times T_{HA}) \times 100, \text{ and}$$
$$P_{CV} = N_{CV} \times T_{CV}/(N_{CV} \times T_{CV} + N_D \times T_D) \times 100,$$

where $N_{CV}$ is the number of chloramide or mixed chloramide fibers in the thread, $T_{CV}$ is the fineness of chloramide or mixed chloramide fibers in the thread, $N_{HA}$ is the number of HA fibers in the thread, $T_{HA}$ is the fineness of HA fibers, $N_D$ is the number of HA non-polar derivatives (here lauroylu HA) in the thread and $T_D$ is the fineness of the fibers from the non-polar derivative of HA (here lauroyl HA). $P_{CT}$ weight fraction values [wt %] of the chloramide derivative HA in the textile unit—the threads were calculated according to the relation $$P_{CT} = P_{CI} \times P_{CV}/100,$$

where $P_{CI}$ [wt %] is the weight fraction of the chloramide derivative HA in the fiber. The characteristics of the fibers and threads, including the resulting mass fraction of chloramide derivative in the textile unit—threads, are given in Table 21 and Table 22.

TABLE 21

Textile units containing chloramide or mixed chloramide fibers—characteristics of fibers and threads.

| Textile unit | Material composition of the fibers, (weight fraction of the substituent in the derivative—chlorine or lauroyl) | $P_{CI}$—weight fraction of chloramide HA in the fiber [wt %] | Fineness of the fiber [tex] | Number of fibers in a thread |
|---|---|---|---|---|
| A | Hyaluronan | — | 7.3 | 8 |
|  | Chloramid HA (4.1 wt %) | 100 | 7.9 | 8 |
| B | Lauroyl HA (13.51 wt %) | — | 8.6 | 8 |
|  | Chloramid HA (7 wt %) + Lauroyl HA (17.13 wt %) | 40 | 9.7 | 8 |
| C | Lauroyl HA (17.08 wt %) | — | 8.2 | 12 |
|  | Chloramid HA (7 wt %) + Lauroyl HA (17.13 wt %) | 33 | 9.0 | 4 |
| D | Lauroyl HA (17.08 wt %) | — | 8.2 | 8 |
|  | Hyaluronan + Chloramid HA (7.9 wt %) | 60 | 8.3 | 8 |

TABLE 22

Textile units containing chloramide or mixed chloramide fibers.

| Textile unit | Material composition of the fibers, (weight fraction of the substituent in the derivative—chlorine or lauroyl) | Pcv—weight fraction of (mixed) chloramide fibers in textile unit [wt %] | $P_{CT}$—weight fraction of chloramide HA in textile unit [wt %] |
|---|---|---|---|
| A | Hyaluronan Chloramid HA (4.1 wt %) | 52 | 52 |
| B | Lauroyl HA (13.51 wt %) Chloramid HA (7 wt %) + Lauroyl HA (17.13 wt %) | 53 | 21 |
| C | Lauroyl HA (17.08 wt %) Chloramid HA (7 wt %) + Lauroyl HA (17.13 wt %) | 27 | 9 |
| D | Lauroyl HA (17.08 wt %) Hyaluronan + Chloramid HA (7.9 wt %) | 50 | 30 |

Phases of healing of the periodontal pocket by means of a dental preparation according to the present embodiments is shown in FIG. 1a-FIG. 1d. In more detail, FIG. 1a illustrates textile units in the form of thread with different degradation rates inserted into the periodontal pocket; FIG. 1b illustrates formation of periodontal ligaments at the bottom of the pocket; FIG. 1c illustrates formation of periodontal ligaments in the middle part of the pocket and growth of alveolar bone; and FIG. 1d illustrates a healed periodontium.

Dental preparations of the present embodiments in the form of thread and in the form of a strip of fabric are shown in FIG. 2a-FIG. 2b. In more detail, FIG. 2a illustrates a dental preparation in the form of a braided thread according to the present embodiments, comprising 8 fibers of hyaluronan and 8 fibers of a non-polar hyaluronan derivative (lauroyl HA, weight fraction of substituent 16.36 wt %) with a weight fraction of octenidine in the thread 0.11 wt %, prepared according to Example 18 (upper textile unit). FIG. 2b illustrates a textile unit of a dental preparation in the form of a strip of fabric (warp knitted fabric) according to the present embodiments, comprising fibers of a non-polar hyaluronan derivative (lauroyl HA, weight fraction of substituent 14.41 wt %), prepared according to Example 10 (upper textile unit).

Figure 3C:
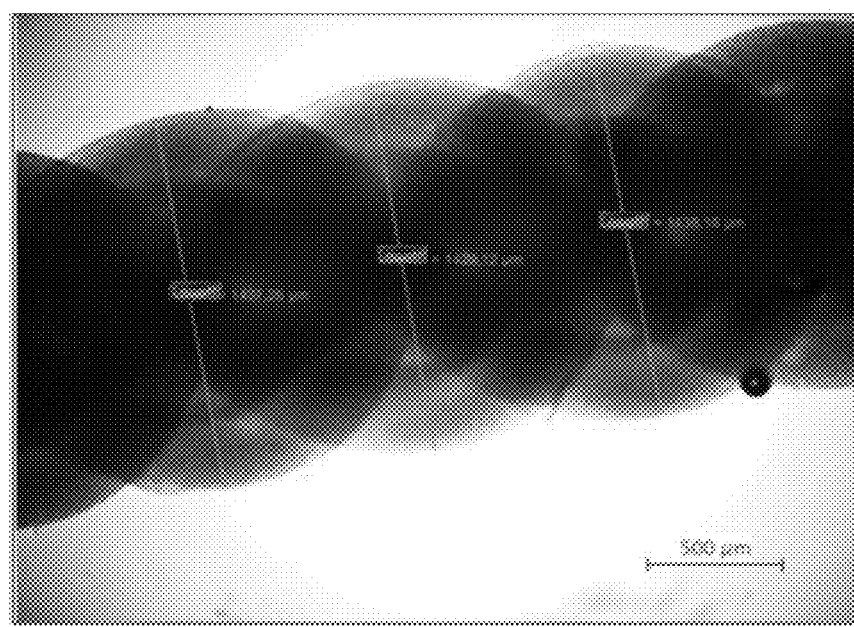

Dental preparations of the present embodiments in the form of a braided thread are shown in FIG. 3a— FIG. 3c. The braided thread comprises 8 fibers of hyaluronan and 8 fibers of a non-polar derivative of hyaluronan (lauroyl HA, weight fraction of substituent 16.36 wt %), prepared according to Example 12 (variant C). In more detail, FIG. 3a shows the thread in dry state. FIG. 3b shows the thread after swelling in saliva at a time of 20 min. FIG. 3c shows the thread after swelling in saliva in a time of 90 min.

Figure 4A:
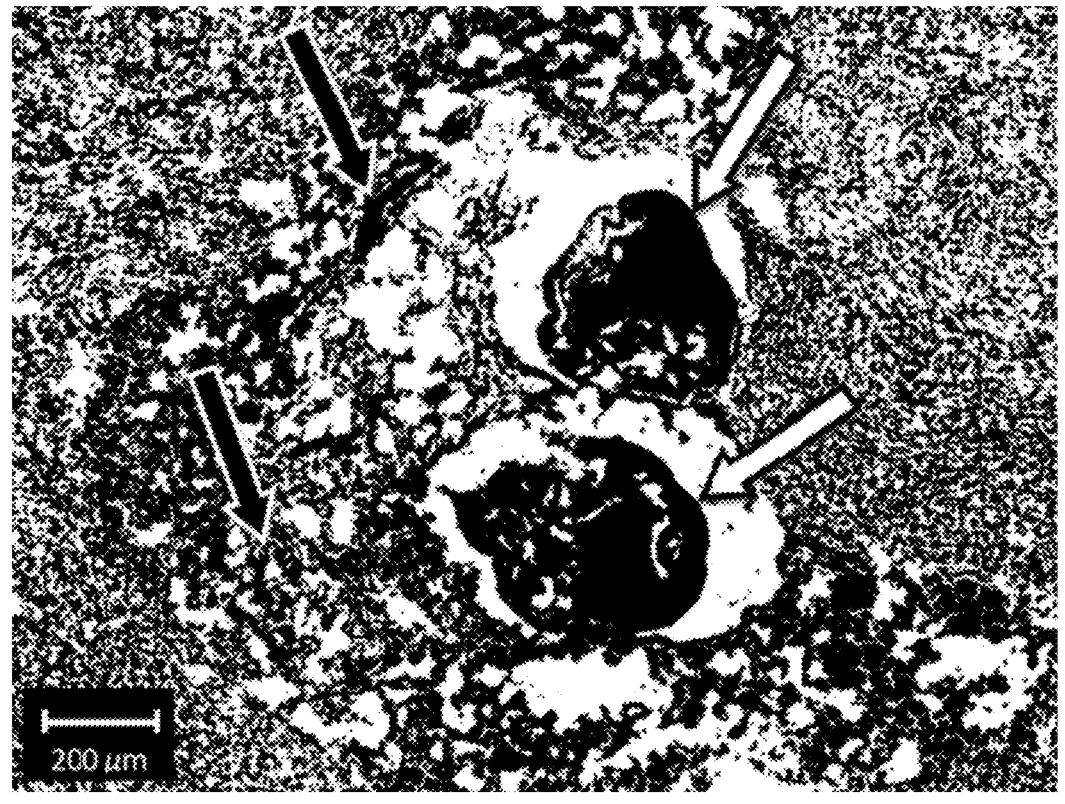
FIG. 4a— FIG. 4b show histological preparations of a set of textile units in the form of plaited threads prepared according to Example 18, following implantation in the gums of a rabbit, with FIG. 4a showing a histological specimen after 14 days following implantation, and FIG. 4b showing a histological specimen after 4 weeks following implantation.
Figure 4B:
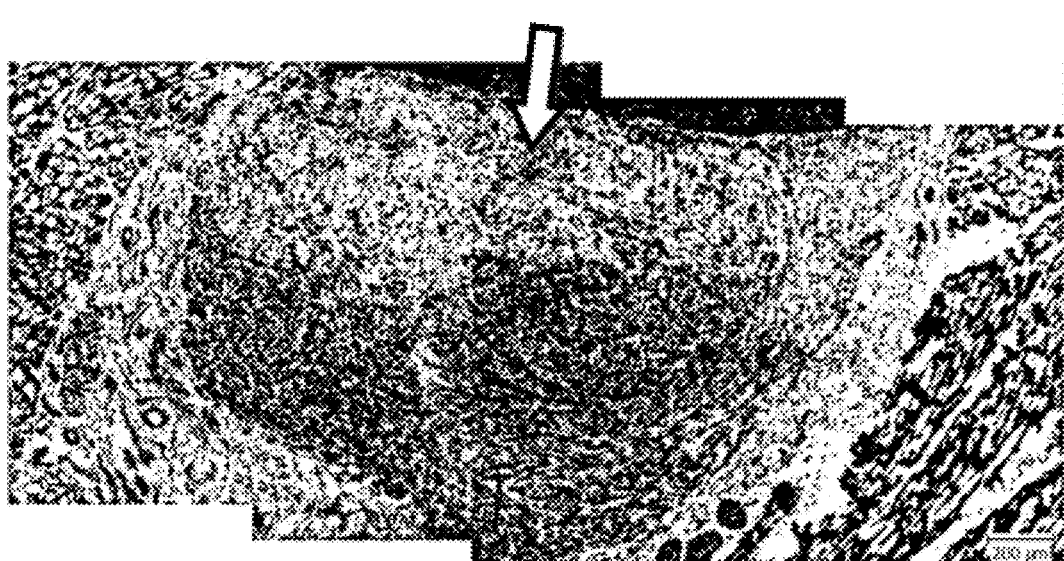

Dental preparations of the present embodiments, as a set of textile units in the form of plaited thread, are used to prepare the histological preparations shown in FIG. 4a— FIG. 4b. The plaited thread comprises hyaluronan fibers and hyaluronan lauroyl fibers of various weight fractions of the substituent, containing, octenidine dihydrochloride, and is prepared according to Example 18. In more detail, FIG. 4a represents a histological preparation after 14 days of implantation in the gums of a rabbit, proving the presence of a dental preparation according to the present embodiments. The cross-sectional areas of the still compact lauroyl hyaluronan fibers (probably top and middle unit residues) are shown with white arrows, the area with fiber residues that are almost degraded is shown with black arrows. FIG. 4b represents a histological specimen after 4 weeks of implantation in rabbit gums. Residues of fibers of the dental preparation are no longer present. In the composite image, healing tissue is present at the site of application of the dental product (marked by an arrow).

Textile units in the form of braided threads with different octenidine contents, prepared according to Example 15, are tested on the *Aggregatibacter actinomycetemcomitans* strain. The results, in the form of inhibition zones around the textile units, are shown in FIG. 5.

Figure 6:
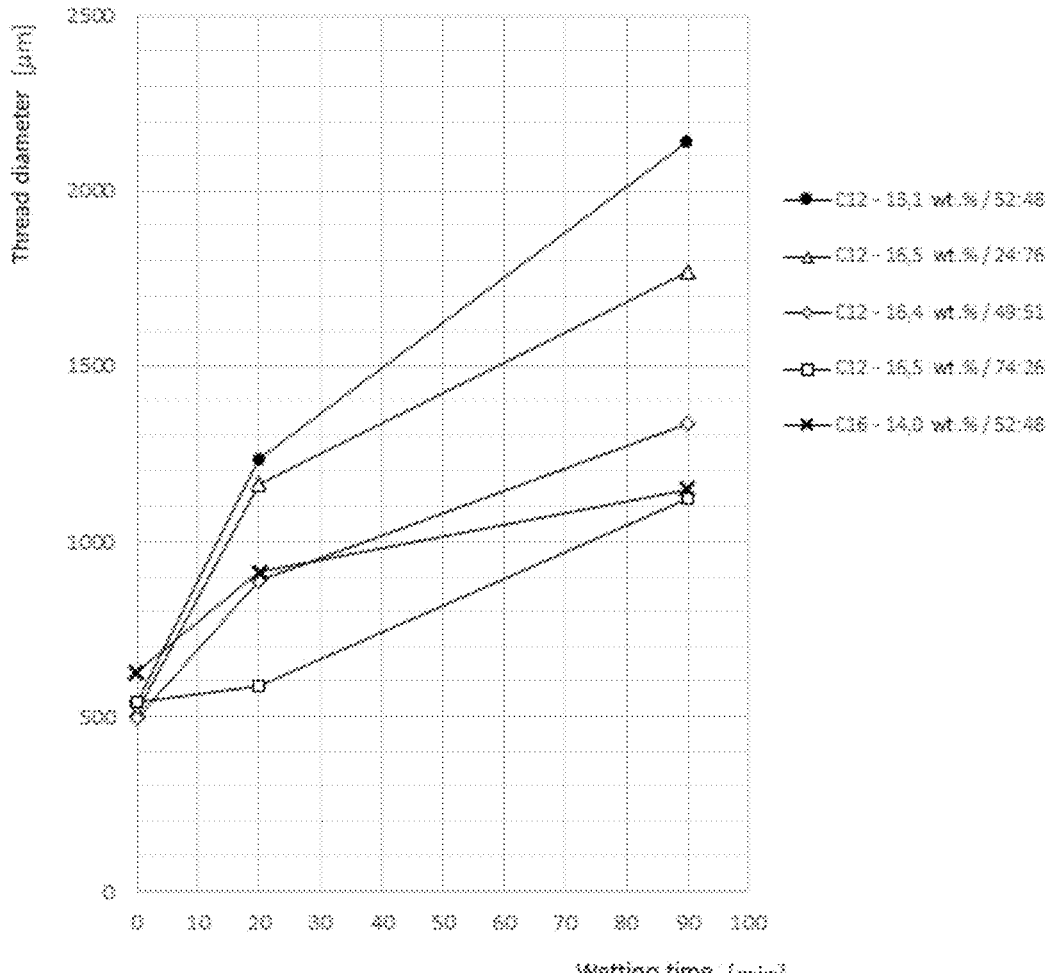
FIG. 6 provides a plot of wetting times for different diameter variants of a dental preparation in the form of a braided prepared in Example 12, tested against saliva.

Different variants of a dental preparation in the form of a braided thread consisting of hyaluronan fibers and lauroyl hyaluronan or palmitoyl hyaluronan fibers, from Example 12, are tested against saliva, with wetting times shown in the plot of FIG. 6. As shown, the swelling of different is dependent on the diameter of the thread on its wetting time in saliva.

REFERENCES

Bobula, T., Buffa, R., Hermannová, M., Kohutová, L., Procházková, P., Vágnerová, H. et al., 2017. A novel photopolymerizable derivative of hyaluronan for designed hydrogel formation. *Carbohydrate Polymers,* 161, 277-285.

Chmelař J., Mrázek, J., Hermannová, M., Kubala, L., AmbroŽová, G., Kocurková, A., Drmota, T., Negporová, K., Grusová, L., Velebný, V., 2019. Biodegradable free-standing films from lauroyl derivatives of hyaluronan. *Carbohydrate Polymers,* 224, 115162.

Golub, L. M., Suomalainen, K. and Sorsa, T., 1992. Host modulation with tetracyclines and their chemically modified analogues. *Curr Opin Dent,* 2, 80-90.

Gontiya, G., Galgali, S. R., 2012. Effect of hyaluronan on periodontitis: A clinical and histological study. *J Indian Soc Periodontol.* 16(2), 184-192.

Gurha, S. et al., 2016. Effect of Tetracycline Hydrochloride Fibers (PeriocolTc) on The Level of *P. Gingivalis* in Chronic Generalized Periodontitis: Clinical & Microbiological Study. IOSR *Journal of Dental and Medical Sciences,* 15 (8), 100-107.

Hardy, K., Sunnucks, K., Gil, H., Shabir, S., Trampari, E., Hawkey, P., Webber, M., 2018. Increased Usage of Antiseptics Is Associated with Reduced Susceptibility in Clinical Isolates of *Staphylococcus aureus. mBio,* May 29, 2018, DOI: 10.1128/mBio.00894-18.

Hoang, T., Jorgensen, M. G., Keim, R. G., Pattison, A. M., Slots, J., 2003. Povidone-iodine as a periodontal pocket disinfectant. *J Periodont Res* 38(3), 311-317.

Hübner, N.-O., Siebert, J., Kramer, A., 2010. Octenidine Dihydrochloride, a Modern Antiseptic for Skin, Mucous Membranes and Wounds. *Skin Pharmacol Physiol* 23, 244-258. Jain, N., Jain, G. K., Javed, S. et al., 2008. Recent approaches for the treatment of periodontitis. *Drug Discovery Today* 13, 932-943.

Jentsch, H., Pomowski, R., Kundt, G., Gocke, R., 2003. Treatment of gingivitis with hyaluronan. *J Clin Periodontol.* 30(2), 159-164.

Kataria, S., Chandrashekar, K. T., Mishra, R., Tripathi, V., Galav, A. and Sthapak, U., 2015. Effect of tetracycline HCL (periodontal µplus AB) on *Aggregatibacter actinomycetemcomitans* levels in chronic periodontitis. *Archives of Oral and Dental Research,* 2:1. Retrieved from http://www.vipoa.org/oraldent; <http://www.hoajonline.com/oralbiodent/2053-5775/3/2 #ref6>

Khattri, S., Arora, A., Sumanth, K. N., Prashanti, E., Bhat, K. G., Kusum, C., Johnson, T. M., Lodi, G., 2017. Adjunctive systemic antimicrobials for the non-surgical treatment of chronic and aggressive periodontitis. *Cochrane Database Syst Rev,* Issue 2. Art. No.: CD012568.

Kramer, A., Dissemond, J., Kim, S., Willy, C., Mayer, D., Papke, R., Tuchmann, F, Assadian, 0, 2018. Consensus on Wound Antisepsis: Update 2018. *Skin Pharmacol Physiol,* 31(1), 28-58.

Lachapelle, J.-M., 2014. A comparison of the irritant and allergenic properties of antiseptics. *Eur J Dermatol* 24 (1), 3-9.

Listgarten, M. A., Loomer, P. M., 2004. Microbial identification in the management of periodontal diseases: A systematic review. *Annals of Periodontology,* 8(1), 182-192.

Mesa, F. L., Aneiros, J., Cabrera, A., Bravo, M., Caballero, T., Revelles, F., Moral, R. G. de, O'Valle, F., 2002. Antiproliferative effect of topic hyaluronic acid gel. Study in gingival biopsies of patients with periodontal disease. *Histol and Histopathol.* 17(3), 747-753.

Müller, G., Kramer, A., 2008. Biocompatibility index of antiseptic agents by parallel assessment of antimicrobial activity and cellular cytotoxicity. *J. Antimicrob. Chemother,* 64, 1281-87.

Nair, S., Anoop, K., 2012. Intraperiodontal pocket: An ideal route for local antimicrobial drug delivery. *J Adv Pharm Technol Res.* 3 (1), 9-15.

Obermeier, A., Schneider, J., Wehner, S., Matl, F. D., Schieker, M., Eisenhart-Rothe, R. von, Stemberger, A., Burgkart, R., 2014. Novel high efficient coatings for anti-microbial surgical sutures using chlorhexidine in fatty acid slow-release carrier systems. *PLoS One,* 9(7), e101426.

Obermeier, A. et. al., 2015. In vitro evaluation of novel antimicrobial coatings for surgical sutures using octeni- dine. *BMC Microbiology,* 15.

Pepeliaev, S., Hrudíková, R., Jílková, J., Pavlik, J., Smirnou, D., Černý, Z., et al., 2017. Colorimetric enzyme-coupled assay for hyaluronic acid determination in complex samples. *European Polymer Journal,* 94, 460-470.

Piloni, A., Annibali, S., Dominici, F., Paolo, C. Di, Papa, M., Cassini, M. A., Polimeni, A., 2011. Evaluation of the efficacy of an hyaluronic acid-based biogel on periodontal clinical parameters. A randomized-controlled clinical pilot study. *Ann Stomatol,* 2(3-4), 3-9. Pirnazar, P., Wolin- sky, L., Nachnani, S., Haake, S., Pilloni, A., Bernard, G. W., 1999. Bacteriostatic Effects of Hyaluronic Acid. *J Periodontal,* 70(4), 370-374.

Quirynen, M., Teughels, W., Soete, M. De, Steenberghe, D. Van, 2000. Topical antiseptics and antibiotics in the initial therapy of chronic adult periodontitis: microbiological aspects. *Periodontology,* 2002,28, 72-90.

Rams, T., Slots, J., 1996. Local delivery of antimicrobial agents in the periodontal pocket. *Periodontology,* 10, 139-159.

Rocha, H. A. da, Silva, C. F., Santiago, F. L., Martins, L. G., Dias, P. C., Magalhães, D. de, 2015. Local Drug Delivery Systems in the Treatment of Periodontitis: A Literature Review. *J Int Acad Periodont,* 17(3), 82-90.

Sapna, N., Vandana, K. L., 2011. Evaluation of hyaluronan gel (Gengigel®) as a topical applicant in the treatment of gingivitis. *J Investig Clin Dent.* 2(3), 162-170.

Varoni, E., Tarce, M., Lodi, G., Carrassi, A., 2012. Chlo- rhexidine (CHX) in dentistry: state of the art. *Minerva Stomatologica,* 61(9), 399-419.

Welk, A. et al., 2016. Antibacterial and antiplaque efficacy of a commercially available octenidine-containing mou- thrinse. *Clin Oral Investig,* 20(7), 1469-1476.

The invention claimed is:

1. A biodegradable dental preparation in the form of at least one textile unit selected from the group of fibers, a woven, knitted, non-woven or braided fabric, or a twisted bundle of fibers, comprising:

(A) at least one water-soluble fiber of hyaluronic acid or a physiologically acceptable salt thereof and (B) at least one fiber of a non-polar hyaluronic acid derivative according to general formula I:

(I)

wherein R is hydrogen, a physiologically acceptable metal cation, benzyl, or ethyl, and $R^1$ is H or an acyl group selected from capronoyl, capryloyl, caprinoyl, lauroyl, myristoyl, palmitoyl, stearoyl, or oleoyl;

(C) at least one antimicrobial agent selected from anti- septics, antibiotics and combinations thereof;

wherein the preparation is in the form of (i): a single textile unit which is a fabric or a thread comprising a weight ratio of water-soluble hyaluronic acid fibers to fibers of non-polar hyaluronic acid of general formula I of from 5:95 to 95:5; or (ii) a set of at least two textile units, wherein the non-polar hyaluronic acid derivative com- prises at least one repeating unit comprising at least one substituent $R^1$ that is the acyl; and wherein the weight average molecular weight of the non-polar hyaluronic acid derivative of general formula I is from $1.0 \times 10^5$ to $1.2 \times 10^6$ g/mol.

2. The biodegradable dental preparation of claim 1, wherein: (i) the at least one water-soluble fiber (A) com- prises a hyaluronic acid or its physiologically acceptable salt having a weight average molecular weight of from $1.0 \times 10^5$ to $1.2 \times 10^6$ g/mol; (ii) the weight average molecular weight of the non-polar hyaluronic acid derivative of general for- mula I is from $2.5 \times 10^5$ to $4.5 \times 10^5$ g/mol; or (iii) both (i) and (ii).

3. The biodegradable dental preparation of claim 1, wherein the non-polar hyaluronic acid derivative of general formula I comprises at least one $R^1$ that is the acyl group.

4. The biodegradable dental preparation of claim 1, wherein the non-polar hyaluronic acid derivative according to general formula I comprises a weight fraction of the repeating unit comprising the at least one substituent $R^1$ that is the acyl group or at least one substituent R that is benzyl or ethyl of from 5 to 27 wt %, based on the weight of the non-polar hyaluronic acid derivative.

5. The biodegradable dental preparation of claim 1, wherein at least one of the following is true:

the biodegradable dental preparation comprises at least one fiber having the antimicrobial agent present in and/or on the surface thereof; and/or the antimicrobial agent is in the form of a deposit on at least one fiber and present in an amount of from 0.01 to 2.0 wt %.

6. The biodegradable dental preparation of claim 1, wherein the non-polar hyaluronic acid derivative according to general formula I comprises a weight fraction of the repeating unit comprising the at least one substituent $R^1$ that is the acyl group or at least one substituent R that is benzyl or ethyl 14.0 to 20.0 wt %.

7. The biodegradable dental preparation of claim 1 in the form of the set of at least two textile units, wherein set comprises at least one textile unit comprising a fiber, fibers, fabric or thread, provided that the preparation contains at least one water-soluble fiber from hyaluronic acid or a physiologically acceptable salt thereof, and at least one fiber of a non-polar derivative of hyaluronic acid of general formula I.

8. The biodegradable dental preparation of claim 7, wherein the set of at least two textile units comprises:

an upper textile unit comprising a fiber, fibers, fabric, or thread comprising at least one fiber of a non-polar hyaluronic acid derivative according to general formula I, wherein the weight fraction of substituent on non- polar derivative of hyaluronic acid according to general formula I is from 14 to 20 wt %; and a bottom textile unit comprising a fiber, fibers, fabric or thread comprising at least one fiber of hyaluronic acid or a physiologically acceptable salt thereof.

9. The biodegradable dental preparation of claim 8, wherein the bottom textile unit comprises at least one fiber of hyaluronic acid or a physiologically acceptable salt thereof and at least one fiber of non-polar hyaluronic acid derivative of general formula I, wherein the weight fraction of substituent on the non-polar hyaluronic acid derivative of general of formula I is from 5 to 14 wt %.

10. The biodegradable dental preparation of claim 8, wherein the weight ratio of fibers of hyaluronic acid or a physiologically acceptable salt thereof to fibers of non-polar hyaluronic acid derivative of general formula I contained in the upper textile unit is from 5:95 to 60:40, and the weight ratio of fibers of hyaluronic acid or a physiologically acceptable salt thereof to the fibers of non-polar hyaluronic acid derivative of general formula I contained in the bottom textile unit is from 20:80 to 80:0.

11. The biodegradable dental preparation of claim 8, wherein the upper textile further comprises at least one fiber of hyaluronic acid or a physiologically acceptable salt thereof; and
wherein the bottom textile further comprises at least one fiber of non-polar hyaluronic acid derivative of general formula I, wherein the weight fraction of substituent on the non-polar hyaluronic acid derivative of general formula I is from 14 to 20 wt %.

12. The biodegradable dental preparation of claim 11, wherein the weight ratio of fibers of hyaluronic acid or a physiologically acceptable salt thereof to fibers of non-polar hyaluronic acid of general formula I contained in the upper textile unit is from 5:95 to 60:40, and the weight ratio of fibers of hyaluronic acid or a physiologically acceptable salt thereof to the non-polar hyaluronic acid derivative fibers of general formula I contained in the bottom textile unit is from 50:50 to 95:5.

13. The biodegradable dental preparation of claim 1 in the form of the set of at least two textile units, wherein the set comprises:
an upper textile unit having fibers, fabric or thread comprising at least one fiber of hyaluronic acid or a physiologically acceptable salt thereof and at least one fiber of a non-polar hyaluronic acid derivative according to general formula I, wherein the weight fraction of the substituent on the non-polar hyaluronic acid derivative of general formula I is from 15.5 to 20 wt %;
a middle textile unit having fibers, fabric or thread comprising at least one fiber of hyaluronic acid or a physiologically acceptable salt thereof and at least one fiber of non-polar hyaluronic acid derivative of general formula I, wherein the weight fraction of substituent on the non-polar hyaluronic acid derivative of general formula I is from 12.5 to 15.5 wt %;
and a bottom textile unit having fibers, fabric or thread comprising at least one fiber of hyaluronic acid or a physiologically acceptable salt thereof and at least one fiber of non-polar hyaluronic acid derivative of general formula I, wherein the weight fraction of substituent on the non-polar hyaluronic acid derivative of general formula I is from 5 to 12.5 wt %.

14. The biodegradable dental preparation of claim 13, wherein the weight ratio of fibers of hyaluronic acid or a physiologically acceptable salt thereof to fibers of non-polar hyaluronic acid derivative of general formula I contained in the upper textile unit is from 5:95 to 60:40; wherein the weight ratio of fibers of hyaluronic acid or a physiologically acceptable salt thereof to the fibers of non-polar hyaluronic acid derivative of general formula I contained in the middle textile unit is from 20:80 to 80:20; and wherein the weight ratio of fibers of hyaluronic acid or a physiologically acceptable salt thereof to the fibers of non-polar hyaluronic acid derivative of general formula I contained in the bottom textile unit is from 20:80 to 80:20.

15. The biodegradable dental preparation of claim 1 in the form of the set of at least two textile units, wherein the set comprises:
an upper textile unit having fibers, fabric or thread comprising at least one fiber of hyaluronic acid or a physiologically acceptable salt thereof and at least one fiber of a non-polar hyaluronic acid derivative according to general formula I, wherein the weight fraction of substituent on the non-polar hyaluronic acid derivative of general formula I from 14.0 to 20 wt %;
a middle textile unit having fibers, fabric or thread comprising at least one fiber of hyaluronic acid or a physiologically acceptable salt thereof and at least one fiber of non-polar hyaluronic acid derivative of formula I, wherein the weight fraction of substituent on the nonpolar hyaluronic acid derivative of formula I is from 14.0 to 20.0 wt %; and
a bottom textile unit having fibers, fabric or thread comprising at least one fiber of hyaluronic acid or a physiologically acceptable salt thereof and at least one fiber of non-polar hyaluronic acid derivative of general formula I, wherein the weight fraction of the substituent on the non-polar hyaluronic acid derivative of general formula I is from 14.0 to 20.0 wt %.

16. The biodegradable dental preparation of claim 15, wherein the weight ratio of fibers of hyaluronic acid or a physiologically acceptable salt thereof to fibers of the non-polar hyaluronic acid derivative according to general formula I contained in the upper textile unit is from 5:95 to 50:50; wherein the weight ratio of fibers of hyaluronic acid or a physiologically acceptable salt thereof to the fibers of non-polar hyaluronic acid derivative of general formula I contained in the middle textile unit is from 30:70 to 70:30; and wherein the weight ratio of fibers of hyaluronic acid or a physiologically acceptable salt thereof to the fibers of non-polar hyaluronic acid derivative of general formula I contained in the bottom textile unit is from 50:50 to 95:5.

17. The biodegradable dental preparation of claim 1 in the form of the set of at least two textile units, wherein the set comprises
an upper textile unit having fibers, fabric or thread comprising at least one fiber of hyaluronic acid or a physiologically acceptable salt thereof and at least one fiber of a non-polar hyaluronic acid derivative according to general formula I, wherein the weight fraction of the substituent on the non-polar hyaluronic acid derivative of general formula I is from 14.0 to 20 wt %;
a middle textile unit having fibers, fabric or thread comprising at least one fiber of hyaluronic acid or a physiologically acceptable salt thereof and at least one fiber of non-polar hyaluronic acid derivative of general formula I, wherein the weight fraction of the substituent on the non-polar hyaluronic acid derivative of general formula I is from 14.0 to 20 wt %; and
a bottom textile unit having fibers, fabric or thread comprising at least one fiber of hyaluronic acid or a physiologically acceptable salt thereof and at least one fiber of non-polar hyaluronic acid derivative of general formula I, wherein the weight fraction of the substituent on the non-polar hyaluronic acid derivative of general formula I is from 5.0 to 14.0 wt %.

18. The biodegradable dental preparation of claim 17, wherein the weight ratio of fibers of hyaluronic acid or a physiologically acceptable salt thereof to fibers of non-polar hyaluronic acid derivative according to general formula I contained in the upper textile unit is from 5:95 to 50:50; wherein the weight ratio of fibers of hyaluronic acid or a physiologically acceptable salt thereof to the fibers of non-polar hyaluronic acid derivative of general formula I contained in the middle textile unit is from 30:0 to 70:30; and the weight ratio of the fibers of hyaluronic acid or a physiologically acceptable salt thereof to the fibers of non-polar hyaluronic acid derivative of general formula I contained in the bottom textile unit is from 20:80 to 80:20.

19. The biodegradable dental preparation of claim 1 in the form of the set of at least two textile units, wherein the set comprises an upper textile unit having a fiber, fibers, fabric or thread comprising at least one fiber of a non-polar hyaluronic acid derivative according to general formula I, wherein the weight fraction of substituent on non-polar derivative of hyaluronic acid of general formula I is from 14 to 20 wt %;

a middle textile unit having fibers, fabric or thread comprising at least one fiber of hyaluronic acid or a physiologically acceptable salt thereof and at least one fiber of non-polar hyaluronic acid derivative according to general formula I, wherein the weight fraction of the substituent on the non-polar hyaluronic acid derivative according to general formula I is from 14 to 20 wt %; and a bottom textile unit having a fiber, fibers, fabric or thread comprising at least one fiber of hyaluronic acid or a physiologically acceptable salt thereof.

20. The biodegradable dental preparation of claim 19, wherein the weight ratio of fibers of hyaluronic acid or a physiologically acceptable salt thereof to fibers of non-polar hyaluronic acid derivative of general formula I contained in the middle textile unit is from 20:80 to 80:20.

21. The biodegradable dental preparation of claim 1 in the form of the set of at least two textile units, wherein the set comprises:

an upper textile unit having fibers, fabric or thread comprising at least one chloramide fiber of a chloramide hyaluronic acid derivative according to general formula II and at least one fiber of a non-polar hyaluronic acid derivative according to general formula I, wherein the weight fraction of Cl in the chloramide derivative of hyaluronic acid of general formula II is from 0.4 to 4.7 wt % and the weight fraction of the substituent on the non-polar hyaluronic acid derivative of general formula I is from 15.5 to 20 wt %;

a middle textile unit having fibers, fabric or thread comprising at least one chloramide fiber of a chloramide derivative of hyaluronic acid of general formula II and at least one fiber of a nonpolar derivative of hyaluronic acid according to general formula I, wherein the weight fraction of Cl on chloramide derivative of hyaluronic acid according to general formula II is from 0.4 to 4.7 wt % and the weight fraction of the substituent on the non-polar hyaluronic acid derivative of general formula I is from 12.5 to 15.5 wt %; and;

a bottom textile unit having fibers, fabric or thread comprising at least one chloramide fiber of a chloramide derivative of hyaluronic acid according to general formula II and at least one fiber of hyaluronic acid or a physiologically acceptable salt thereof, wherein weight fraction of Cl on chloramide derivative of hyaluronic acid of general formula II is from 0.4 to 4.7 wt %.

22. The biodegradable dental preparation of claim 1 in the form of the set of at least two textile units, wherein the set comprises:

an upper textile unit having fibers, fabric or thread comprising at least one mixed chloramide fiber formed by a chloramide hyaluronic acid derivative of general formula II and a non-polar hyaluronic acid derivative of general formula I and at least one a fiber of a non-polar hyaluronic acid derivative of general formula I, wherein the weight fraction of Cl in the chloramide hyaluronic acid derivative of general formula II is from 4.2 to 8.1 wt % and the weight fraction of the substituent on the non-polar hyaluronic acid derivative of general formula I is from 12.5 to 20 wt %;

a middle textile unit having fibers, fabric or thread comprising at least one mixed chloramide fiber formed by a chloramide hyaluronic acid derivative of general formula II and a non-polar hyaluronic acid derivative of general formula I and at least one fiber of non-polar hyaluronic acid derivative of general formula I, wherein the weight fraction of Cl in the chloramide derivative of hyaluronic acid according to general formula II is from 4.2 to 8.1 wt % and the weight fraction of the substituent on the non-polar hyaluronic acid derivative of general formula I from 12.5 to 20 wt %; and a bottom textile unit having fibers, fabric or thread comprising at least one mixed chloramide fiber formed by a chloramide hyaluronic acid derivative of general formula II and a non-polar hyaluronic acid derivative of general formula I and at least one fiber of hyaluronic acid or a physiologically acceptable salt thereof, wherein the weight fraction of Cl in the chloramide derivative of hyaluronic acid according to general formula II is from 4.2 to 8.1 wt % and the weight fraction of the substituent on the non-polar hyaluronic acid derivative of general formula I is from 12.5 to 20 wt %.

23. The biodegradable dental preparation of claim 1 in the form of the set of at least two textile units, wherein the set comprises:

an upper textile unit having fibers, fabric or thread comprising at least one mixed chloramide fiber formed by a chloramide derivative of hyaluronic acid according to general formula II and hyaluronic acid or a physiologically acceptable salt thereof and at least one fiber from a non-polar hyaluronic acid derivative of general formula I, wherein the weight fraction of Cl in the chloramide hyaluronic acid derivative of general formula II is from 4.2 to 8.1 wt % and the weight fraction of the substituent on the non-polar hyaluronic acid derivative of general formula I is from 15.5 to 20 wt %;

a middle textile unit having fibers, fabric or thread comprising at least one mixed chloramide fiber formed by a chloramide derivative of hyaluronic acid of general formula II and hyaluronic acid or a physiologically acceptable salt thereof and at least one fiber of a non-polar hyaluronic acid derivative of general formula I, wherein the weight fraction of Cl in the chloramide derivative of hyaluronic acid of general formula II is from 4.2 to 8.1 wt % and the weight fraction of the substituent on the non-polar hyaluronic acid derivative of general formula I is from 12.5 to 15.5 wt %; and a bottom textile unit having fibers, fabric or thread comprising at least one mixed chloramide fiber formed by a chloramide derivative of hyaluronic acid of general formula II and hyaluronic acid or a physiologically acceptable salt thereof and at least one fiber of hyaluronic acid or a physiologically acceptable salt thereof, wherein the weight fraction of Cl on the chloramide derivative of hyaluronic acid of general formula II is from 4.2 to 8.1 wt %.

24. The biodegradable dental preparation of claim 23, wherein the weight fraction of chloramide fibers or mixed chloramide fibers contained in the upper textile unit is from 5 to 60 wt % with respect to the weight of the upper textile unit, the weight fraction of chloramide fibers or mixed chloramide fibers contained in the middle textile unit is from 20 to 80 wt % with respect to the weight of the middle textile unit, and the weight fraction of chloramide fibers or mixed chloramide fibers contained in the bottom textile unit is from 20 to 80 wt % with respect to the weight of the bottom textile unit.

25. The biodegradable dental preparation of claim 1, wherein the at least one textile unit is a strip of fabric comprising a width, in the dry state, of from 0.5 to 10 mm.

26. The biodegradable dental preparation of claim 1, wherein the at least one textile unit is thread comprising a diameter, in the dry state, of from 0.1 to 3 mm.

27. A method of ameliorating a periodontal disease selected from gingivitis, periodontitis, necrotizing ulcerative gingivitis, or a periodontal or oral mucosal injury with the biodegradable dental preparation of claim 1, the method comprising administering the biodegradable dental preparation to a subject.

28. The biodegradable dental preparation of claim 1, wherein:

the repeating unit comprises the at least one substituent $R^1$ that is the acyl group and is selected from capronoyl, capryloyl, caprinoyl, lauroyl, myristoyl, palmitoyl, stearoyl, or oleoyl;

the non-polar hyaluronic acid derivative according to general formula I comprises a weight fraction of the repeating unit comprising the at least one substituent $R^1$ that is the acyl group of from 5 to 27 wt %, based on the weight of the non-polar hyaluronic acid derivative; and the biodegradable dental preparation further comprises at least one antimicrobial agent selected from chlorhexidine or a physiologically acceptable salt thereof, or octenidine or a physiologically acceptable salt thereof.

29. The biodegradable dental preparation of claim 28, wherein the acyl group is selected from lauroyl or palmitoyl.

30. The biodegradable dental preparation of claim 29, wherein the non-polar hyaluronic acid derivative according to general formula I comprises a weight fraction of the repeating unit comprising the at least one substituent $R^1$ that is the acyl group of from 9 to 20 wt %, based on the weight of the non-polar hyaluronic acid derivative.

31. The biodegradable dental preparation of claim 30, wherein the antimicrobial agent is octenidine or a physiologically acceptable salt thereof.

32. The biodegradable dental preparation of claim 31, wherein:

the antimicrobial agent is octenidine dihydrochloride; and the biodegradable dental preparation comprises at least one fiber having the antimicrobial agent present in and/or on the surface thereof.

* * * * *